(12) United States Patent
Wang et al.

(10) Patent No.: US 7,672,789 B2
(45) Date of Patent: Mar. 2, 2010

(54) LEAST-SQUARE DECONVOLUTION (LSD): A METHOD TO RESOLVE DNA MIXTURES

(75) Inventors: Tse-Wei Wang, Oak Ridge, TN (US); Ning Xue, Knoxville, TN (US); John D Birdwell, Oak Ridge, TN (US); Mark Rader, Knoxville, TN (US); John Flaherty, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 978 days.

(21) Appl. No.: 11/413,183

(22) Filed: Apr. 28, 2006

(65) Prior Publication Data

US 2006/0190194 A1 Aug. 24, 2006

Related U.S. Application Data

(62) Division of application No. 10/265,908, filed on Oct. 8, 2002, now Pat. No. 7,162,372.

(51) Int. Cl.
*G06F 7/00* (2006.01)
(52) U.S. Cl. .............................. 702/19; 702/20; 703/11; 707/102
(58) Field of Classification Search ........................ None
See application file for complete search history.

(56) References Cited

U.S. PATENT DOCUMENTS

| | | | |
|---|---|---|---|
| 5,161,204 | A | 11/1992 | Hutcheson et al. |
| 5,273,632 | A | 12/1993 | Stockham et al. |
| 5,374,527 | A | 12/1994 | Grossman |
| 5,470,710 | A | 11/1995 | Weiss et al. |
| 5,541,067 | A | 7/1996 | Perlin |
| 5,580,728 | A | 12/1996 | Perlin |
| 5,759,369 | A | 6/1998 | Menchen et al. |
| 5,876,933 | A | 3/1999 | Perlin |
| 6,054,268 | A | 4/2000 | Perlin |
| 6,741,983 | B1 | 5/2004 | Birdwell et al. |
| 6,750,011 | B1 | 6/2004 | Perlin |
| 6,807,490 | B1 | 10/2004 | Perlin |
| 2002/0086289 | A1 | 7/2002 | Straus |
| 2002/0152035 | A1 | 10/2002 | Perlin |
| 2003/0143554 | A1 | 7/2003 | Berres et al. |

FOREIGN PATENT DOCUMENTS

WO 03056494 7/2003

OTHER PUBLICATIONS

Perlin, Mark W., et al., "Linear Mixture Analysis: A Mathematical Approach to Resolving Mixed DNA Samples", J Forensic Sci 2001, vol. 46, No. 6, pp. 1372-1378.
Perlin, Mark W., J Forensic Sci, Sep. 2002, vol. 47, No. 5, Paper ID JFS2002123_475.
Wang, Tse-wei, J Forensic Sci, Sep. 2002, vol. 47, No. 5, Paper ID JFS20002092_475, published Aug. 21, 2002.
Schwartz et al., "Flourescent Multiplex linkage analysis and carrier detection for Duchenne/Becker Muscular Dystrophy", Am. J. Human Genetics 51:721-729, 1992.
McConkey, E.H., Human Genetics, The Molecular Revolution Jones and Bartlett Publishers, 1993, pp. 92-112.
Clayton et al., "Analysis and Interpretation of Mixed Forensic Stains Using DNA STR Profiling", Forensic Science International, vol. 91 pp. 55-70 (1998).
Gill et al., Interpreting Simple STR Mixtures using Allele Peak Areas, 1998, Forensic Science International, vol. 91 pp. 41-53.
Evett et al., Taking Account of Peak Areas when Interpreting Mixed DNA Profiles, 1998, Journal of Forensic Sciences, vol. 43., No. 1, pp. 62-69.
Perlin et al., Toward Fully Automated Genotyping: Genotyping Microsatellite Markers by Deconvolution, 1995, AMerican Journal of Human Genet., vol. 57, pp. 1199-1210.
Wang, T and Xue, N, "Mixture STR/DNA Deconvolution Using Allele Peak Area Data and the Least Square Technique," 12th International Symposium on Human Identification, Biloxi, MS, Oct. 9-12, 2001.

*Primary Examiner*—Mary K Zeman
(74) *Attorney, Agent, or Firm*—PCT Law Group, PLLC; Thomas H. Jackson

(57) ABSTRACT

Least Square Deconvolution (LSD) uses quantitative allele peak area derived from a sample containing the DNA of more than one contributor to resolve the best-fit genotype profile of each contributor. The resolution is based on finding the least square fit of the mass ratio coefficients at each locus to come closest to the quantitative allele peak data. Consistent top-ranked mass ratio combinations from each locus can be pooled to form at least one composite DNA profile at a subset of the available loci. The top-ranked DNA profiles can be used to check against the profile of a suspect or be used to search for a matching profile in a DNA database.

21 Claims, 46 Drawing Sheets

The results for your LSD prepared for nxue Case ID: Texas_data_1 from host at Address 192.249.3.1

This report was prepared on Thu 30-May-2002 03:44 PM

LSD Results

| Locus | | Person 1 | Person 2 | Fitting Error | Error Ratio | Mass Ratio | Comments |
|---|---|---|---|---|---|---|---|
| D3S1358 | | | | | | | Three Alleles |
| | 1 | 16,17 | 15,17 | 9.6E-02 | 1.0 | 1.0:2.1 | |
| | 2 | 16,16 | 15,17 | 0.11 | 1.1 | 1.0:4.2 | |
| | 3 | 17,17 | 15,16 | 0.40 | 4.1 | 1.0:1.2 | |
| | 4 | 15,16 | 15,17 | 0.71 | 7.4 | 1.0:3.6 | |
| | 5 | 15,15 | 16,17 | 0.92 | 9.5 | 1.0:1.8 | |
| | 6 | 15,16 | 16,17 | 3.51 | 36 | 1.0:1.6 | |
| TH01 | | | | | | | No Alleles |
| D21S11 | | | | | | | Four Alleles |
| | 1 | 30.2,31.2 | 30,32.2 | 3.8E-03 | 1.0 | 1.0:1.6 | |
| | 2 | 30.2,32.2 | 30,31.2 | 0.44 | 116 | 1.0:1.0 | |
| | 3 | 31.2,32.2 | 30,30.2 | 0.44 | 117 | 1.0:1.0 | |
| D18S51 | | | | | | | Three Alleles |
| | 1 | 12,15 | 13,13 | 9.4E-03 | 1.0 | 1.0:1.8 | |
| | 2 | 13,15 | 12,13 | 1.02 | 108 | 1.0:1.1 | |
| | 3 | 15,15 | 12,13 | 3.77 | 402 | 1.0:5.0 | |
| | 4 | 12,12 | 13,15 | 4.16 | 443 | 1.0:4.3 | |
| | 5 | 12,15 | 12,13 | 4.68 | 499 | 1.0:-10.6 | |
| | 6 | 12,15 | 13,15 | 5.39 | 575 | 1.0:-12.5 | |

Figure 13B

| D5S818 | | | | | | Three Alleles |
|---|---|---|---|---|---|---|
| 1 | 7,12 | 13,13 | 1.4E-03 | 1.0 | 1.0:1.9 | |
| 2 | 7,13 | 12,13 | 1.11 | 778 | 1.0:1.0 | |
| 3 | 7,7 | 12,13 | 4.00 | 2793 | 1.0:4.9 | |
| 4 | 12,12 | 7,13 | 4.15 | 2899 | 1.0:4.6 | |
| 5 | 7,12 | 12,13 | 4.88 | 3412 | 1.0:-9.4 | |
| 6 | 7,12 | 7,13 | 5.16 | 3605 | 1.0:-10.0 | |
| D13S317 | | | | | | Three Alleles |
| 1 | 9,11 | 8,9 | 4.6E-03 | 1.0 | 1.0:2.4 | |
| 2 | 11,11 | 8,9 | 0.62 | 137 | 1.0:6.0 | |
| 3 | 8,11 | 9,9 | 1.06 | 232 | 1.0:1.0 | |
| 4 | 8,11 | 8,9 | 1.49 | 327 | 1.0:9.7 | |
| 5 | 8,8 | 9,11 | 3.31 | 724 | 1.0:1.9 | |
| 6 | 8,11 | 9,11 | 8.42 | 1844 | 1.0:2.4 | |
| D7S820 | | | | | | Two Alleles REVIEW the LSD Results |
| 1 | 10,10 | 11,11 | 0.0E+00 | | 1.0:1.9 | |
| 2 | 10,10 | 10,11 | 0.0E+00 | | 1.0:-4.2 | |
| 3 | 11,11 | 10,11 | 0.0E+00 | | 1.0:2.2 | |
| 4 | 10,11 | 10,11 | 0.41 | | 1.0:1.0 | |
| D16S539 | | | | | | No Alleles |
| CSF1PO | | | | | | No Alleles |
| VWA | | | | | | Three Alleles |
| 1 | 16,18 | 17,17 | 0.10 | 1.0 | 1.0:1.9 | |
| 2 | 17,18 | 16,17 | 1.77 | 18 | 1.0:1.3 | |
| 3 | 18,18 | 16,17 | 5.46 | 54 | 1.0:6.2 | |
| 4 | 16,18 | 16,17 | 6.18 | 61 | 1.0:-7.6 | |
| 5 | 16,16 | 17,18 | 7.05 | 70 | 1.0:4.0 | |
| 6 | 16,18 | 17,18 | 9.03 | 89 | 1.0:-10.6 | |

Figure 13C

D8S1179                              Three Alleles
    1     13,16 12,12 2.0E-03 1.0    1.0:1.9
    2     12,16 12,13 1.25       629    1.0:1.0
    3     16,16 12,13 4.30       2173 1.0:5.1
    4     13,13 12,16 4.49       2268 1.0:4.7
    5     13,16 12,13 5.16       2606 1.0:-8.6
    6     13,16 12,16 5.49       2775 1.0:-9.1

TPOX                                    No Alleles

FGA                                      Four Alleles
    1     23,25 22,24 0.26       1.0    1.0:2.0
    2     24,25 22,23 1.41       5.4    1.0:1.3
    3     23,24 22,25 1.67       6.4    1.0:1.0

PentaD                               No Alleles
PentaE                               No Alleles
D19S433                           No Alleles
D2S1338                           No Alleles
SE33                                 No Alleles Thu 30-May-2002 03:44 PM

Figure 16A

The results for your LSD prepared for nxue Case ID: Simulated_1to5 from host at Address 192.249.3.1

This report was prepared on Tue 09-Jul-2002 12:45 PM

LSD Results

| Locus | Person 1 | Person 2 | Fitting Error | Error Ratio | Mass Ratio | Comments |
|---|---|---|---|---|---|---|
| D3S1358 | | | | | | No Alleles |
| TH01 | | | | | | Three Alleles |
| 1 | 6,7 | 6,9.3 | 4.1E-02 | 1.0 | 1.0:7.0 | |
| 2 | 7,7 | 6,9.3 | 0.21 | 5.2 | 1.0:13.3 | |
| 3 | 7,9.3 | 6,9.3 | 0.91 | 22 | 1.0:14.3 | |
| 4 | 6,6 | 7,9.3 | 14.12 | 347 | 1.0:1.1 | |
| 5 | 9.3,9.3 | 6,7 | 17.79 | 437 | 1.0:1.3 | |
| 6 | 7,9.3 | 6,7 | 50.25 | 1234 | 1.0:1.3 | |
| D21S11 | | | | | | Two Alleles REVIEW the LSD Results |
| 1 | 28,28 | 30.2,30.2 | 0.0E+00 | | 1.0:5.5 | |
| 2 | 28,28 | 28,30.2 | 0.0E+00 | | 1.0:-2.4 | |
| 3 | 28,30.2 | 30.2,30.2 | 0.0E+00 | | 1.0:2.2 | |
| 4 | 28,30.2 | 28,30.2 | 9.96 | | 1.0:1.0 | |
| D18S51 | | | | | | Four Alleles |
| 1 | 16,20 | 17,18 | 0.76 | 1.0 | 1.0:5.6 | |
| 2 | 16,18 | 17,20 | 23.54 | 31 | 1.0:1.2 | |
| 3 | 18,20 | 16,17 | 23.63 | 31 | 1.0:1.2 | |
| D5S818 | | | | | | No Alleles |
| D13S317 | | | | | | No Alleles |
| D7S820 | | | | | | No Alleles |

Figure 16B

| | | | | | | |
|---|---|---|---|---|---|---|
| D16S539 | | | | | | No Alleles |
| CSF1PO | | | | | | No Alleles |
| VWA | | | | | | Three Alleles |
| 1 | 15,15 | 16,19 | 1.7E-03 | 1.0 | 1.0:5.2 | |
| 2 | 15,19 | 16,19 | 0.30 | 169 | 1.0:3.3 | |
| 3 | 15,16 | 16,19 | 0.37 | 214 | 1.0:3.5 | |
| 4 | 19,19 | 15,16 | 1.26 | 721 | 1.0:1.4 | |
| 5 | 16,16 | 15,19 | 1.36 | 775 | 1.0:1.4 | |
| 6 | 15,16 | 15,19 | 5.98 | 3417 | 1.0:1.1 | |
| D8S1179 | | | | | | Two Alleles REVIEW the LSD Results |
| 1 | 13,13 | 11,11 | 0.0E+00 | | 1.0:1.1 | |
| 2 | 11,11 | 11,13 | 0.0E+00 | | 1.0:16.2 | |
| 3 | 13,13 | 11,13 | 0.0E+00 | | 1.0:-18.2 | |
| 4 | 11,13 | 11,13 | 7.6E-03 | | 1.0:1.0 | |
| TPOX | | | | | | No Alleles |
| FGA | | | | | | Two Alleles REVIEW the LSD Results |
| 1 | 25,25 | 22,22 | 0.0E+00 | | 1.0:1.4 | |
| 2 | 22,22 | 22,25 | 0.0E+00 | | 1.0:4.5 | |
| 3 | 25,25 | 22,25 | 0.0E+00 | | 1.0:-6.5 | |
| 4 | 22,25 | 22,25 | 9.9E-02 | | 1.0:1.0 | |
| PentaD | | | | | | No Alleles |
| PentaE | | | | | | No Alleles |
| D19S433 | | | | | | No Alleles |
| D2S1338 | | | | | | No Alleles |
| SE33 | | | | | | No Alleles |

Tue 09-Jul-2002 12:45 PM

Figure 17A

The results for your LSD prepared for nxue Case ID: simulated_1to2 from host at Address 192.249.3.1
This report was prepared on Tue 09-Jul-2002 01:04 PM

LSD Results

| Locus | Person 1 | Person 2 | Fitting Error | Error Ratio | Mass Ratio | Comments |
|---|---|---|---|---|---|---|
| D3S1358 | | | | | | No Alleles |
| TH01 | | | | | | Three Alleles |
| 1 | 6,7 | 6,9.3 | 4.6E-05 | 1.0 | 1.0:1.7 | |
| 2 | 6,6 | 7,9.3 | 0.23 | 5078 | 1.0:1.0 | |
| 3 | 7,7 | 6,9.3 | 0.49 | 10641 | 1.0:4.4 | |
| 4 | 7,9.3 | 6,9.3 | 1.32 | 28715 | 1.0:6.0 | |
| 5 | 9.3,9.3 | 6,7 | 1.40 | 30420 | 1.0:2.2 | |
| 6 | 7,9.3 | 6,7 | 3.75 | 81692 | 1.0:2.7 | |
| D21S11 | | | | | | Two Alleles REVIEW the LSD Results |
| 1 | 28,28 | 30.2,30.2 | 0.0E+00 | | 1.0:1.8 | |
| 2 | 28,28 | 28,30.2 | 0.0E+00 | | 1.0:-4.6 | |
| 3 | 30.2,30.2 | 28,30.2 | 0.0E+00 | | 1.0:2.6 | |
| 4 | 28,30.2 | 28,30.2 | 0.29 | | 1.0:1.0 | |
| D18S51 | | | | | | Four Alleles |
| 1 | 16,20 | 17,18 | 5.7E-02 | 1.0 | 1.0:2.1 | |
| 2 | 16,18 | 17,20 | 1.52 | 27 | 1.0:1.1 | |
| 3 | 16,17 | 18,20 | 1.58 | 28 | 1.0:1.0 | |
| D5S818 | | | | | | No Alleles |
| D13S317 | | | | | | No Alleles |
| D7S820 | | | | | | No Alleles |

Figure 17B

| | | | | | | |
|---|---|---|---|---|---|---|
| D16S539 | | | | | | No Alleles |
| CSF1PO | | | | | | No Alleles |
| VWA | | | | | | Three Alleles |
| 1 | 15,15 | 16,19 | 1.2E-04 | 1.0 | 1.0:1.8 | |
| 2 | 19,19 | 15,16 | 5.2E-03 | 43 | 1.0:2.1 | |
| 3 | 16,16 | 15,19 | 6.9E-03 | 57 | 1.0:2.1 | |
| 4 | 15,19 | 15,16 | 0.27 | 2217 | 1.0:1.0 | |
| 5 | 16,19 | 15,16 | 0.40 | 3334 | 1.0:1.2 | |
| 6 | 16,19 | 15,19 | 0.43 | 3525 | 1.0:1.2 | |
| D8S1179 | | | | | | Two Alleles REVIEW the LSD Results |
| 1 | 11,11 | 13,13 | 0.0E+00 | | 1.0:1.1 | |
| 2 | 11,11 | 11,13 | 0.0E+00 | | 1.0:-25.5 | |
| 3 | 13,13 | 11,13 | 0.0E+00 | | 1.0:23.5 | |
| 4 | 11,13 | 11,13 | 3.6E-03 | | 1.0:1.0 | |
| TPOX | | | | | | No Alleles |
| FGA | | | | | | Two Alleles REVIEW the LSD Results |
| 1 | 25,25 | 22,22 | 0.0E+00 | | 1.0:2.1 | |
| 2 | 22,22 | 22,25 | 0.0E+00 | | 1.0:1.8 | |
| 3 | 25,25 | 22,25 | 0.0E+00 | | 1.0:-3.8 | |
| 4 | 22,25 | 22,25 | 0.60 | | 1.0:1.0 | |
| PentaD | | | | | | No Alleles |
| PentaE | | | | | | No Alleles |
| D19S433 | | | | | | No Alleles |
| D2S1338 | | | | | | No Alleles |
| SE33 | | | | | | No Alleles |

Tue 09-Jul-2002 01:04 PM

Figure 18A

The results for your LSD prepared for nxue Case ID: simulated_1to1 from host at Address 192.249.3.1
This report was prepared on Tue 09-Jul-2002 01:11 PM

LSD Results

| Locus | Person 1 | Person 2 | Fitting Error | Error Ratio | Mass Ratio | Comments |
|---|---|---|---|---|---|---|
| D3S1358 | | | | | | No Alleles |
| TH01 | | | | | | Three Alleles |
| 1 | 6,6 | 7,9.3 | 2.3E-04 | 1.0 | 1.0:1.0 | |
| 2 | 6,7 | 6,9.3 | 1.4E-03 | 6.3 | 1.0:1.0 | |
| 3 | 7,7 | 6,9.3 | 0.44 | 1932 | 1.0:3.0 | |
| 4 | 9.3,9.3 | 6,7 | 0.46 | 2021 | 1.0:2.9 | |
| 5 | 7,9.3 | 6,9.3 | 1.25 | 5519 | 1.0:3.7 | |
| 6 | 7,9.3 | 6,7 | 1.30 | 5764 | 1.0:3.6 | |
| D21S11 | | | | | | Two Alleles REVIEW the LSD Results |
| 1 | 30.2,30.2 | 28,28 | 0.0E+00 | | 1.0:1.1 | |
| 2 | 28,28 | 28,30.2 | 0.0E+00 | | 1.0:13.6 | |
| 3 | 30.2,30.2 | 28,30.2 | 0.0E+00 | | 1.0:-15.6 | |
| 4 | 28,30.2 | 28,30.2 | 1.1E-02 | | 1.0:1.0 | |
| D18S51 | | | | | | Four Alleles |
| 1 | 17,20 | 16,18 | 3.8E-03 | 1.0 | 1.0:1.1 | |
| 2 | 18,20 | 16,17 | 6.1E-03 | 1.6 | 1.0:1.0 | |
| 3 | 17,18 | 16,20 | 7.0E-03 | 1.8 | 1.0:1.0 | |
| D5S818 | | | | | | No Alleles |
| D13S317 | | | | | | No Alleles |

Figure 18B

| | | | | | | |
|---|---|---|---|---|---|---|
| D7S820 | | | | | | No Alleles |
| D16S539 | | | | | | No Alleles |
| CSF1PO | | | | | | No Alleles |
| VWA | | | | | | Three Alleles |
| 1 | 15,16 | 15,19 | 4.6E-04 | 1.0 | 1.0:1.1 | |
| 2 | 15,15 | 16,19 | 1.4E-03 | 3.1 | 1.0:1.0 | |
| 3 | 16,16 | 15,19 | 0.46 | 1017 | 1.0:3.1 | |
| 4 | 19,19 | 15,16 | 0.52 | 1133 | 1.0:2.9 | |
| 5 | 16,19 | 15,19 | 1.28 | 2817 | 1.0:3.9 | |
| 6 | 16,19 | 15,16 | 1.43 | 3132 | 1.0:3.6 | |
| D8S1179 | | | | | | Two Alleles REVIEW the LSD Results |
| 1 | 11,11 | 13,13 | 0.0E+00 | | 1.0:1.1 | |
| 2 | 11,11 | 11,13 | 0.0E+00 | | 1.0:-16.9 | |
| 3 | 13,13 | 11,13 | 0.0E+00 | | 1.0:14.9 | |
| 4 | 11,13 | 11,13 | 9.0E-03 | | 1.0:1.0 | |
| TPOX | | | | | | No Alleles |
| FGA | | | | | | Two Alleles REVIEW the LSD Results |
| 1 | 25,25 | 22,22 | 0.0E+00 | | 1.0:3.5 | |
| 2 | 22,25 | 22,22 | 0.0E+00 | | 1.0:1.3 | |
| 3 | 25,25 | 22,25 | 0.0E+00 | | 1.0:-2.8 | |
| 4 | 22,25 | 22,25 | 3.17 | | 1.0:1.0 | |
| PentaD | | | | | | No Alleles |
| PentaE | | | | | | No Alleles |
| D19S433 | | | | | | No Alleles |
| D2S1338 | | | | | | No Alleles |
| SE33 | | | | | | No Alleles |

Figure 19B

| CSF1PO | | | | | | No Alleles |
|---|---|---|---|---|---|---|
| VWA | | | | | | Four Alleles |
| 1 | 15,16 | 17,19 | 2.8E-02 | 1.0 | 1.0:1.8 | |
| 2 | 16,19 | 15,17 | 0.60 | 21 | 1.0:1.1 | |
| 3 | 15,19 | 16,17 | 0.61 | 22 | 1.0:1.1 | |
| D8S1179 | | | | | | Three Alleles |
| 1 | 14,15 | 13,13 | 1.8E-02 | 1.0 | 1.0:2.0 | |
| 2 | 13,14 | 13,15 | 1.49 | 83 | 1.0:1.1 | |
| 3 | 14,14 | 13,15 | 4.84 | 272 | 1.0:5.5 | |
| 4 | 15,15 | 13,14 | 5.45 | 306 | 1.0:4.5 | |
| 5 | 14,15 | 13,15 | 5.64 | 316 | 1.0:-7.9 | |
| 6 | 14,15 | 13,14 | 6.72 | 377 | 1.0:-9.1 | |
| TPOX | | | | | | No Alleles |
| FGA | | | | | | Two Alleles REVIEW the LSD Results |
| 1 | 22,22 | 23,23 | 0.0E+00 | | 1.0:5.2 | |
| 2 | 22,22 | 22,23 | 0.0E+00 | | 1.0:-2.5 | |
| 3 | 22,23 | 23,23 | 0.0E+00 | | 1.0:2.1 | |
| 4 | 22,23 | 22,23 | 8.94 | | 1.0:1.0 | |
| PentaD | | | | | | No Alleles |
| PentaE | | | | | | No Alleles |
| D19S433 | | | | | | No Alleles |
| D2S1338 | | | | | | No Alleles |
| SE33 | | | | | | No Alleles |

Fri 12-Jul-2002 09:51 AM

Figure 20B

| | | | | | |
|---|---|---|---|---|---|
| D13S317 | | | | | No Alleles |
| D7S820 | | | | | No Alleles |
| D16S539 | | | | | No Alleles |
| CSF1PO | | | | | No Alleles |
| VWA | | | | | Four Alleles |
| 1 | 17,19 | 16,18 | 7.85 | 1.0 | 1.0:8.4 |
| 2 | 16,19 | 17,18 | 487.58 | 62 | 1.0:1.2 |
| 3 | 18,19 | 16,17 | 488.74 | 62 | 1.0:1.1 |
| D8S1179 | | | | | Three Alleles |
| 1 | 10,11 | 10,14 | 0.32 | 1.0 | 1.0:11.4 |
| 2 | 11,11 | 10,14 | 1.95 | 6.1 | 1.0:31.5 |
| 3 | 11,14 | 10,14 | 2.95 | 9.3 | 1.0:2012.0 |
| 4 | 11,14 | 10,10 | 94.88 | 299 | 1.0:1.1 |
| 5 | 14,14 | 10,11 | 124.06 | 390 | 1.0:1.2 |
| 6 | 11,14 | 10,11 | 310.64 | 977 | 1.0:1.4 |
| TPOX | | | | | No Alleles |
| FGA | | | | | Three Alleles |
| 1 | 21,23 | 21,22 | 6.70 | 1.0 | 1.0:4.8 |
| 2 | 22,23 | 21,22 | 14.02 | 2.1 | 1.0:-11.8 |
| 3 | 23,23 | 21,22 | 15.04 | 2.2 | 1.0:26.3 |
| 4 | 22,23 | 21,21 | 44.11 | 6.6 | 1.0:1.4 |
| 5 | 22,22 | 21,23 | 110.66 | 17 | 1.0:1.6 |
| 6 | 22,23 | 21,23 | 212.84 | 32 | 1.0:3.8 |
| PentaD | | | | | No Alleles |
| PentaE | | | | | No Alleles |
| D19S433 | | | | | No Alleles |
| D2S1338 | | | | | No Alleles |
| SE33 | | | | | No Alleles |

Fri 12-Jul-2002 09:58 AM

Figure 21B

| D18S51 | | | | | Four Alleles |
|---|---|---|---|---|---|
| 1 | 14,18 | 13,15 | 0.88 | 1.0 | 1.0:6.8 |
| 2 | 15,18 | 13,14 | 48.64 | 55 | 1.0:1.2 |
| 3 | 14,15 | 13,18 | 49.15 | 56 | 1.0:1.1 |
| D5S818 | | | | | Three Alleles |
| 1 | 11,11 | 12,13 | 7.5E-02 | 1.0 | 1.0:8.7 |
| 2 | 11,12 | 12,13 | 0.13 | 1.7 | 1.0:5.0 |
| 3 | 11,13 | 12,13 | 0.64 | 8.6 | 1.0:7.6 |
| 4 | 12,12 | 11,13 | 5.00 | 67 | 1.0:1.1 |
| 5 | 13,13 | 11,12 | 6.30 | 84 | 1.0:1.3 |
| 6 | 11,13 | 11,12 | 19.83 | 265 | 1.0:1.2 |
| D13S317 | | | | | Four Alleles |
| 1 | 11,13 | 12,14 | 0.15 | 1.0 | 1.0:5.4 |
| 2 | 11,14 | 12,13 | 22.83 | 155 | 1.0:1.1 |
| 3 | 13,14 | 11,12 | 22.92 | 155 | 1.0:1.0 |
| D7S820 | | | | | Three Alleles |
| 1 | 8,12 | 8,10 | 0.28 | 1.0 | 1.0:7.7 |
| 2 | 12,12 | 8,10 | 1.84 | 6.6 | 1.0:21.5 |
| 3 | 10,12 | 8,10 | 2.84 | 10 | 1.0:386.2 |
| 4 | 10,12 | 8,8 | 38.59 | 138 | 1.0:1.1 |
| 5 | 10,10 | 8,12 | 57.26 | 204 | 1.0:1.3 |
| 6 | 10,12 | 8,12 | 139.89 | 499 | 1.0:1.6 |

Figure 21C

| D16S539 | | | | | | Four Alleles |
|---|---|---|---|---|---|---|
| 1 | 12,13 | 11,14 | 1.24 | 1.0 | 1.0:5.3 | |
| 2 | 12,14 | 11,13 | 22.85 | 18 | 1.0:1.3 | |
| 3 | 13,14 | 11,12 | 23.19 | 19 | 1.0:1.2 | |
| CSF1PO | | | | | | Three Alleles |
| 1 | 11,12 | 10,12 | 5.1E-02 | 1.0 | 1.0:4.5 | |
| 2 | 11,11 | 10,12 | 0.97 | 19 | 1.0:11.4 | |
| 3 | 10,11 | 10,12 | 1.90 | 38 | 1.0:27.4 | |
| 4 | 10,11 | 12,12 | 7.98 | 158 | 1.0:1.1 | |
| 5 | 10,10 | 11,12 | 14.49 | 287 | 1.0:1.5 | |
| 6 | 10,11 | 11,12 | 35.90 | 710 | 1.0:1.9 | |
| VWA | | | | | | Two Alleles REVIEW the LSD Results |
| 1 | 14,14 | 16,16 | 0.0E+00 | | 1.0:1.0 | |
| 2 | 14,14 | 14,16 | 0.0E+00 | | 1.0:-138.6 | |
| 3 | 16,16 | 14,16 | 0.0E+00 | | 1.0:136.6 | |
| 4 | 14,16 | 14,16 | 1.1E-04 | | 1.0:1.0 | |

Figure 21D

| D8S1179 | | | | | | Two Alleles REVIEW the LSD Results |
|---|---|---|---|---|---|---|
| 1 | 13,13 | 14,14 | 0.0E+00 | | 1.0:1.0 | |
| 2 | 13,13 | 13,14 | 0.0E+00 | | 1.0:-99.2 | |
| 3 | 14,14 | 13,14 | 0.0E+00 | | 1.0:97.2 | |
| 4 | 13,14 | 13,14 | 2.1E-04 | | 1.0:1.0 | |
| TPOX | | | | | | Two Alleles REVIEW the LSD Results |
| 1 | 11,11 | 8,8 | 0.0E+00 | | 1.0:1.0 | |
| 2 | 8,8 | 8,11 | 0.0E+00 | | 1.0:44.9 | |
| 3 | 11,11 | 8,11 | 0.0E+00 | | 1.0:-46.9 | |
| 4 | 8,11 | 8,11 | 9.9E-04 | | 1.0:1.0 | |
| FGA | | | | | | One Allele Only |
| 1 | 22,22 | 22,22 | | | 1:1 | |

Thu 30-May-2002 04:31 PM

The results for your LSD prepared for nxue Case ID: Acadiana_data_page2 from host at Address 192.249.3.1
This report was prepared on Thu 30-May-2002 04:42 PM
LSD Results

| Locus | Person 1 | Person 2 | Fitting Error | Error Ratio | Mass Ratio | Comments |
|---|---|---|---|---|---|---|
| D3S1358 | | | | | | Three Alleles |
| 1 | 15,15 | 14,17 | 1.1E-02 | 1.0 | 1.0:8.0 | |
| 2 | 14,15 | 14,17 | 0.24 | 23 | 1.0:5.1 | |
| 3 | 15,17 | 14,17 | 0.44 | 41 | 1.0:5.9 | |
| 4 | 14,14 | 15,17 | 4.24 | 398 | 1.0:1.2 | |
| 5 | 17,17 | 14,15 | 4.67 | 439 | 1.0:1.3 | |
| 6 | 15,17 | 14,15 | 16.19 | 1522 | 1.0:1.1 | |
| TH01 | | | | | | Three Alleles |
| 1 | 9.3,9.3 | 6,7 | 9.8E-05 | 1.0 | 1.0:9.9 | |
| 2 | 6,9.3 | 6,7 | 0.32 | 3314 | 1.0:6.9 | |
| 3 | 7,9.3 | 6,7 | 0.34 | 3504 | 1.0:7.0 | |
| 4 | 6,6 | 7,9.3 | 7.80 | 79744 | 1.0:1.2 | |
| 5 | 7,7 | 6,9.3 | 7.85 | 80309 | 1.0:1.2 | |
| 6 | 7,9.3 | 6,9.3 | 26.48 | 270749 | 1.0:1.0 | |

Figure 22B

| D21S11 | | | | | | Three Alleles |
|---|---|---|---|---|---|---|
| 1 | 28,30.2 | 28,32.2 | 4.9E-02 | 1.0 | 1.0:5.1 | |
| 2 | 30.2,30.2 | 28,32.2 | 0.19 | 3.8 | 1.0:9.8 | |
| 3 | 30.2,32.2 | 28,32.2 | 0.87 | 18 | 1.0:10.2 | |
| 4 | 28,28 | 30.2,32.2 | 6.53 | 132 | 1.0:1.1 | |
| 5 | 32.2,32.2 | 28,30.2 | 8.94 | 181 | 1.0:1.4 | |
| 6 | 30.2,32.2 | 28,30.2 | 26.07 | 528 | 1.0:1.4 | |
| D18S51 | | | | | | Three Alleles |
| 1 | 16,16 | 17,20 | 3.1E-02 | 1.0 | 1.0:4.4 | |
| 2 | 16,17 | 17,20 | 0.19 | 6.1 | 1.0:2.4 | |
| 3 | 16,20 | 17,20 | 0.52 | 17 | 1.0:3.3 | |
| 4 | 17,17 | 16,20 | 0.58 | 19 | 1.0:1.3 | |
| 5 | 20,20 | 16,17 | 0.88 | 29 | 1.0:1.6 | |
| 6 | 16,20 | 16,17 | 3.86 | 126 | 1.0:1.3 | |
| D5S818 | | | | | | Two Alleles REVIEW the LSD Results |
| 1 | 12,12 | 11,11 | 0.0E+00 | | 1.0:4.6 | |
| 2 | 11,12 | 11,11 | 0.0E+00 | | 1.0:1.8 | |
| 3 | 12,12 | 11,12 | 0.0E+00 | | 1.0:-2.5 | |
| 4 | 11,12 | 11,12 | 6.64 | | 1.0:1.0 | |

Figure 22C

| D13S317 | | | | | | Three Alleles |
|---|---|---|---|---|---|---|
| 1 | 11,11 | 8,12 | 1.4E-04 | 1.0 | 1.0:9.2 | |
| 2 | 8,11 | 8,12 | 0.32 | 2304 | 1.0:6.3 | |
| 3 | 11,12 | 8,12 | 0.34 | 2464 | 1.0:6.4 | |
| 4 | 8,8 | 11,12 | 6.42 | 45931 | 1.0:1.2 | |
| 5 | 12,12 | 8,11 | 6.48 | 46361 | 1.0:1.2 | |
| 6 | 11,12 | 8,11 | 22.34 | 159689 | 1.0:1.0 | |
| D7S820 | | | | | | Two Alleles REVIEW the LSD Results |
| 1 | 12,12 | 10,10 | 0.0E+00 | | 1.0:15.4 | |
| 2 | 10,12 | 10,10 | 0.0E+00 | | 1.0:7.2 | |
| 3 | 12,12 | 10,12 | 0.0E+00 | | 1.0:-2.1 | |
| 4 | 10,12 | 10,12 | 103.08 | | 1.0:1.0 | |
| D16S539 | | | | | | Three Alleles |
| 1 | 11,11 | 8,10 | 2.2E-03 | 1.0 | 1.0:10.8 | |
| 2 | 8,11 | 8,10 | 0.29 | 130 | 1.0:7.4 | |
| 3 | 10,11 | 8,10 | 0.38 | 169 | 1.0:7.9 | |
| 4 | 8,8 | 10,11 | 9.60 | 4285 | 1.0:1.2 | |
| 5 | 10,10 | 8,11 | 9.89 | 4417 | 1.0:1.2 | |
| 6 | 10,11 | 8,11 | 32.20 | 14379 | 1.0:1.0 | |
| CSF1PO | | | | | | Three Alleles |
| 1 | 8,11 | 10,11 | 9.1E-02 | 1.0 | 1.0:6.9 | |
| 2 | 8,8 | 10,11 | 0.11 | 1.3 | 1.0:12.1 | |
| 3 | 8,10 | 10,11 | 0.73 | 8.0 | 1.0:11.5 | |
| 4 | 11,11 | 8,10 | 11.67 | 128 | 1.0:1.1 | |
| 5 | 10,10 | 8,11 | 14.09 | 155 | 1.0:1.3 | |
| 6 | 8,10 | 8,11 | 41.37 | 454 | 1.0:1.2 | |

Figure 22D

| VWA | | | | | Three Alleles |
|---|---|---|---|---|---|
| 1 | 19,19 | 15,16 | 3.0E-05 | 1.0 | 1.0:10.1 |
| 2 | 15,19 | 15,16 | 0.33 | 11075 | 1.0:7.0 |
| 3 | 16,19 | 15,16 | 0.34 | 11421 | 1.0:7.1 |
| 4 | 15,15 | 16,19 | 8.15 | 275159 | 1.0:1.2 |
| 5 | 16,16 | 15,19 | 8.19 | 276209 | 1.0:1.2 |
| 6 | 16,19 | 15,19 | 27.51 | 928267 | 1.0:1.0 |
| D8S1179 | | | | | Four Alleles |
| 1 | 13,15 | 11,14 | 0.49 | 1.0 | 1.0:3.2 |
| 2 | 14,15 | 11,13 | 6.91 | 14 | 1.0:1.3 |
| 3 | 13,14 | 11,15 | 7.25 | 15 | 1.0:1.1 |
| TPOX | | | | | Three Alleles |
| 1 | 8,12 | 9,9 | 1.0E-02 | 1.0 | 1.0:2.7 |
| 2 | 9,12 | 8,9 | 4.62 | 453 | 1.0:1.1 |
| 3 | 8,12 | 8,9 | 10.91 | 1071 | 1.0:-4.4 |
| 4 | 12,12 | 8,9 | 11.15 | 1094 | 1.0:7.0 |
| 5 | 8,8 | 9,12 | 11.83 | 1161 | 1.0:6.0 |
| 6 | 8,12 | 9,12 | 12.03 | 1181 | 1.0:-4.5 |
| FGA | | | | | Three Alleles |
| 1 | 25,25 | 22,24 | 1.1E-02 | 1.0 | 1.0:10.9 |
| 2 | 24,25 | 22,24 | 0.24 | 22 | 1.0:7.1 |
| 3 | 22,25 | 22,24 | 0.44 | 40 | 1.0:8.3 |
| 4 | 24,24 | 22,25 | 9.48 | 854 | 1.0:1.2 |
| 5 | 22,22 | 24,25 | 10.14 | 914 | 1.0:1.2 |
| 6 | 22,25 | 24,25 | 32.38 | 2918 | 1.0:1.1 |

Thu 30-May-2002 04:42 PM

Figure 23B

| D18S51 | | | | | | Three Alleles |
|---|---|---|---|---|---|---|
| 1 | 12,18 | 17,17 | 3.6E-02 | 1.0 | 1.0:1.2 | |
| 2 | 12,17 | 17,18 | 8.3E-02 | 2.3 | 1.0:1.2 | |
| 3 | 12,12 | 17,18 | 1.12 | 32 | 1.0:4.0 | |
| 4 | 18,18 | 12,17 | 1.56 | 44 | 1.0:3.0 | |
| 5 | 12,18 | 17,18 | 2.08 | 59 | 1.0:11.6 | |
| 6 | 12,18 | 12,17 | 3.07 | 86 | 1.0:6.9 | |
| D5S818 | | | | | | Two Alleles REVIEW the LSD Results |
| 1 | 11,11 | 10,10 | 0.0E+00 | | 1.0:1.2 | |
| 2 | 10,10 | 10,11 | 0.0E+00 | | 1.0:8.8 | |
| 3 | 11,11 | 10,11 | 0.0E+00 | | 1.0:-10.8 | |
| 4 | 10,11 | 10,11 | 2.6E-02 | | 1.0:1.0 | |
| D13S317 | | | | | | Two Alleles REVIEW the LSD Results |
| 1 | 9,9 | 12,12 | 0.0E+00 | | 1.0:2.8 | |
| 2 | 9,9 | 9,12 | 0.0E+00 | | 1.0:-3.1 | |
| 3 | 12,12 | 9,12 | 0.0E+00 | | 1.0:1.1 | |
| 4 | 9,12 | 9,12 | 1.66 | | 1.0:1.0 | |
| D7S820 | | | | | | Two Alleles REVIEW the LSD Results |
| 1 | 8,8 | 11,11 | 0.0E+00 | | 1.0:1.7 | |
| 2 | 8,8 | 8,11 | 0.0E+00 | | 1.0:-5.0 | |
| 3 | 11,11 | 8,11 | 0.0E+00 | | 1.0:3.0 | |
| 4 | 8,11 | 8,11 | 0.22 | | 1.0:1.0 | |
| D16S539 | | | | | | Three Alleles |
| 1 | 12,13 | 11,12 | 7.3E-03 | 1.0 | 1.0:1.7 | |
| 2 | 12,12 | 11,13 | 0.22 | 30 | 1.0:1.1 | |
| 3 | 13,13 | 11,12 | 0.36 | 50 | 1.0:4.2 | |
| 4 | 11,13 | 11,12 | 1.14 | 157 | 1.0:5.0 | |
| 5 | 11,11 | 12,13 | 1.15 | 157 | 1.0:2.1 | |
| 6 | 11,13 | 12,13 | 3.37 | 462 | 1.0:2.4 | |

Figure 23C

| | | | | | |
|---|---|---|---|---|---|
| CSF1PO | | | | | Two Alleles REVIEW the LSD Results |
| 1 | 10,10 | 11,11 | 0.0E+00 | | 1.0:2.0 |
| 2 | 10,10 | 10,11 | 0.0E+00 | | 1.0:-4.1 |
| 3 | 11,11 | 10,11 | 0.0E+00 | | 1.0:2.1 |
| 4 | 10,11 | 10,11 | 0.47 | | 1.0:1.0 |
| VWA | | | | | Two Alleles REVIEW the LSD Results |
| 1 | 14,14 | 17,17 | 0.0E+00 | | 1.0:2.4 |
| 2 | 14,14 | 14,17 | 0.0E+00 | | 1.0:-3.4 |
| 3 | 17,17 | 14,17 | 0.0E+00 | | 1.0:1.4 |
| 4 | 14,17 | 14,17 | 0.99 | | 1.0:1.0 |
| D8S1179 | | | | | Three Alleles |
| 1 | 11,12 | 12,15 | 1.6E-02 | 1.0 | 1.0:1.2 |
| 2 | 12,12 | 11,15 | 1.9E-02 | 1.2 | 1.0:1.1 |
| 3 | 11,11 | 12,15 | 0.31 | 19 | 1.0:3.2 |
| 4 | 15,15 | 11,12 | 0.47 | 30 | 1.0:2.5 |
| 5 | 11,15 | 12,15 | 1.06 | 67 | 1.0:3.4 |
| 6 | 11,15 | 11,12 | 1.57 | 99 | 1.0:2.7 |
| TPOX | | | | | Two Alleles REVIEW the LSD Results |
| 1 | 10,10 | 9,9 | 0.0E+00 | | 1.0:1.3 |
| 2 | 9,9 | 9,10 | 0.0E+00 | | 1.0:7.9 |
| 3 | 10,10 | 9,10 | 0.0E+00 | | 1.0:-9.9 |
| 4 | 9,10 | 9,10 | 3.2E-02 | | 1.0:1.0 |
| FGA | | | | | Two Alleles REVIEW the LSD Results |
| 1 | 23,23 | 22,22 | 0.0E+00 | | 1.0:1.2 |
| 2 | 22,22 | 22,23 | 0.0E+00 | | 1.0:9.6 |
| 3 | 23,23 | 22,23 | 0.0E+00 | | 1.0:-11.6 |
| 4 | 22,23 | 22,23 | 2.2E-02 | | 1.0:1.0 |

Thu 30-May-2002 04:26 PM

Figure 25B

| D18S51 | | | | | | Three Alleles |
|---|---|---|---|---|---|---|
| 1 | 18,19 | 17,19 | 2.0E-02 | 1.0 | 1.0:1.5 | |
| 2 | 19,19 | 17,18 | 0.12 | 5.9 | 1.0:1.1 | |
| 3 | 18,18 | 17,19 | 0.28 | 14 | 1.0:3.7 | |
| 4 | 17,17 | 18,19 | 0.77 | 38 | 1.0:2.2 | |
| 5 | 17,18 | 17,19 | 1.03 | 51 | 1.0:4.0 | |
| 6 | 17,18 | 18,19 | 2.48 | 124 | 1.0:2.3 | |
| D5S818 | | | | | | Three Alleles |
| 1 | 11,12 | 11,13 | 3.6E-04 | 1.0 | 1.0:1.2 | |
| 2 | 12,13 | 11,11 | 2.1E-02 | 59 | 1.0:1.0 | |
| 3 | 12,12 | 11,13 | 0.53 | 1473 | 1.0:3.4 | |
| 4 | 13,13 | 11,12 | 0.77 | 2123 | 1.0:2.7 | |
| 5 | 12,13 | 11,13 | 1.38 | 3804 | 1.0:4.8 | |
| 6 | 12,13 | 11,12 | 2.00 | 5511 | 1.0:3.6 | |
| D13S317 | | | | | | Four Alleles |
| 1 | 9,12 | 11,14 | 1.4E-02 | 1.0 | 1.0:1.3 | |
| 2 | 12,14 | 9,11 | 7.4E-02 | 5.3 | 1.0:1.1 | |
| 3 | 11,12 | 9,14 | 8.7E-02 | 6.3 | 1.0:1.0 | |
| D7S820 | | | | | | Two Alleles REVIEW the LSD Results |
| 1 | 12,12 | 10,10 | 0.0E+00 | | 1.0:2.3 | |
| 2 | 10,10 | 10,12 | 0.0E+00 | | 1.0:1.6 | |
| 3 | 12,12 | 10,12 | 0.0E+00 | | 1.0:-3.6 | |
| 4 | 10,12 | 10,12 | 0.80 | | 1.0:1.0 | |

Figure 25C

| | | | | | | |
|---|---|---|---|---|---|---|
| D16S539 | | | | | | No Alleles |
| CSF1PO | | | | | | No Alleles |
| VWA | | | | | | One Allele Only |
| 1 | 16,16 | 16,16 | | | 1:1 | |
| D8S1179 | | | | | | Three Alleles |
| 1 | 10,12 | 10,13 | 6.1E-03 | 1.0 | 1.0:1.7 | |
| 2 | 10,10 | 12,13 | 0.20 | 32 | 1.0:1.1 | |
| 3 | 12,12 | 10,13 | 0.37 | 61 | 1.0:4.1 | |
| 4 | 13,13 | 10,12 | 1.12 | 182 | 1.0:2.1 | |
| 5 | 12,13 | 10,13 | 1.16 | 189 | 1.0:5.0 | |
| 6 | 12,13 | 10,12 | 3.26 | 531 | 1.0:2.5 | |
| TPOX | | | | | | No Alleles |
| FGA | | | | | | Three Alleles |
| 1 | 21,21 | 20,22 | 4.0E-04 | 1.0 | 1.0:1.5 | |
| 2 | 22,22 | 20,21 | 6.8E-02 | 171 | 1.0:2.4 | |
| 3 | 20,20 | 21,22 | 7.8E-02 | 198 | 1.0:2.3 | |
| 4 | 21,22 | 20,21 | 0.13 | 336 | 1.0:1.0 | |
| 5 | 20,22 | 20,21 | 0.62 | 1575 | 1.0:1.7 | |
| 6 | 20,22 | 21,22 | 0.68 | 1708 | 1.0:1.7 | |

Thu 30-May-2002 04:56 PM

Figure 27B

| D18S51 | | | | | Two Alleles REVIEW the LSD Results |
|---|---|---|---|---|---|
| 1 | 14,14 | 12,12 | 0.0E+00 | | 1.0:1.2 |
| 2 | 12,12 | 12,14 | 0.0E+00 | | 1.0:12.6 |
| 3 | 14,14 | 12,14 | 0.0E+00 | | 1.0:-14.6 |
| 4 | 12,14 | 12,14 | 1.3E-02 | | 1.0:1.0 |
| D5S818 | | | | | Three Alleles |
| 1 | 11,13 | 11,12 | 1.5E-02 | 1.0 | 1.0:3.6 |
| 2 | 13,13 | 11,12 | 0.31 | 20 | 1.0:7.6 |
| 3 | 12,13 | 11,12 | 1.06 | 70 | 1.0:8.9 |
| 4 | 11,11 | 12,13 | 2.91 | 192 | 1.0:1.1 |
| 5 | 12,12 | 11,13 | 5.12 | 338 | 1.0:1.5 |
| 6 | 12,13 | 11,13 | 14.58 | 961 | 1.0:1.7 |
| D13S317 | | | | | Three Alleles |
| 1 | 12,12 | 8,13 | 2.2E-02 | 1.0 | 1.0:3.9 |
| 2 | 8,12 | 8,13 | 0.21 | 9.7 | 1.0:2.1 |
| 3 | 8,8 | 12,13 | 0.35 | 16 | 1.0:1.4 |
| 4 | 12,13 | 8,13 | 0.49 | 23 | 1.0:2.8 |
| 5 | 13,13 | 8,12 | 0.55 | 25 | 1.0:1.7 |
| 6 | 12,13 | 8,12 | 2.78 | 129 | 1.0:1.2 |
| D7S820 | | | | | Four Alleles |
| 1 | 8,9 | 10,11 | 0.33 | 1.0 | 1.0:3.9 |
| 2 | 8,11 | 9,10 | 10.26 | 32 | 1.0:1.2 |
| 3 | 9,11 | 8,10 | 10.40 | 32 | 1.0:1.1 |

Figure 27C

| | | | | | |
|---|---|---|---|---|---|
| D16S539 | | | | | No Alleles |
| CSF1PO | | | | | No Alleles |
| VWA | | | | | Four Alleles |
| 1 | 15,16 | 11,19 | 8.0E-02 | 1.0 | 1.0:4.4 |
| 2 | 16,19 | 11,15 | 11.99 | 150 | 1.0:1.1 |
| 3 | 15,19 | 11,16 | 11.99 | 150 | 1.0:1.1 |
| D8S1179 | | | | | Four Alleles |
| 1 | 13,16 | 10,15 | 6.0E-02 | 1.0 | 1.0:3.8 |
| 2 | 15,16 | 10,13 | 9.77 | 163 | 1.0:1.1 |
| 3 | 13,15 | 10,16 | 9.82 | 164 | 1.0:1.0 |
| TPOX | | | | | No Alleles |
| FGA | | | | | Four Alleles |
| 1 | 20,21 | 24,25 | 0.15 | 1.0 | 1.0:3.8 |
| 2 | 21,24 | 20,25 | 8.97 | 60 | 1.0:1.1 |
| 3 | 20,24 | 21,25 | 9.03 | 61 | 1.0:1.1 |

Thu 30-May-2002 04:43 PM

LEAST-SQUARE DECONVOLUTION (LSD): A METHOD TO RESOLVE DNA MIXTURES

This application is a divisional of and claims priority to U.S. Ser. No. 10/265,908, filed Oct. 8, 2002, now U.S. Pat. No. 7,162,372 which is incorporated herein in its entirety.

The U.S. Government retains certain rights in this invention due to funding provided by contract J-FBI-98-083 awarded by the Federal Bureau of Investigation.

FIELD OF THE INVENTION

The invention is related to methods of resolving a sample containing the DNA of more than one individual into a genotype profile for each individual in the sample.

BACKGROUND OF THE INVENTION

DNA identification has become one of the most important application tools in forensic science since DNA typing methodologies were introduced around 1985 and may be one of the most important discoveries in the field since the introduction of fingerprinting. With its extremely high capability to differentiate one individual from another (2), it has become widely used in courts around the country and worldwide.

In recent years, as DNA typing technology has improved and a national DNA database has become available, the popularity and effectiveness of DNA typing methodologies has increased. DNA analysts and other law enforcement agencies have been trying to understand the hidden information contained in DNA through an understanding of the molecular biology, genetics, and statistics involved to provide justice in trials. Because the probability that one person has the same genotype at a set of prescribed DNA loci as another person is very small, DNA typing is widely used in forensic identification, especially when unidentified criminals leave testable evidence such as semen, blood, and saliva at crime scenes. These important stains provide the extracted DNA samples that are to be used for criminal identification.

DNA typing for forensic applications is based on applying statistical tools to fundamental principles of diagnosis and gene characteristic analysis (2). The DNA profile obtained from criminal evidence has a unique identity, and the characteristics of the DNA profile are analyzed using these methods. The objective of DNA typing is to identify the genotype of the individual who left the evidence. After the perpetrator's genotype is obtained from DNA analysis, forensic caseworkers can compare the genotype of the criminal with that of a suspect or can search for a matching DNA profile in the local, state, and national CODIS databases for a possible suspect (2). Therefore, as an early step in investigation, DNA typing results of forensic samples should be obtained.

In many cases, especially in rape cases, when a DNA sample is extracted from a biological stain containing body fluids or tissues from more than one person, the result is often a mixed DNA profile. This kind of DNA profile is essentially composed of one contributor's DNA sample superimposed on that of another (3). Much of the DNA evidence obtained from crime scenes is a mixture of more than one contributor's DNA. Generally, the genotype of the victim is known, but the genotype of the perpetrator cannot be obtained clearly and directly due to the presence of DNA of another person in the sample. The genotype of each contributor to the DNA mixture must be deciphered first before further investigation.

Until now, the deconvolution of mixed DNA profiles contributed by multiple people has been one of the most challenging tasks facing forensic scientists. Part of the difficulty derives from the large number of possible genotype combinations that can be exhibited by the multiple contributors (4) in the mixed DNA profile. So far, no analytical and reliable method has been published for the resolution of DNA mixture into its components.

Early methods to resolve the genotype profile of contributors in a sample used loci with four alleles to estimate the mass ratio between the two contributors (5). For a locus with four detected alleles, each contributor has to have two different alleles with no shared allele between the two contributors. Therefore, only one allele assignment structure is possible (two heterozygotes). For loci with only two or three alleles more than one possible allele assignment structure is possible at each locus. To determine the genotype profile of an individual at two- or three-allele loci, an initial-guess mass ratio derived from the four-allele loci was used to estimate and evaluate all the possible allele assignment combinations that could be made by the contributors to the sample. The mass ratio at the two- and three-allele loci that best fit the observed relative allele peak areas was identified as the contributor's genotype profiles. This procedure was labor-intensive, and yielded a conservative resolution result.

More recently, in 1998, the British group of P. Gill et al. of the Forensic Science Services (5) presented a novel method to resolve DNA mixtures using quantitative allele peak data. This method requires an iterative search for the optimum mass ratio to fit the allele peaks at each locus that an individual can contribute to a sample. For each mass ratio used to fit each possible genotype profile, the residuals between the expected allele peak areas and those obtained from the measured allele peaks are calculated. The smallest residual at each locus is added to the minimum residuals similarly derived from allele peak data available at other loci. The genotype combinations that give the overall lowest minimum residual are selected to be the best-fit genotype combinations for the loci. This method is limiting and artificial because a finite set of prior-determined mass ratios is used to calculate the fitting residual. Further, this method is labor intensive because iterations are involved in searching for the best-fit genotype combinations.

In 2001, Mark Perlin and Beata Szababy developed the Linear Mixture Analysis (LMA) method to resolve DNA mixtures using quantitative allele peak data (18). In this method, all the quantitative allele peak data of all loci in a sample are integrated into a single matrix computation (18). This method imposes the same mass ratio to all loci analyzed in the mixture. This is in contrast to the observation that the best-fit mass ratio may vary from locus to locus in a sample, due to unequal DNA amplification and other nonidealities (24). It is predicted that the imposition of the same weight fractions to fit all loci will present a limitation on that set of weight fractions being optimal for all loci.

There is a need in the art for an efficient and accurate method to resolve a sample mixture of DNA into the genotype of each individual whose DNA is contained within the mixture.

BRIEF SUMMARY OF THE INVENTION

The invention encompasses a method of resolving a mixture comprising DNA of more than one individual into genotype profiles for individuals in the mixture. When the method of the present invention is implemented in application software or otherwise, it will be referred to herein as LSD. LSD is an acronym for a mathematical process, in particular, least square deconvolution, which we have picked as the name of the present method, for example, when embodied in software. The use of the acronym LSD is not intended to be limited in describing the present method itself or particular steps of the method for which other steps and known mathematical processes may be substituted by one of skill in the art to equivalent advantage. A step of the method is obtaining quantitative allele peak data at a first locus. A best fit mass ratio coefficient vector is solved using the quantitative allele peak data for allele combinations that can be contributed by the individuals. Residuals are calculated for the allele combinations. An allele combination is selected for the individuals at the first locus having the smallest residual. The smallest residual does not cluster with the second smallest residual. The allele combination selected comprises the genotype profiles of the individuals.

The invention also encompasses a method of analyzing quantitative allele peak data from a sample comprising DNA of more than one individual into a genotype profile for individuals in the sample. A step of the method is solving for a best fit mass ratio coefficient vector using allele peak data for allele combinations at a first locus that can be contributed by the individuals. Residuals are calculated for the allele combinations. An allele combination for the individuals at the first locus having the smallest residual. The smallest residual does not cluster with the second smallest residual. The allele combination selected comprises the genotype profiles of the individuals.

The invention further encompasses a method of remotely accessing a software application in a secure manner for resolving a mixture of DNA. The software application is hosted on a secure server. The software application is accessed from a client remotely via a network. The secure server and the client are protected via a firewall. The DNA mixture is transmitted to the secure server. The analysis results are received from the secure server at the client.

The invention further encompasses a method of generating genotype profiles for individuals who contribute DNA to a sample comprising DNA of more than one individual. A step of the method is obtaining quantitative allele peak data for a set of more than one loci in the sample. The quantitative allele peak data for each locus of the set of loci is separately assigned to allele combination that can comprise the genotype profiles of the individuals at each locus of the set of loci. A residual error and a mass ratio is separately computed for the allele combinations that can comprise the genotype profiles of the individuals at each locus of the set of loci. The allele combinations for each locus of the set of loci are selected. The mass ratio for the allele combinations selected is consistent. The residual error for the allele combinations selected is the smallest or the second smallest residual error and the allele combinations selected comprise the genotype profiles of the individuals who contribute DNA to the sample.

The invention also encompasses a method of analyzing least square deconvolution output data wherein the data include a mass ratio and residual for allele combinations at a first locus in a set of loci in a sample comprising DNA of two individuals. A step of the method is preliminarily selecting either a genotype combination for the two individuals having a residual that is smallest if the smallest residual does not cluster with the second smallest residual or preliminarily selecting more than one genotype combination for the two individuals if the more than one genotype combination comprises residuals that are the smallest and that cluster. The genotype combination for the two individuals from the preliminarily selected combination are determined where the genotype combination has a mass ratio consistent, with that of a second locus determined for the sample.

BRIEF DESCRIPTION OF THE DRAWINGS

FIGS. 16A and B show the output of web LSD for the simulated DNA mixture data with a mass ratio of 1:5. All possible genotype combinations are ranked at each locus according to the magnitudes of the fitting errors.

FIGS. 17A and B show the output of web LSD for the simulated DNA mixture data with a mass ratio of 1:2. All possible genotype combinations are ranked at each locus according to the magnitudes of the fitting errors.

FIGS. 18A and B show the output of web LSD for the simulated DNA mixture data with a mass ratio of 1:1. All possible genotype combinations are ranked at each locus according to the magnitudes of the fitting errors.

DETAILED DESCRIPTION OF THE INVENTION

To date, no direct, systematic, analytic, and quantitative method exists to resolve DNA mixture samples. The instant invention, based on quantitative allele peak data, provides the art with a method to resolve DNA mixture samples contributed by two individuals.

Least Square Deconvolution (LSD) is a novel method applying the least-square modeling approach to find the best-fit genotype combination to resolve mixed DNA samples comprising DNA of more than one person. Quantitative allele peak data are used in LSD because allele peak areas are theoretically proportional to the mass of the corresponding DNA alleles in a mixture and because the proportional relationship of allele peak areas is approximately preserved during PCR amplification. Other types of measurements with a known theoretical relationship to DNA allele mass in a sample and that approximately preserve this relationship in practice are equivalent. Examples of such equivalent types of measurement include allele peak height and optical density. The theoretical relationship does not have to be linear as long as it is known. The objective of LSD is to first find the best-fit genotype combination for the two contributors at loci where peak data are available, using least-square techniques and the measured allele peak data. Then, using the best fit mass ratio information for all loci processed, a composite genotype profile for each of the individual contributors can be formed that is compatible with the results of the least square analysis.

Figure 1:
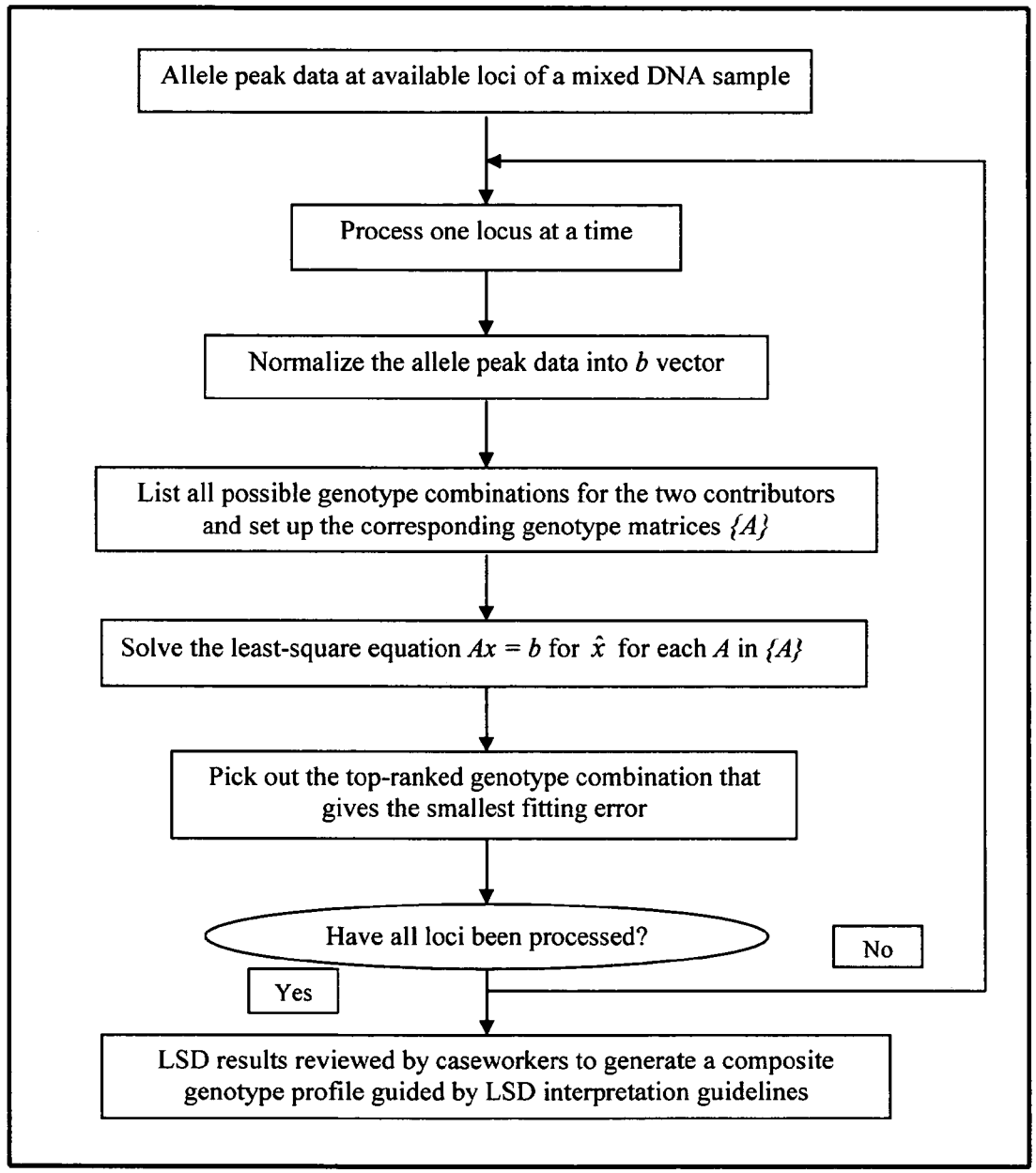
FIG. 1 is a flow diagram of the LSD method to resolve mixture DNA samples. For each locus, the best fitting genotypes for the two contributors and the approximate mass ratio can be obtained in one step.

The advantage of LSD compared to other quantitative approaches is its direct calculation of the best-fit genotype combination and the approximate mass ratio, without iterative searching for the optimal mass ratio. See (5) and (18). Some matrix calculations are involved in this method. FIG. 1 is a flow diagram of an embodiment of LSD. It is apparent from the diagram that LSD is applied at each locus independently of other loci, thus allowing each locus to be fitted with its own best-fit mass ratio, which can differ from the best-fit mass ratio arrived at other loci.

Compared with other approaches published in the literature, LSD is more efficient, simpler, more comprehensive, and gives true genotypes when the quantitative allele peak data and its theoretical relationship to allele mass approximately preserve the relative DNA mass proportionality. The advantage of LSD is its direct calculation of the best-fit genotype combination and the approximate mass ratio without iteration (5). Furthermore, LSD is applied to each locus independently of other loci, thus allowing each locus to be fitted independently with its own best-fit mass ratio, and the degree of confidence of fit to be independently assessed for each locus. From examining the relative errors of each fit at a locus, the degree of confidence can be separately assigned to the resulting best-fit genotype, locus by locus, allowing a composite profile to be assembled with a high degree of confidence containing only those loci whose LSD results are clear cut.

A locus refers to the position occupied by a segment of a specific sequence of base pairs along a gene sequence of DNA (2). Genes are differentiated by their specific sequences of base pairs at each locus. An allele refers to the specific gene sequence at a locus. At most two possible alleles can be present at one locus of a chromosome pair for each individual: one contributed by the paternal and the other contributed by the maternal source (8). If these two alleles are the same, the DNA profile is homozygous at that locus. If these two copies are different, the DNA profile is heterozygous at the locus (8). There are multiple alleles that can be contributed by either parent at each locus.

A genotype or DNA profile is the set of alleles that an individual has at a given locus. A genotype or DNA profile may also comprise the sets of alleles that an individual has at more than one locus. For example, a genotype or DNA profile may comprise the set of alleles at each of at least 2 loci, 3 loci, 4 loci, 5 loci, 7 loci, 9 loci, 11 loci, 13 loci, or 20 loci.

A DNA or genotype profile is developed from a nucleic acid sample, usually a DNA sample. Sources of nucleic acid include tissue, blood, semen, vaginal smears, sputum, nail scrapings, or saliva.

The DNA of interest can be prepared for analysis by the LSD method by amplification and subsequent separation. Amplification may be performed by any suitable procedures and by using any suitable apparatus available in the art. For example, enzymes can be used to perform an amplification reaction, such as Taq, Pfu, Klenow, Vent, Tth, or Deep Vent. Amplification may be performed under modified conditions that include "hot-start" conditions to prevent nonspecific priming. "Hot-start" amplification may be performed with a polymerase that has an antibody or other peptide tightly bound to it. The polymerase does not become available for amplification until a sufficiently high temperature is reached in the reaction. "Hot start" amplification may also be performed using a physical barrier that separates the primers from the DNA template in the amplification reaction until a temperature sufficiently high to break down the barrier has been reached. Barriers include wax, which does not melt until the temperature of the reaction exceeds the temperature at which the primers will not anneal nonspecifically to DNA.

The products of the amplification reaction are detected as different alleles present at a locus or loci. The alleles of at least one locus are amplified and detected after the amplification reaction. If desired, however, the alleles of multiple loci, e.g., two, three, four, five, six, ten, fifteen, twenty, twenty-five, or thirty, or more different loci may be detected after amplification. Sets of loci may include at least two, three, five, ten, fifteen, twenty, thirty, or fifty loci. Amplification of all of the alleles may be performed in a single amplification reaction or in a multiplex amplification reaction. Alternatively, the sample may be divided into several portions, each of which is amplified with primers that yield product for the alleles present at a single locus. Multiplex amplification is preferred.

The different alleles at a locus typically are detected because they differ in size. Alleles can differ in size due to the presence of repeated DNA units within loci. A repeated unit of DNA can be, e.g., a dinucleotide, trinucleotide, tetranucleotide, or pentanucleotide repeat. Short Tandem Repeats (STR) are DNA segments with repeat units of 2-6 bp in length (10). The repeated unit can be of a longer length that ranges from ten to one hundred base pairs. These are medium-length repeats and may be referred to as a Variant Number of Tandem Repeat (VNTR) (10). Repeat units of several hundred to several thousand base pairs may also be present in a locus. These are the long repeat units.

The number of repeated units at a locus also varies. The number of repeated units may be, for example, at least five, at least ten, at least fifteen, at least twenty, at least twenty-five, or at least fifty units. The effect of these repeated units of DNA is the presence of multiple types of alleles that an individual can possess at any given locus that can be detected by size (10).

Preferably, alleles that harbor different numbers of STR repeat units are detected. More than 8000 STRs (loci) scattered across the 23 pairs of human chromosomes have been collected in the Marshfield Medical Research Foundation in Marshfield, Wis. (10). Preferably, alleles at the 13 core loci used by the FBI Combined DNA Index System (CODIS): CSF1PO, FGA, TH01, TPOX, VWA, D3S1358, D5S818, D7S820, D8S1179, D13S317, D16S539, D18S51, and D21S11 (11), are detected.

It is also contemplated that amplification may be performed to detect an allele by amplifying microsatellite DNA repeats, DNA flanking Alu repeat sequences, or any other known polymorphic region of DNA that can be distinguished based on the size of different alleles.

Any method that separates amplification products based on size and any method that quantitates the amount of the allele present in the sample can be used to prepare the data required for analysis of genotype profiles in the method. The amplification products may be separated by electrophoresis in a gel or capillary, or mass spectrometry. The amount of each allele present may be determined flourometrically in a flourometer, or via ultraviolet spectrometry. For example, a Beckman Biomek® 2000 Liquid Handling System can be used to detect and quantitate alleles present for a locus in a sample. Optical density or optical signal can be used to detect the presence of an allele after gel or capillary electrophoresis.

Figure 2:
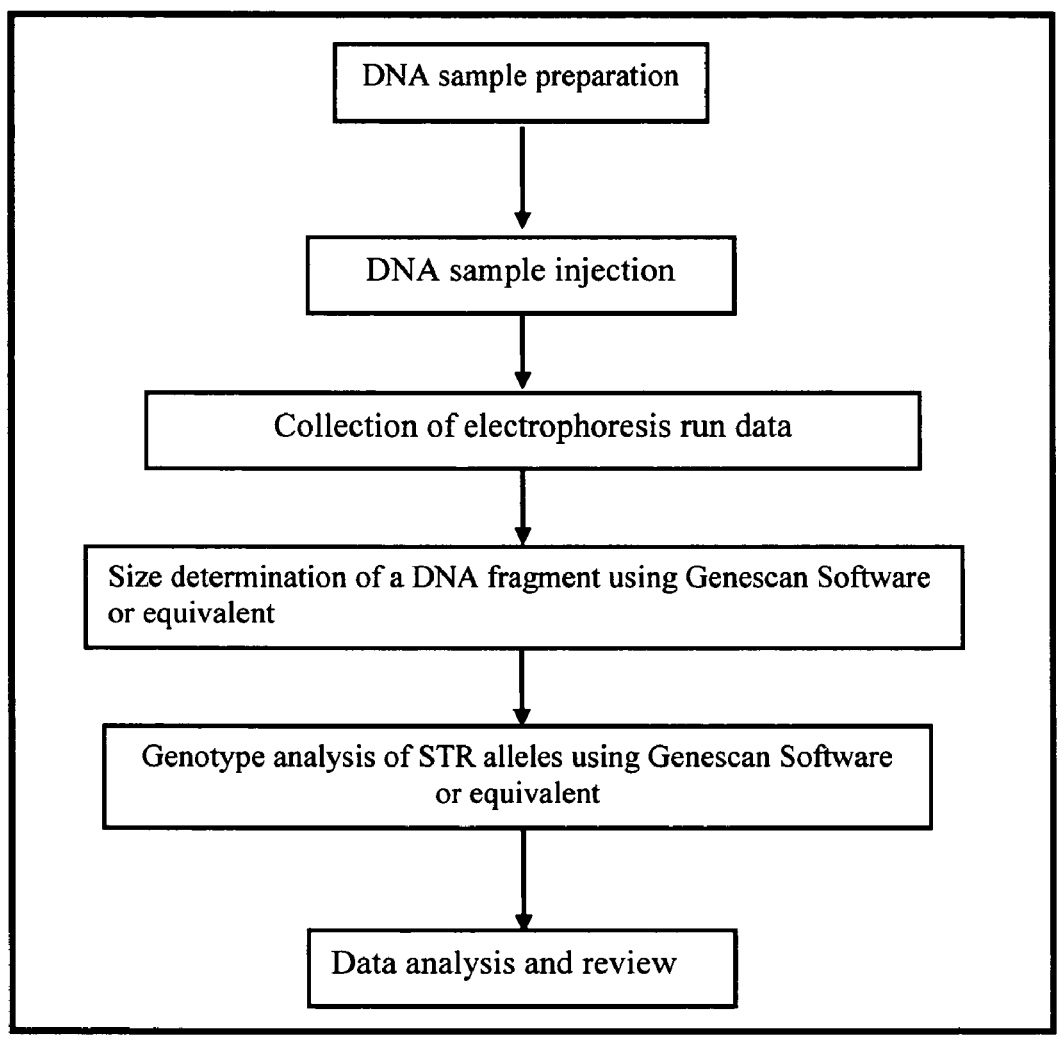
FIG. 2 is a flow diagram to show the typical processing steps of using the ABI 310 Genetic Analyzer to identify alleles present at each locus.
Figure 3:
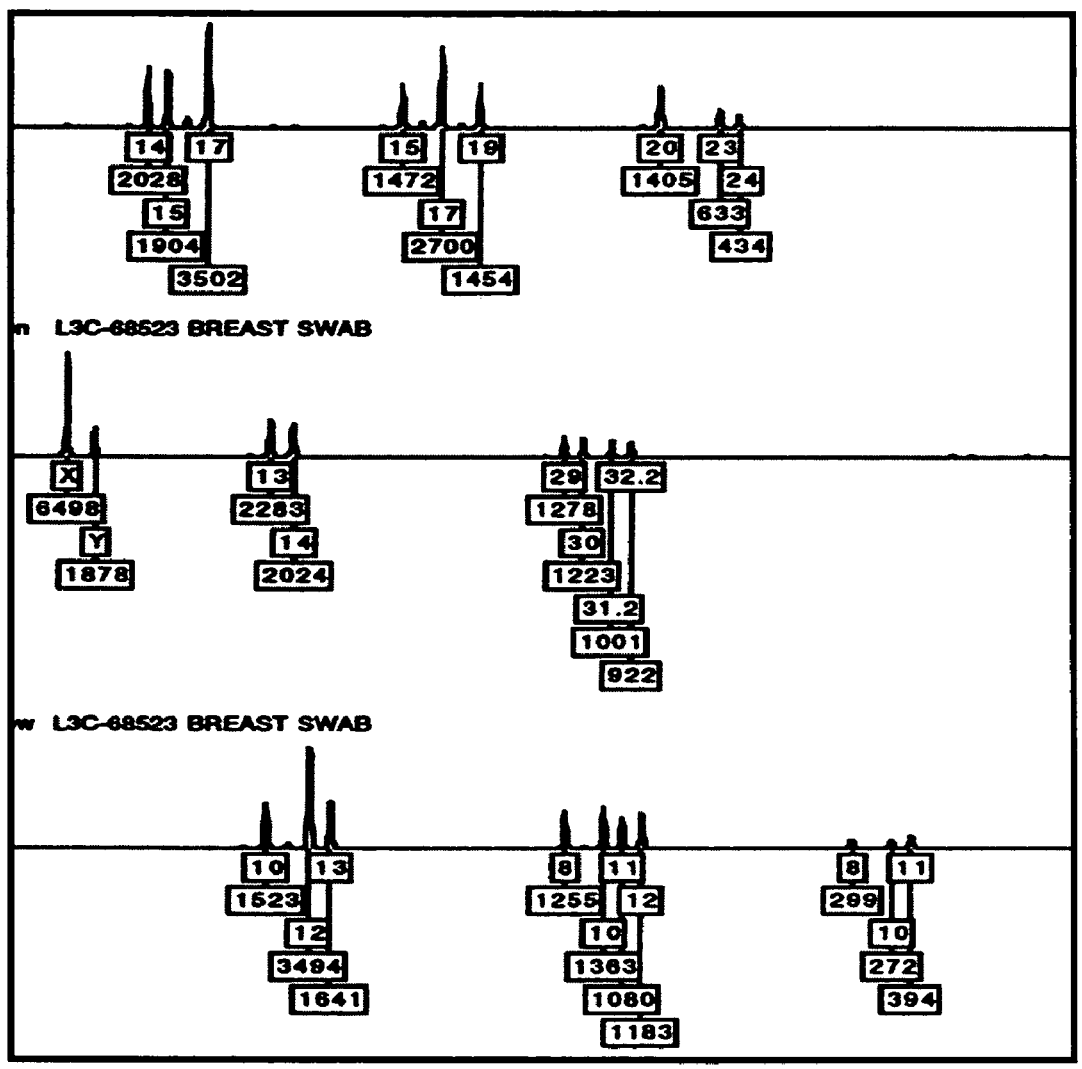
FIG. 3 shows the typical output of a DNA profile using the ABI 310 Genetic Analyzer. Each peak corresponds to one allele, and the peak area is proportional to the mass of the allele it represents.

Preferably, alleles are detected using an ABI Prism 310 Genetic Analyzer, or a HITACHI FMBIO II Fluorescence Imaging System (10). The ABI 310 Genetic Analyzer identifies alleles present at a locus, as outlined in FIG. 2, and provides a data output result, as shown in FIG. 3. One advantage of this instrument is that, in addition to sizing the detected allele signals, the related software can also display their peak heights and automatically calculate the area under each peak (10).

The HITACHI FMBIO II Fluorescence Imaging System uses gel electrophoresis instead of capillary electrophoresis to separate the alleles of a DNA sample (10). This system requires much more sample and a longer time to complete a separation. In this genetic analyzer, each allele corresponds to a specific band in a gel lane. The band size for each allele is compared with a well-calibrated allelic ladder to identify the corresponding allele (10).

If the amplification products are input into an apparatus that both separates and quantitates alleles for a locus in a sample, four different types of peaks can be obtained from these raw data: true or allele peaks, stutter peaks, artifact peaks, and pull up peaks.

True or allele peaks are peaks that indicate the presence of an allele at a locus. The most important characteristic of an allele peak is that the measured peak area or height is roughly proportional to the mass of the corresponding allele in the DNA sample (10). Preferably peak area is used.

Stutter peaks are peaks generated by the enzyme's slippage during the amplification process (12). In most cases, stutter peaks are located on the left side of the associated alleles, and the gene distance between the stutter peak and the associated allele peak is usually less than 4 bp (12). The height of the stutter peak is usually less than 15% of the height of the corresponding true allele peak (12).

Artifact peaks are peaks due to impurities in the DNA samples. Generally, the artifact peaks have one or more of the following three characteristics: (1) about 53% of them are less than 5% of the nearest allele peak's height (12), (2) some artifact peaks consist of multiple peaks, and the distances among them are always less than 1 bp (12), and (3) some artifact peaks are within 0.5 bp of an allelic ladder marker (12). If a peak satisfies any of the above three rules, the peak can be defined as an artifact peak, and the peak's effect can be eliminated.

A pull-up peak is a minor peak directly to the right of a 'true' allele peak. Usually, a pull-up peak is located on the right side of a 'true' allele peak with a distance less than ⅜ bp, and its height is less than 50% of the major peak.

Quantitative peak data of 'true' alleles are determined at a locus. These measurements may be the peak height or peak area of a signal detected by an instrument or procedure designed to quantify the presence of each allele. The peak height, peak area, and any other measurement that is related to the relative masses of each allele present in the original stain or sample are equivalent. Quantitative allele peak data will be referred to as "peak height," "peak area," or "quantitative allele peak data." Each of these terms is interchangeable.

The allele peaks or areas are calculated and analyzed using LSD. LSD then returns the "best-fit" genotype profiles for the two individuals that contribute to the sample. "Best-fit" refers to an assumption that the allele peak area/height is proportional to the relative mass proportion of the corresponding DNA allele in the mixture, the returned genotypes at the specified mass proportions would yield a set of allele peak areas/heights that is 'closest' to the measured set of allele areas/heights, in the least square sense (as measured by the Euclidean distance metric).

The genotype profile assigned to each individual by the LSD method can be verified by comparing the known genotype profile of one individual that contributed to the sample to that of one person developed by the LSD method. The known genotype profile may be obtained from an individual that is the victim of a crime.

A genotype profile obtained from the LSD method may also be matched to an individual to identify the individual as potentially having contributed to the sample. The genotype profile may be matched to the individual after obtaining a sample from the individual. The genotype profile may also be matched to an individual by comparing it to other genotype profiles in a database. The database may be any public or proprietary database that stores and/or matches genotype profiles. The database may be CODIS, which may be used to store genotype profiles in a national, state, or regional collection, and which may separate these profiles into disjoint parts, such as a convicted offenders database, a forensic DNA database, or a missing persons database.

Figure 4:
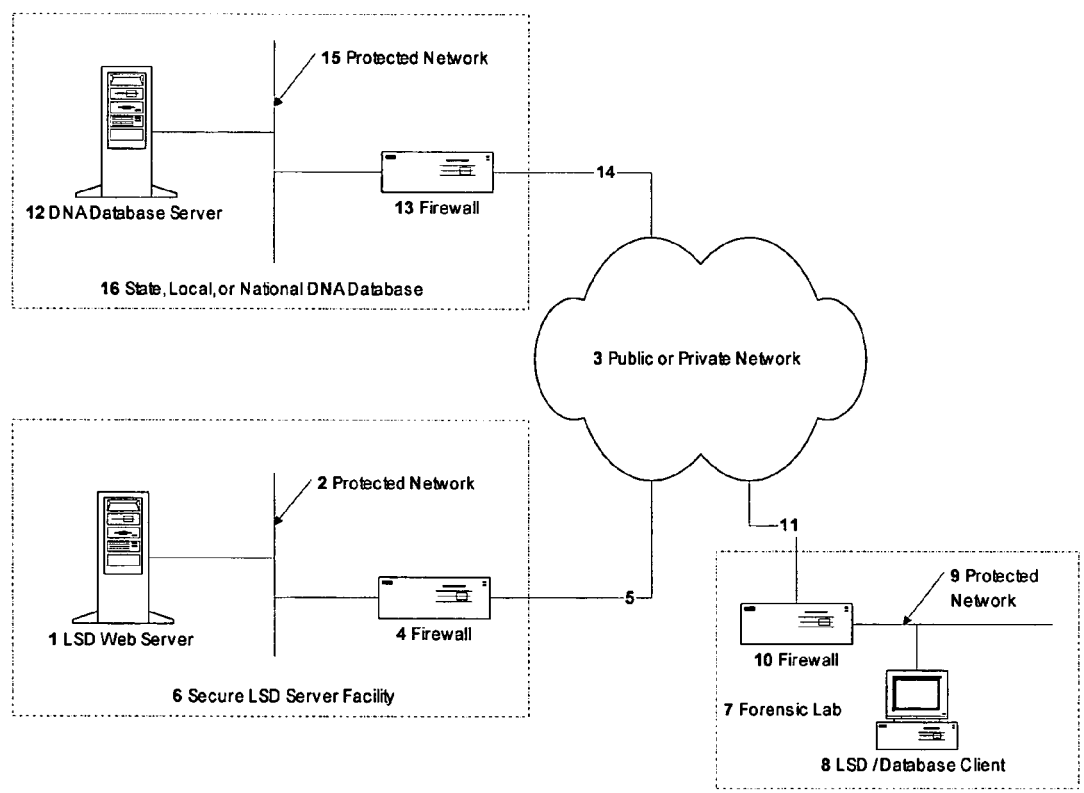
FIG. 4 shows a preferred embodiment of the invention in which LSD is implemented using software running under a secure web server.

A preferred embodiment of the invention is shown in FIG. 4. In this embodiment, LSD is implemented using software running under a secure web server 1 on a protected network 2 that is isolated from a public or private network 3 by a firewall 4. A remote user located at LSD/Database Client station 8 may access the LSD software at the web server 1 via the public or private network. The communication may be via the public switched telephone network (PSTN) preferably using known encryption algorithms for confidential data but is preferably via a private network and encrypted. The firewall 4 allows communications with the secure web server 1 using an encrypted communications protocol such as the Hypertext Transfer Protocol (HTTP) over a Secure Sockets Layer (SSL). The firewall 4 connects the protected network 2 to the public or private network 3 using either an Internet service provider (ISP), leased, or owned telecommunications equipment/circuits 5 having appropriate bandwidth capability (although the data may be suitably compressed via known compression algorithms and transmitted over lower bandwidth facilities). The connection to the firewall 4 and all connections and equipment collocated with the protected network 2 are housed in a secure server facility 6 that provides LSD services to a community of clients located at forensic laboratories 7 or other organizations. Location 7, 8, 9 is shown by way of example only and is no way intended to be limited to forensic laboratory locations.

A client 8 located at a forensic laboratory or other organization may use the public or private network 3 to gain access to LSD services offered by the secure server facility 6. Preferably, the client 8 is connected to a protected network 9 which connects to the public or private network 3 through a firewall 10, and the firewall 10, the protected network 9, and all equipment connected to the protected network 9, such as the LSD/Database Client 8, are housed in a secure client facility such as a forensic laboratory 7 (or other secure facility). The firewall 10 located at the forensic laboratory 7 connects the protected network 9 to the public or private network 3 using either an ISP, leased, or owned telecommunications equipment/circuits 11 having similar bandwidth considerations as described above for equipment/circuits 5.

The client 8 may make requests to analyze data derived from DNA mixtures on the secure LSD web server 1 by accessing the secure web server 1, transmitting DNA mixture data to the secure web server, and receiving analysis results. These results may then be interpreted using mixture interpretation guidelines to obtain one or more DNA profiles that may be associated with a suspect to a crime.

Optionally, the LSD/Database Client 8 may access a local laboratory, state, or national DNA database 12 to search for matches to the one or more DNA profiles formed using the results of the LSD analysis. The DNA database 12 may be located in a separate secure facility at the state, local, or national level and is preferentially protected by a firewall 13. The firewall 13 is connected to the public or private network using either an ISP, leased, or owned telecommunications equipment/circuits 14, and preferentially allows communications with a DNA database server 12 using only an encrypted communications protocol such as HTTP over SSL. The firewall 13 and DNA database server 12 are connected to a protected network 15. The connections to the firewall 13 and all connections and equipment collocated with the protected network 15 are housed in a secure server facility 16 that provides DNA database services to a community of clients located at forensic laboratories 7 or other organizations.

Nothing shown in FIG. 4 or described above should be taken to restrict the domain of the invention. For example, the DNA database server and the secure LSD server may be connected through firewalls to two separate and isolated public or private networks, requiring a separate client and protected network located at a forensic laboratory in order to communicate with each server. This is the case at present with the FBI's National DNA Index System (NDIS), which is connected to state and local facilities through the FBI-owned and operated Criminal Justice Information System's Wide Area Network (CJIS-WAN), and with the current implementation of the secure LSD server. This server is located on a protected network within The University of Tennessee's Laboratory for Information Technologies (LIT) and is connected through a firewall owned and operated by LIT to the university's campus network and thence to the public Internet. In this case, the functionality remains the same, except that an investigator or analyst transfers results obtained by a client from the secure LSD server to a client computer of the FBI's NDIS facilities in order to perform a search on the national DNA database.

The invention is not restricted to operation on protected computers and networks, nor is it restricted to require security of communications using encryption and secure authentication protocols. However, these measures are usually necessitated by the privacy laws of the United States and other countries. In a similar manner, it is not required that the LSD software, LSD/Database Client, and DNA database software operate on separate and communicating computers. They may in fact all be installed and operated on a single computer in some applications, or on two computers. There may also be multiple instances of the DNA database software running on several computers. The realities of multiple jurisdictions and multiple ownership of and responsibility for controlled access to data that are considered sensitive usually necessitates the use of multiple computers under the control of independent but cooperating agencies.

EXAMPLES

Example 1

Figure 5:
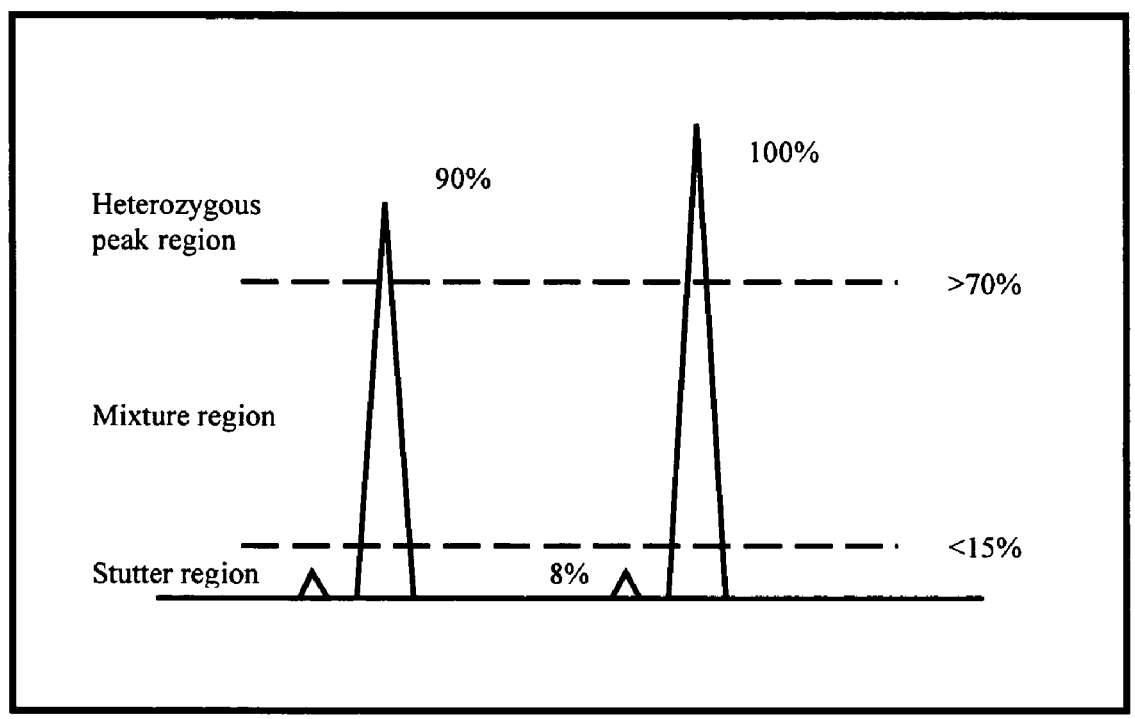
FIG. 5 is an illustration of allele peaks of a typical heterozygous locus from a single source.

Identification of DNA Mixtures with More than One Contributor and Determination of the Number of Contributors in the DNA Mixtures According to studies reported in the literature (10), if only one person contributes to a DNA sample, then no more than two alleles will be detected at a locus. (There have been cases where a DNA sample from one person does cause detection of three alleles at a locus, but these cases are extremely rare.) Therefore, a DNA/STR sample is highly likely to be a mixture if more than two alleles are consistently present at multiple loci. For a locus with two heterozygous alleles from a single contributor, if the higher peak is set as 100%, the heterozygous companion allele, due to the co-amplification of the two alleles, usually has a peak area or peak height greater than 70% of the higher allele (10). A severe peak-height imbalance between any two heterozygous alleles at a locus strongly suggests that the DNA sample being tested is a mixture. FIG. 5 is an illustration of a typical heterozygote DNA/STR profile from a single contributor. Note that only two 'true' alleles are present; the two minor peaks are considered to be stutter peaks (10), an artifact of the DNA amplification procedure.

If a sample comes from only one person, usually no more than two true alleles can be detected at one locus. If there are still more than two peaks appearing at several loci, even after eliminating the effects of the stutter peaks, the pull-up peaks, and the artifact peaks, it can be concluded that the sample contains a mixture from at least two separate contributors.

Because usually no more than two alleles can be detected at one locus for a one-person DNA sample, the maximum number of alleles that typically can be detected at one locus for a two-person mixed DNA/STR profile is four. Five or more alleles present at several loci would be strongly indicative of three or more contributors (3). In the national CODIS DNA database in 2002, approximately 9% of DNA profiles are mixture samples, but the DNA analysts spend 90% of their efforts and time trying to interpret them (13). In most forensic cases, especially in rape cases, a great number of mixed DNA samples are contributed by two individuals, although three-people mixtures are also encountered occasionally (3).

Figure 6:
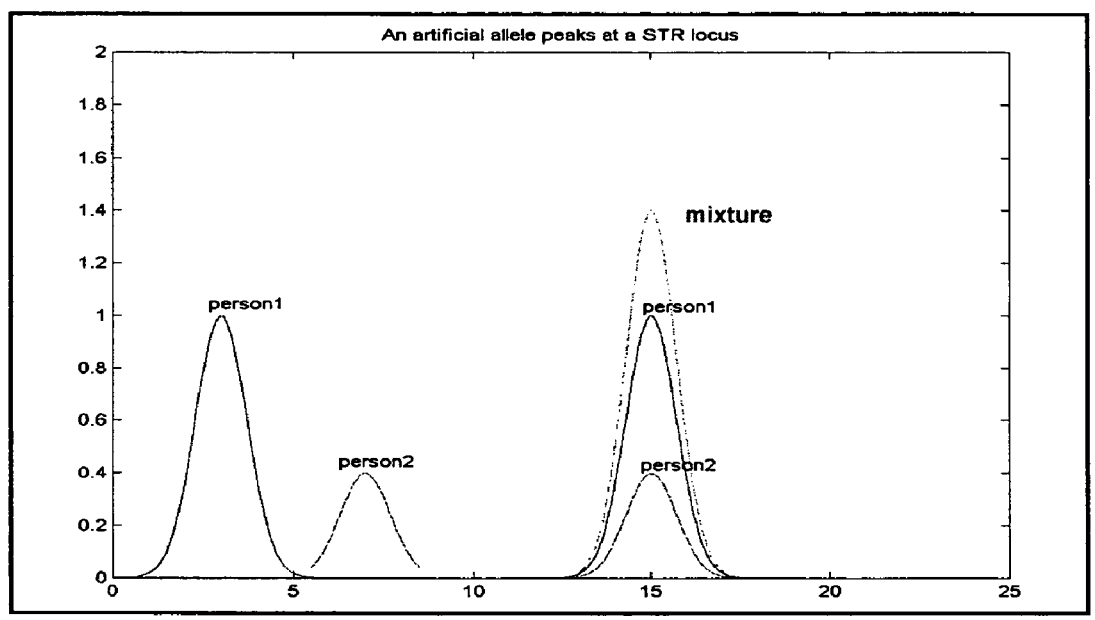
FIG. 6 shows simulated superimposed allele peaks at one locus for a mixed DNA profile, with the contributors' genotypes of [3, 15] and [7,15], mixed at a mass ratio of 1:0.4 respectively. Note that allele 15 is the shared allele.

Some alleles may be shared by each of the contributors to a DNA mixture. Thus, the peaks in the mixture sample can be regarded as the superposition, or sum of the two individuals' allele peaks. These important characteristics allow one to resolve the DNA mixture profile by using the allele peak information. FIG. 6 shows an artificial example of allele peaks contributed by two people. Note that only two heterozygous alleles associated with the same contributor have equal peak areas (in the ideal case), and allele 15 is shared between the two individuals. In addition, the peak area of alleles from person 2 is about 40% of that from person 1.

Example 2

Mathematical Principles for Solving the Linear Least-Square Solution to Data Fitting To perform LSD, multivariable linear equations (Ax=b) are solved for data fitting. Most overdetermined multivariable linear equations do not have exact solutions because they are inconsistent with each other. In those cases, the least-square approach can be used to obtain a best-fit solution (16), which yields a fitted $\hat{b}$ that is closest to the given b.

Example 2A

Introduction to the Least-Square Approach

Let A be an m by n (m>n) matrix and b be a column vector composed of m elements. For a linear equation of Ax=b, an exact solution for this equation, x, can be obtained only when b is in the column space of A. (The vector b can be expressed as a linear combination of the columns of the matrix, A. The elements in the vector, x, determine the linear combination.) The multiplication of A and x can be viewed as:

$$Ax = b \Rightarrow \begin{bmatrix} | & | & | & | \\ | & | & | & | \\ a_1 & a_2 & \ldots & a_n \\ | & | & | & | \\ | & | & | & | \end{bmatrix} \begin{bmatrix} x_1 \\ \vdots \\ x_n \end{bmatrix} =$$

$$\begin{bmatrix} b_1 \\ \vdots \\ b_m \end{bmatrix} \Rightarrow x_1 \begin{bmatrix} | \\ | \\ a_1 \\ | \\ | \end{bmatrix} + x_2 \begin{bmatrix} | \\ | \\ a_2 \\ | \\ | \end{bmatrix} + \ldots + x_n \begin{bmatrix} | \\ | \\ a_n \\ | \\ | \end{bmatrix} = \begin{bmatrix} b_1 \\ \vdots \\ b_m \end{bmatrix}.$$

For example: if A is $$\begin{bmatrix} 1 & 2 \\ 6 & 5 \\ 3 & 4 \end{bmatrix},$$

and b is $$\begin{bmatrix} 8 \\ 27 \\ 18 \end{bmatrix},$$

the linear equation:

$$Ax = b \left( \begin{bmatrix} 1 & 2 \\ 6 & 5 \\ 3 & 4 \end{bmatrix} x = \begin{bmatrix} 8 \\ 27 \\ 18 \end{bmatrix} \right)$$

has an exact solution x, because b can be expressed as a linear combination of the columns of A as shown:

$$\begin{bmatrix} 1 \\ 6 \\ 3 \end{bmatrix} 2 + \begin{bmatrix} 2 \\ 5 \\ 4 \end{bmatrix} 3 = \begin{bmatrix} 2+6 \\ 12+15 \\ 6+12 \end{bmatrix} = \begin{bmatrix} 8 \\ 27 \\ 18 \end{bmatrix} \Rightarrow \begin{cases} x_1 = 2 \\ x_2 = 3 \end{cases}.$$

Therefore, the solution for this multivariable linear equation is $$x = \begin{bmatrix} 2 \\ 3 \end{bmatrix},$$

where A and b are given as stated.

Figure 7:
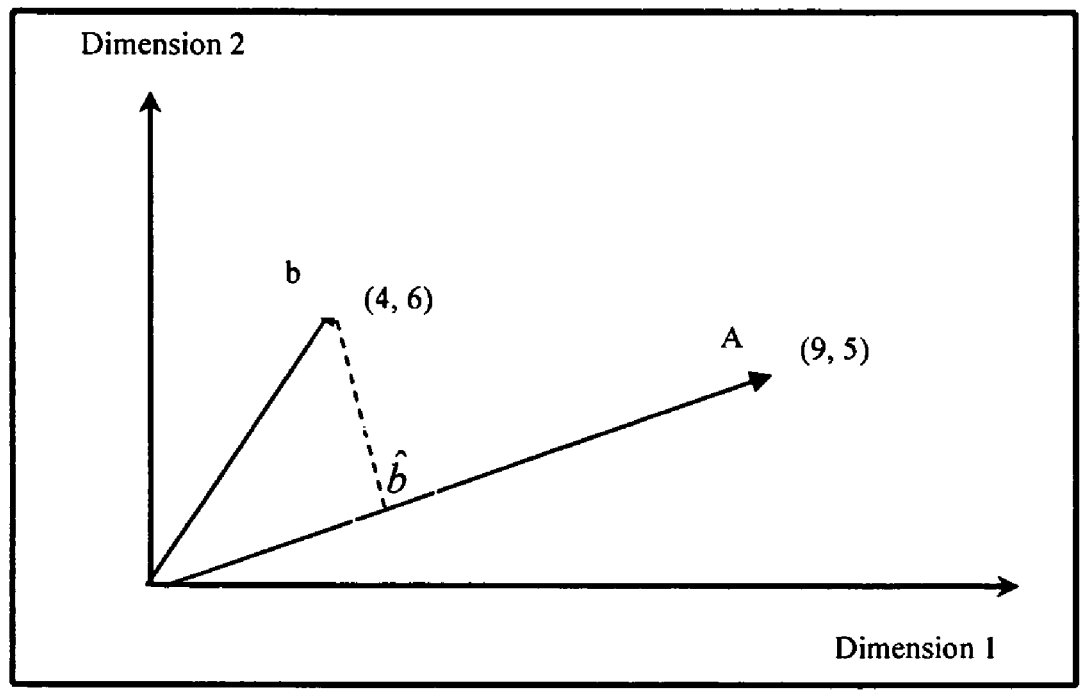
FIG. 7 shows the projection of b vector (4,6) onto A vector (9,5). The error vector (b−b̂) is perpendicular to the A vector and gives the shortest distance from b to A.

When b cannot be expressed as a linear combination of the columns of A, as shown in the example described below, then no solution, x, would exist that exactly satisfies the equation Ax=b. Such system is termed inconsistent and has no solution (16). For example, the simultaneous equation:

$$\begin{cases} 9x = b_1 \\ 5x = b_2 \end{cases},$$

which can also be written as:

$$Ax = b \left( A = \begin{bmatrix} 9 \\ 5 \end{bmatrix} \right),$$

can be solved with exact solution only when $b_1$ and $b_2$ are in the ratio of 9:5, which means that the exact solution x exists only when b is on the same line as the vector A (such as $$\begin{bmatrix} 9 \\ 5 \end{bmatrix}$$

drawn from the origin. If b is $$\begin{bmatrix} 4 \\ 6 \end{bmatrix},$$

it is clear that no exact solution x can fit both of these two equations simultaneously. Seemingly unsolvable equations such as this are often encountered in practice from modeling experimental results, and must still be solved. In this case, an 'approximate' solution is to be sought, such that A times the approximate solution $\hat{x}$, would give a $\hat{b}$ that is 'closest' to the given b. For the example given above, from FIG. 7, one can see that the distance between the given b vector and $\hat{b}$, the projection of b vector onto the A vector is the shortest among all the routes from b to the line A. This implies that the error vector (b−$\hat{b}$) for the optimal $\hat{b}$ must be perpendicular to the A vector. Since A$\hat{x}$=$\hat{b}$, we require the inner product between the A vector and the error vector to be 0: $A^T(b-\hat{b})=A^T(b-A\hat{x})=0 \Rightarrow A^T A\hat{x}=A^T b$.

The transpose of the matrix A is denoted by $A^T$. The solution is given by $\hat{x}=(A^T A)^{-1}A^T b$ if $(A^T A)^{-1}$ exists. If not, the pseudoinverse of A must be used. In a single variable case, $\hat{x}$ is given by $\hat{x}=A^T b/(A^T A)$ because $A^T A$ is a scalar. For the example in FIG. 7, the $\hat{x}$ is given by:

$$\hat{x} = A^T b/(A^T A) = \frac{9*b_1 + 5*b_2}{9*9 + 5*5}.$$

The corresponding $\hat{b}$ is given by:

$$\hat{b} = \begin{bmatrix} 9 \\ 5 \end{bmatrix}\hat{x}.$$

Another approach to arrive at the optimum $\hat{x}$ minimizes the sum of the squares of the fitting error between the calculated $\hat{b}$ and the measured data b using calculus. For the example above, the error can be expressed as:

$$E^2=(9\hat{x}-b_1)^2+(5\hat{x}-b_2)^2.$$

The minimum error $E^2$ would be zero, if an x can be found to fit both of these two equations exactly. In most cases, the vectors b and a are not in the same line, and the value of $E^2$ would not be equal to zero. $E^2$ is expressed as a function of $\hat{x}$, and the minimum value of $E^2$ can be obtained by taking the derivative of $E^2$ with respect to $\hat{x}$, i.e. $d(E^2)/d\hat{x}$, and setting it to 0, followed by solving for $\hat{x}$. $\hat{x}$ is found to be:

$$\hat{x} = \frac{9*b_1 + 5*b_2}{9*9 + 5*5}.$$

The $\hat{x}$ that minimizes $E^2$ is referred to as the least-square solution to the inconsistent system Ax=b. The solution $\hat{x}$, arrived by the two approaches, is exactly the same.

Example 2B

Figure 8:
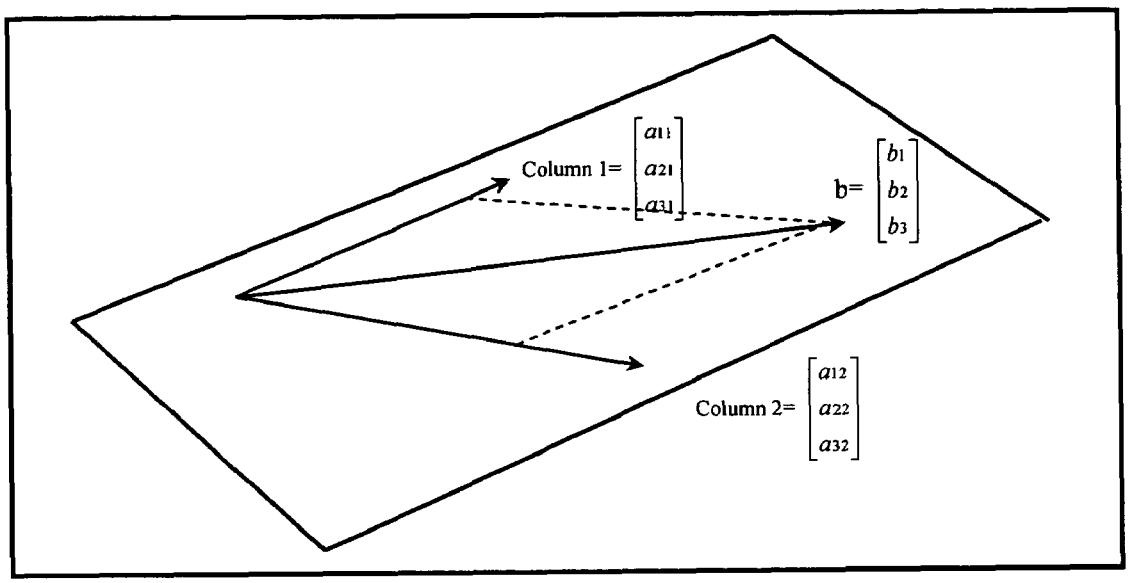
FIG. 8 shows vector b is in the column space of A (3×2 matrix). Therefore, b can be expressed as a linear combination of columns of A.
Figure 9:
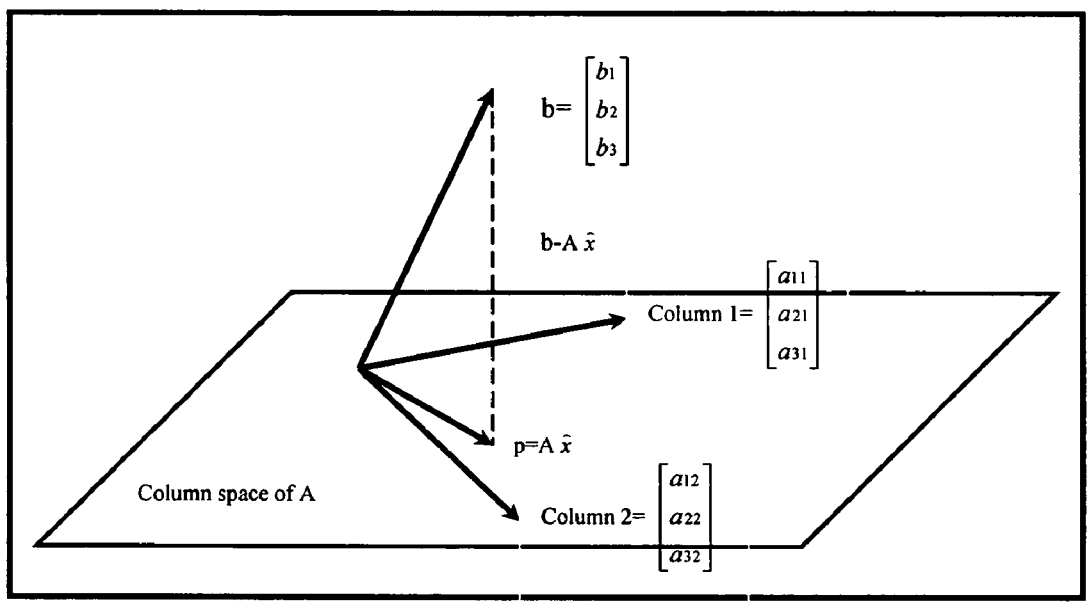
FIG. 9 shows the projection of b vector onto the column space of a 3 by 2 matrix A. p is the projection of b vector onto the column space of A.

Multivariable Least-Square Solution to Inconsistent Linear System of Equations, with More Equations than Unknowns The multivariable system of equations, Ax=b, which has n variables and m observations, is solvable only when the vector b is a linear combination of the columns of A. FIG. 8 shows an example where the vector b is in the column space of A (a 3 by 2 matrix). In this case, the multivariable equations Ax=b is solvable. When n is less than m, it is very possible that Ax=b is inconsistent, which means that the given vector b does not lie in the space spanned by the columns of A, as shown in FIG. 9. In this case, an exact solution x, to the multivariable systems of equations Ax b, does not exist. However, an approximate solution can be obtained by choosing $\hat{x}$, such that A$\hat{x}$ comes 'closest' to the given vector b. In other words, $\hat{x}$ would minimize the square of the distance between the given b vector (or, equivalently, the distance), and the fitted point of (A$\hat{x}$), which is expressed as $$E^2=\|A\hat{x}-b\|^2.$$

Here, $\|.\|$ denotes the norm of a vector (or the magnitude of a vector), and can be defined as the square root of the sum of squares of the elements in a vector. Other equivalent definitions of the norm of a vector are possible and can be used. Also, the same solution is obtained if the square is omitted. This least-square approach is widely accepted as an applicable way for multivariable data fitting (16). From FIG. 9, one can see that the perpendicular distance between the vectors b and p, which is the projection of b onto the column space of A, is the minimum of all distances from b to the plane spanned by the two columns of A. In this case, the result of A$\hat{x}$ gives the projection of the vector b onto the column space of A, or the point p, which is indeed closest to b of all points on the plane. The vector (b−A$\hat{x}$) is the error vector e and is perpendicular to the column space of A, This implies:

$$A^T(b-A\hat{x})=0.$$

So, the least-square solution, $\hat{x}$, of Ax=b is one that satisfies the so-called 'normal equation':

$$A^T A\hat{x}=A^T b.$$

and the least-square solution for such equation is given by:

$$\hat{x}=(A^T A)^{-1}A^T b.$$

If the columns of A are linearly dependent and $(A^T A)$ is not invertible, then the best-fit $\hat{x}$ is to be computed by the pseudoinverse of x, or $x^+$:

$$\hat{x}=A^+ b,$$

where $A^+$ represents the pseudoinverse of the matrix A, which is preferably computed using the singular-value-decomposition (SVD) of A (16):

$$A=U\Sigma V^T,$$

where U (m by m matrix) and V (n by n matrix) are orthogonal matrices, and $\Sigma$ (m by n matrix) is a diagonal matrix with non-negative diagonal elements arranged in a decreasing order. The diagonal elements of $\Sigma$, $\sigma_1$, $\sigma_2$, ... $\sigma_n$, are called the singular values of A, and the rank of A is determined by the number of nonzero singular values. The pseudoinverse of A is computed as:

$$A^+=V\Sigma^+ U^T,$$

where $\Sigma^+$ is an n by m matrix with $1/\sigma_1$, $1/\sigma_2$, ... $1/\sigma_r$ on its main diagonal, where r denotes the number of nonzero singular values; the remaining diagonal elements of $\Sigma^+$, corresponding to those zero singular values in $\Sigma$, are also zero. This is one of the hallmarks of the pseudoinverse which enables the least-square solution of an inconsistent system of linear equation to be obtained in one direct step.

If the columns of A are linearly independent, we can also calculate the least-square solution as:

$$\hat{x}=(A^TA)^{-1}A^Tb=(V\Sigma^TV^T)^{-1}V\Sigma^TU^Tb=$$
$$V(\Sigma^T\Sigma)^{-1}V^1V\Sigma^TU^Tb=V\Sigma^+U^Tb=A^+b.$$

If A is a square and full-rank matrix, implying A is invertible, then the equation Ax=b is consistent with the exact solution, x, which is given by:

$$x=A^{-1}b.$$

In this case, U, V, and $\Sigma$ are all square matrices, and $\Sigma$ is invertible, and the inverse of A can be calculated as:

$$A^{-1}=(U\Sigma V^T)^{-1}=V\Sigma^1 U^T,$$

which is exactly the same as $A^+$. Therefore, for all multivariable systems of equations Ax=b, the least-square solution, $\hat{x}$, can always be calculated from $\hat{x}=A^+b$ using the SVD.

Example 3

Principles for Using the Least Square Approach (LSD) to Resolve Mixed DNA Samples into Each Contributor's Genotype.

Example 3A

Represent all Possible Genotype Combinations at Each Locus with Matrices.

The allele peak data of a DNA mixture sample, when available, usually includes the allele peak information from 6 to 18 loci. One locus is to be analyzed at a time. For each locus, the number of alleles can be determined by observing all the true peaks in the electropherogram at this locus (3). According to the number of true alleles detected, all possible allele assignment patterns for the two contributors are to be first enumerated. For each possible allele combination pattern for the two contributors, a matrix of coefficients with two columns, one for each person, can be formed. This matrix is referred to as the 'A' matrix, such as those shown in Table 1. Each column of A represents the genotype of one contributor at this locus. Each element in the matrix A is either 0, 1, or 2, representing the absence or presence of the corresponding allele. A '2' stands for the homozygote allele indicating that the contributor has two copies of this allele at the specified locus. The number of rows of the matrix A corresponds to the number of alleles observed at this locus in the mixture sample.

TABLE 1

| | Genotype Combination | | | Pseudoinverse of the |
|---|---|---|---|---|
| Case | Person 1 | Person 2 | Matrix (A) | Matrix ($A^+$) |
| 1 | A, A | B, C | $\begin{bmatrix} 2 & 0 \\ 0 & 1 \\ 0 & 1 \end{bmatrix}$ | $\frac{1}{2}\begin{bmatrix} 1 & 0 & 0 \\ 0 & 1 & 1 \end{bmatrix}$ |
| 2 | B, B | A, C | $\begin{bmatrix} 0 & 1 \\ 2 & 0 \\ 0 & 1 \end{bmatrix}$ | $\frac{1}{2}\begin{bmatrix} 0 & 1 & 0 \\ 1 & 0 & 1 \end{bmatrix}$ |
| 3 | C, C | A, B | $\begin{bmatrix} 0 & 1 \\ 0 & 0 \\ 2 & 1 \end{bmatrix}$ | $\frac{1}{2}\begin{bmatrix} 0 & 0 & 1 \\ 1 & 1 & 0 \end{bmatrix}$ |

TABLE 1-continued

| | Genotype Combination | | | Pseudoinverse of the |
|---|---|---|---|---|
| Case | Person 1 | Person 2 | Matrix (A) | Matrix ($A^+$) |
| 4 | A, B | B, C | $\begin{bmatrix} 1 & 0 \\ 1 & 1 \\ 0 & 1 \end{bmatrix}$ | $\frac{1}{3}\begin{bmatrix} 2 & 1 & -1 \\ -1 & 1 & 2 \end{bmatrix}$ |
| 5 | A, B | A, C | $\begin{bmatrix} 1 & 1 \\ 1 & 0 \\ 0 & 1 \end{bmatrix}$ | $\frac{1}{3}\begin{bmatrix} 1 & 2 & -1 \\ 1 & -1 & 2 \end{bmatrix}$ |
| 6 | A, C | B, C | $\begin{bmatrix} 1 & 0 \\ 0 & 1 \\ 1 & 1 \end{bmatrix}$ | $\frac{1}{3}\begin{bmatrix} 2 & -1 & 1 \\ -1 & 2 & 1 \end{bmatrix}$ |

All possible genotype combinations and their corresponding matrices at a three-allele locus for the two contributors. The three alleles are designated as {A, B, C}. The numbers {0, 1, 2} in the matrix A represents 0, 1, or 2 copies of the corresponding allele it represents.

For a DNA mixture contributed by two people, the number of alleles that can be present at one locus is between one and four. If only one allele is present at a certain locus, then undoubtedly both contributors are homozygous with this allele at this locus. In Tables 1, 2, and 3, all possible genotype combinations for the two source contributors and their corresponding 'A' matrices are listed for the cases of 3, 2, and 4 alleles present at a locus, respectively. The last column in each of these three tables lists the pseudoinverse matrix of the corresponding genotype matrix 'A'. The pseudoinverse matrix will be used to compute directly the best-fit mass coefficients during the least-square fitting step.

TABLE 2

| | Genotype Combination | | | Pseudoinverse of |
|---|---|---|---|---|
| Case | Person 1 | Person 2 | Matrix (A) | the Matrix ($A^+$) |
| 1 | A, A | B, B | $\begin{bmatrix} 2 & 0 \\ 0 & 2 \end{bmatrix}$ | $\frac{1}{2}\begin{bmatrix} 1 & 0 \\ 0 & 1 \end{bmatrix}$ |
| 2 | A, B | A, A | $\begin{bmatrix} 1 & 2 \\ 1 & 0 \end{bmatrix}$ | $\frac{1}{2}\begin{bmatrix} 0 & 2 \\ 1 & -1 \end{bmatrix}$ |
| 3 | A, B | B, B | $\begin{bmatrix} 1 & 0 \\ 1 & 2 \end{bmatrix}$ | $\frac{1}{2}\begin{bmatrix} 2 & 0 \\ -1 & 1 \end{bmatrix}$ |
| 4 | A, B | A, B | $\begin{bmatrix} 1 & 1 \\ 1 & 1 \end{bmatrix}$ | $\frac{1}{4}\begin{bmatrix} 1 & 1 \\ 1 & 1 \end{bmatrix}$ |

All possible genotype combinations and their corresponding matrices at a two-allele locus for the two contributors. The two alleles are designated as {A, B}. The numbers {0, 1, 2} in the matrix A represents 0, 1, or 2 copies of the corresponding allele it represents.

TABLE 3

| Case | Genotype Combination | | Matrix (A) | Pseudoinverse of the Matrix (A$^+$) |
|------|----------|----------|------------|-----------------------------|
|      | Person 1 | Person 2 |            |                             |
| 1    | A, B     | C, D     | $\begin{bmatrix} 1 & 0 \\ 1 & 0 \\ 0 & 1 \\ 0 & 1 \end{bmatrix}$ | $\frac{1}{2}\begin{bmatrix} 1 & 1 & 0 & 0 \\ 0 & 0 & 1 & 1 \end{bmatrix}$ |
| 2    | A, C     | B, D     | $\begin{bmatrix} 1 & 0 \\ 0 & 1 \\ 1 & 0 \\ 0 & 1 \end{bmatrix}$ | $\frac{1}{2}\begin{bmatrix} 1 & 0 & 1 & 0 \\ 0 & 1 & 0 & 1 \end{bmatrix}$ |
| 3    | A, D     | B, C     | $\begin{bmatrix} 1 & 0 \\ 0 & 1 \\ 0 & 1 \\ 1 & 0 \end{bmatrix}$ | $\frac{1}{2}\begin{bmatrix} 1 & 0 & 0 & 1 \\ 0 & 1 & 1 & 0 \end{bmatrix}$ |

All possible genotype combinations and their corresponding matrices at a four-allele locus for the two contributors. The four alleles are designated as {A, B, C, D}. The numbers {0, 1} in the matrix A represent 0 or 1 copy of the corresponding allele it represents.

A normalized vector 'b' is to be generated from the measured allele peak area data, such that the smallest allele peak area in the vector is normalized to 1, and those of all other alleles in the same locus are ratioed to it. The number of elements in the vector 'b' reflects the number of alleles present at this locus. For example, if the peak area measured at one locus is [3454, 4588, 8766], then the corresponding normalized b vector would be:

$$b = \begin{bmatrix} 3454/3454 \\ 4588/3454 \\ 8766/3454 \end{bmatrix} = \begin{bmatrix} 1 \\ 1.33 \\ 2.54 \end{bmatrix}.$$

Other normalizations such that the smallest peak ratios are not equal to one are possible and equivalent.

Example 3B

Using the Least-Square Approach to Calculate the Best-Fit Mass Coefficients and the Residuals at Each Locus The method used to calculate the best-fit mass coefficients and the residuals at each locus is presented in this section. The allele peak areas at each locus of a mixed DNA/STR sample are a superposition of both contributors' allele peaks, weighted by their corresponding mass proportions. For example, for a locus with three alleles, the relationship between the genotypes of the two contributors and the allele peak areas measured can be expressed as a linear equation:

$$\begin{bmatrix} 1 & 0 \\ 0 & 1 \\ 1 & 1 \end{bmatrix} * \begin{bmatrix} Mass1 \\ Mass2 \end{bmatrix} = Mass1 \begin{bmatrix} 1 \\ 0 \\ 1 \end{bmatrix} + Mass2 \begin{bmatrix} 0 \\ 1 \\ 1 \end{bmatrix}$$

$$= \alpha \begin{bmatrix} Allele1 \text{ peak data} \\ Allele2 \text{ peak data} \\ Allele3 \text{ peak data} \end{bmatrix}$$

$$A * x = b$$

where '$\alpha$' is a proportionality constant. For the locus with three or four alleles, A is a three by two, or four by two matrix respectively, and the multivariable linear equation of Ax=b would generally be inconsistent, with more equations than unknowns and no exact solution would exist, meaning no solution 'x' can be found such that Ax would equal to b exactly.

However, the least-square solution of Ax=b can be found, where $x_{ls}$ is a two-element vector composed of the relative mass coefficients for the two contributors to the DNA mixture, such that A times $x_{ls}$ would be 'closest' to the given vector 'b', of all possible x vectors. Computationally, the least-square solution, $\hat{x}$ to the inconsistent Ax=b, is given by $\hat{x}=A^+b$, where $A^+$ denotes the pseudoinverse of A (16). The solution $\hat{x}$ is such that $(A\hat{x})$ will give a fitted allele peak vector $\hat{b}$, which is not equal to b exactly, but would be 'closest' to 'b'. The difference between 'b' and '$\hat{b}$' is called the residual vector. The magnitude of the residual, representing how close $\hat{b}$ is to b is $$E^2 = \|(b - A\hat{x})\|^2$$

where $\|\cdot\|$ stands for the norm of the error vector. Thus, for each locus, each of the possible genotype matrices is fitted to the given allele peak data vector, b, and the associated residual, $E^2$, is calculated and compared against each other. The genotype pair that gives the smallest fitting error is ranked the highest as the most likely genotype profiles for the two contributors, at this locus, provided the relative allele peak data is consistent with the underlying relative DNA masses in the mixture.

Example 3C

Finding the Most Likely Genotype Combination for Each Locus

If the proportionality between the DNA mass fractions and the associated allele peak areas is preserved, then it is expected that the genotype combination that gives the smallest fitting error residual, if a unique minimum exists, corresponds to the true genotype profiles of the two contributors. Furthermore, by comparing the smallest residual to the next smallest one, one can estimate the confidence with which one can claim the genotype with the smallest fitting residual being the correct one. If the next smallest residual is very much bigger than that of the smallest one, then one can claim with more confidence that the genotype with the smallest residual is the correct genotype combination pattern at that locus.

For a locus with two alleles, there are four possible genotype combinations for the two contributors, as shown in Table 2. The 2-allele case always needs special consideration, because the matrices A of three of the four possible genotype combination cases are full rank. This means that an exact solution exists in solving for x in Ax=b. Therefore, a least-square solution is not involved. Consequently, this also means that the computed mass coefficient vector, x, gives an exact fit to the allele peak area vector and the fitting error is zero. However, this does not necessarily imply that one of these three genotype combination cases is the correct one. It is just that the mathematics involved in solving the problem is such that an exact fit is allowed. Therefore, it is the associated mass ratio that has to be used to determine which genotype combination case is more consistent with the best-fit mass ratios identified from other loci already processed. Two situations exist in the 2-allele case:

If the genotypes of the two individuals are different, as in Cases 1, 2, and 3 shown in Table 2, then the matrix A is full rank, meaning the two columns of A are independent. Therefore, an exact solution x for the equation Ax=b can be obtained from x=A$^+$b; in this case, A$^{-1}$ exists and is equal to A$^+$. As a result, the errors calculated from these three cases are all zero. For this reason, in this case comparing the errors does not help the caseworkers in selecting the best-fit genotype assignment for a two-allele locus. The mass ratio is more indicative of which case is the best-fit case.

If the genotypes for both contributors are the same and each individual is heterozygous at this locus, as in Case 4 shown in Table 2, then regardless of the mixture DNA's mass ratio, the fitted two-allele peak areas at this locus will always be the same. The matrix A that represents this genotype assignment is $$\begin{bmatrix} 1 & 1 \\ 1 & 1 \end{bmatrix}.$$

The two vectors of this matrix are identical, and the rank is 1. Therefore, an exact solution for the equation Ax=b can be found only when the two elements in b vector are also the same, meaning the two allele peak areas are equal to each other. Since there is always uncertainty associated with the allele peak data measurement, they are seldom equal exactly. As a result, no exact solution would be obtained, and the fitting error for this case would always be greater than 0, thus greater than those for the other genotype cases. In addition, the computed fitted mass ratio would always be 1:1, but in most cases, it would be wrong. The real mass ratio can be anything, but cannot be estimated from the least-square fit solution. Therefore, when the peak areas of the two alleles are indeed close, then the possibility exists that Case 4 is the applicable genotype combination case, regardless of the value of the fitting error and its unestimatable mass ratio.

From the above analysis, one can conclude that for loci with only two alleles, comparing the errors associated with each possible genotype combination choice does not help the caseworkers to decide the correct genotypes for the two contributors. The best-fit genotype combination should be the one with a mass ratio consistent with those estimated for other loci with three or four alleles. However, if the ratio of the two allele peak areas is close to 1:1, the genotype combination Case 4 represented by the matrix $$\begin{bmatrix} 1 & 1 \\ 1 & 1 \end{bmatrix}$$

should then be considered possible, even though the error for this case is greater than those for the other cases.

Figure 10:
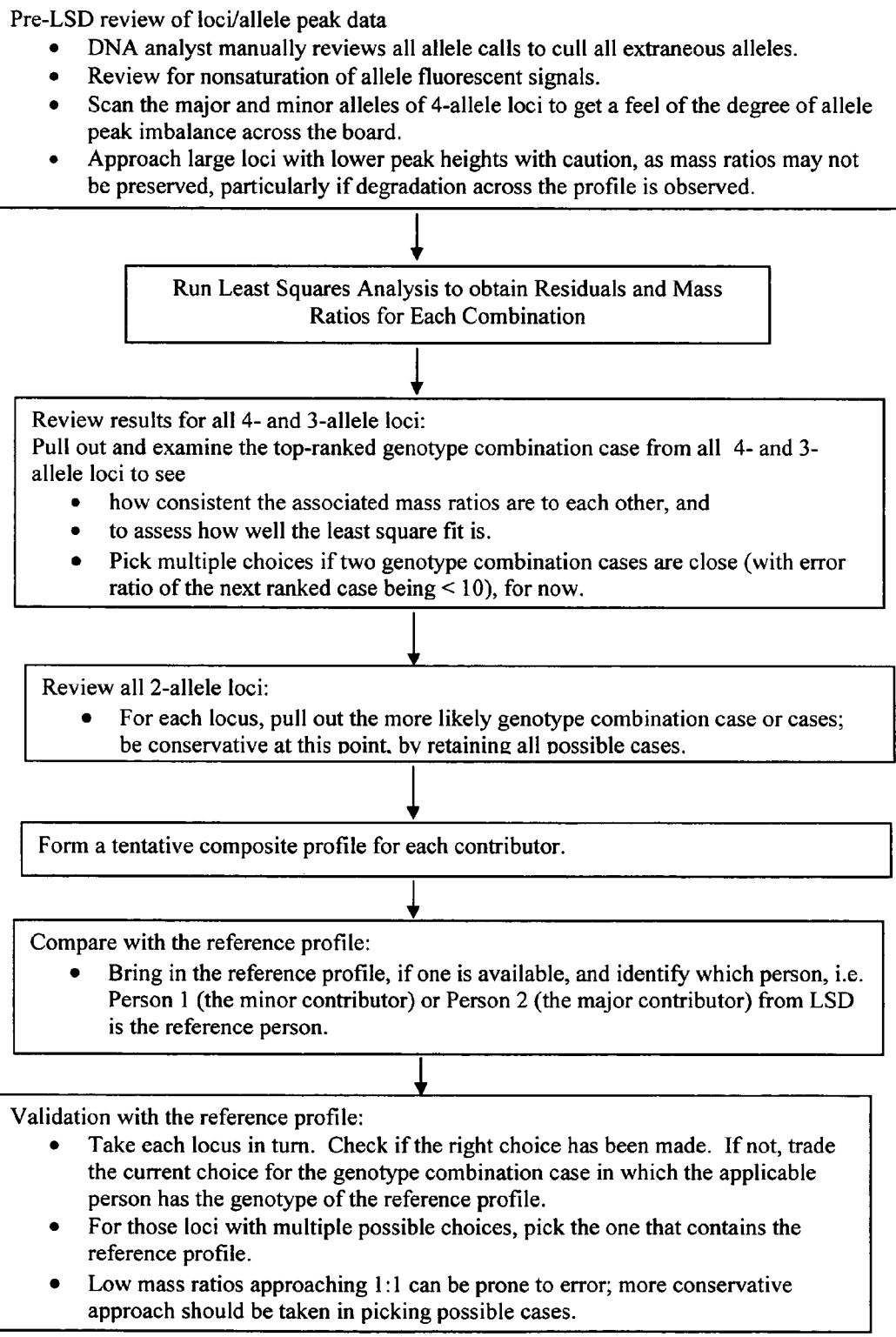
FIG. 10 is a flow diagram with an overview of the major steps in putting together a composite genotype using LSD.

In general, the method to identify the most likely genotype combinations at each locus in LSD, is summarized as follows. FIG. 10 provides a detailed flow diagram of the LSD and identification process. (25) For a locus with three or four alleles, the genotype combination with the smallest fitting residual should first be chosen as the most likely one. The smallest fitting residual may not be chosen if it clusters with the second smallest fitting residual. The smallest fitting residual clusters with the second smallest fitting residual if the smallest and second smallest fitting residuals are much more similar to each other than the second smallest fitting residual is similar to the remaining fitting residuals. The smallest and the second smallest fitting residuals do not cluster if the second smallest fitting residual is less similar to the smallest fitting residual than it is to the remaining fitting residuals, if the second smallest fitting residual is not similar to either the smallest or the remaining fitting residuals, or if the second smallest fitting residual is not much more similar to the smallest fitting residual than the remaining fitting residuals. Examples 4-9 apply the LSD method and thus provide fitting residuals, or fitting errors, for genotype profiles that can be selected for individuals that contribute DNA to a sample. These Examples also discuss the selection of one of these genotype profiles for the individuals, considering the fitting residual or fitting errors of the genotype profiles. Thus these Examples can be used to guide one of skill in the art as to whether a smallest fitting residual clusters with a second smallest fitting residual in determining a genotype profile.

Consistency of mass ratios can also be used in the selection of a genotype profile of a locus if the genotype profile at a second locus has been determined. A consistent mass ratio can refer a mass ratio that is nearly identical for each allele combination selected at each locus in a sample. A consistent mass ratio may also be no more than a 1.2-, 1.5-, 1.8-, 2.0-, 3.0-fold difference between the mass ratios of the genotype profiles of the second locus and the selected locus in the sample.

Figure 11:
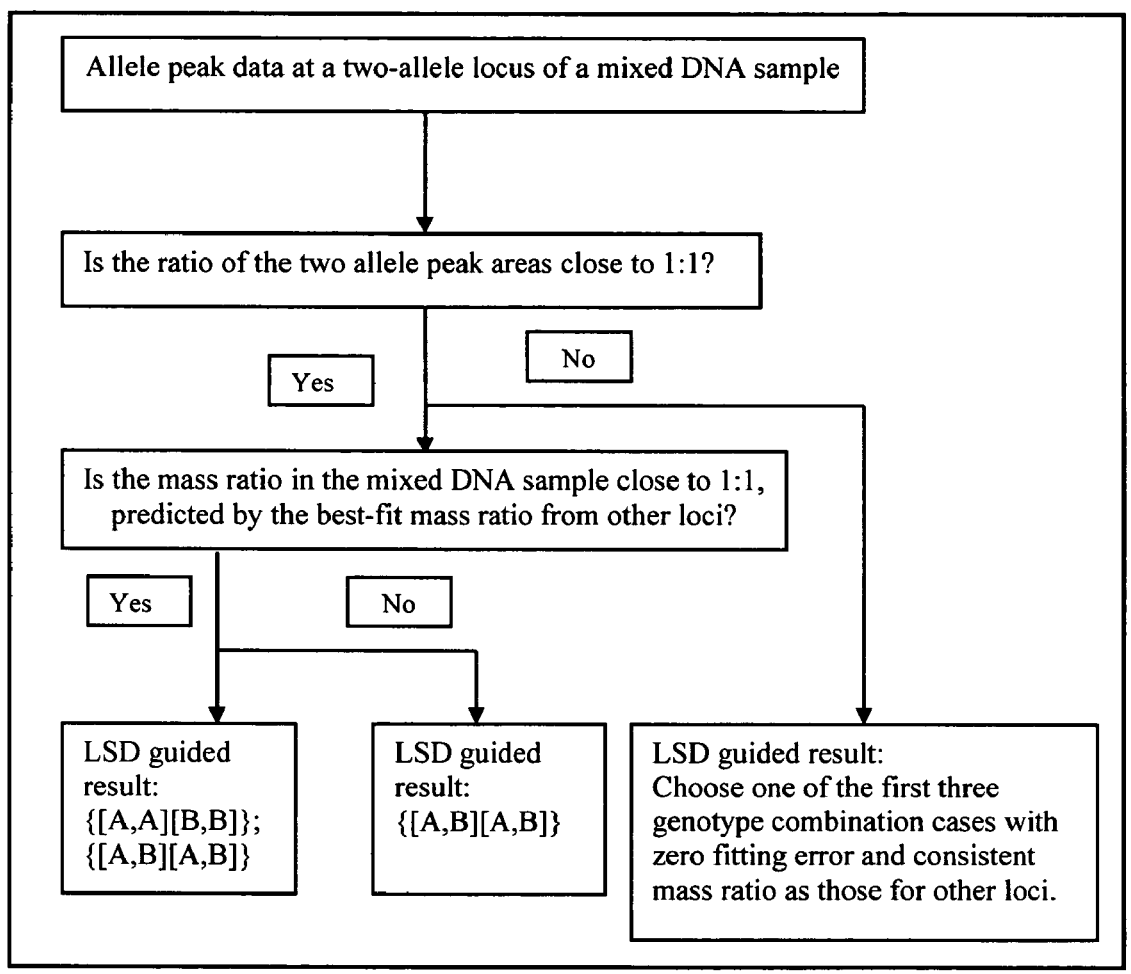
FIG. 11 is a flow sheet of using LSD to resolve mixed DNA at a 2-allele locus.

For a locus with two alleles the flow diagram shown in FIG. 11 may be applied. If the ratio of the two-allele peak areas is not close to 1:1, the genotype combination with the fitted mass ratio consistent with those for other loci should be selected as the most likely one among the first three cases shown in Table 2. If the ratio of the two allele peak areas is close to 1:1 and the approximate mass ratio of the DNA mixture, derived from other loci, is not close to 1:1, the genotype combination in Case 4 shown in Table 2 {[A, B][A, B]} should then be considered as the only possibility, even though the error for this case is greater than those for the other cases. If the ratio of the two allele peak areas is close to 1:1 and the approximate mass ratio of the DNA mixture is also close to 1:1, then there are two possible genotype combinations {[A, A][B, B]} and {[A, B][A, B]}, both of which can fit equally well to the measured allele peak areas.

Example 3D

Reviewing the Ranking Result and Forming the Composite Profiles

From pooling together the most likely genotype combinations at all loci, the best-fit genotype profiles can be established for the two source contributors. Since the best-fit mass ratio varies somewhat from locus to locus, an approximate mass ratio of the DNA mixture sample can be obtained by averaging across the individual mass ratios from each locus.

It is also possible to consider a range of mass ratios for a majority of the three or four allele loci as a cluster of mass ratios.

It is also possible to compare the genotype profiles selected with a reference profile to validate the genotype profile choices made, and to further resolve ambiguities may exist when more than one combination at a locus has not been ruled out.

Example 4

Figure 12:
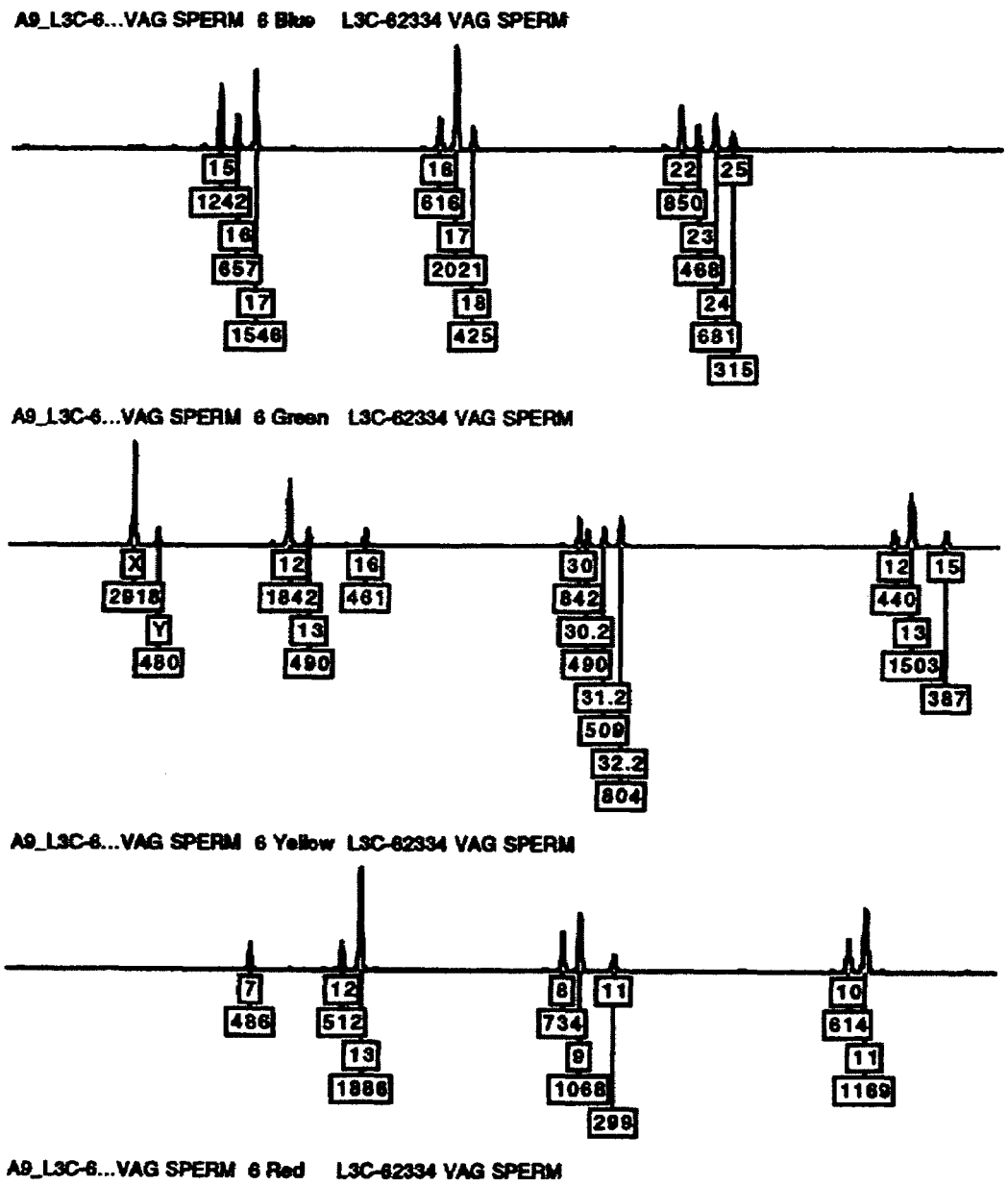
FIG. 12 shows the allele peaks at twelve loci of Texas DNA mixture data number 1; both the allele name and the corresponding peak areas are indicated.
Figure 13A:
FIGS. 13A, B, and C show the output of web-LSD for Texas DNA mixture data number 1. All possible genotype combinations are ranked at each locus according to the magnitudes of the fitting errors.

Application of Least Square Approach (LSD) Principles Resolves a Mixed Forensic DNA Sample into Each Contributor's Genotype LSD was used to successfully resolve a DNA mixture obtained from a rape case into the genotype profile of the victim and the suspect. Examples 4A, B, and C illustrate the application of the LSD approach to resolve the DNA sample into each contributor' genotype profile at each of a three-allele (VWA), four-allele (D21S11), and two-allele locus (D7S820). FIG. 12 shows the output of a Genescan software program used to detect the alleles of the victim and suspect at nine loci (19). The alleles and allele peaks are seen on the data output. The peak areas obtained from the Genescan output and the known genotypes of the victim and the suspect are listed in Table 4. The output of the web-LSD analysis of the allele peak areas is shown in FIG. 13A-C. The web-LSD was based on previous Visual Basic and Matlab implementations of the software to support LSD (20).

TABLE 4

| Locus | Alleles in the Mixture | Peak Areas | Genotypes Victim | Suspect |
|---|---|---|---|---|
| D3S1358 | 15 | 1242 | 15, 17 | 16, 17 |
|  | 16 | 657 |  |  |
|  | 17 | 1546 |  |  |
| VWA | 16 | 616 | 17, 17 | 16, 18 |
|  | 17 | 2021 |  |  |
|  | 18 | 425 |  |  |
| FGA | 22 | 850 | 22, 24 | 23, 25 |
|  | 23 | 468 |  |  |
|  | 24 | 681 |  |  |
|  | 25 | 315 |  |  |
| D8S1179 | 12 | 1842 | 12, 12 | 13, 16 |
|  | 13 | 490 |  |  |
|  | 16 | 461 |  |  |
| D21S11 | 30 | 842 | 30, 32.2 | 30.2, 31.2 |
|  | 30.2 | 490 |  |  |
|  | 31.2 | 509 |  |  |
|  | 32.2 | 804 |  |  |
| D18S51 | 12 | 440 | 13, 13 | 12, 15 |
|  | 13 | 1503 |  |  |
|  | 15 | 387 |  |  |
| D5S818 | 7 | 486 | 13, 13 | 7, 12 |
|  | 12 | 512 |  |  |
|  | 13 | 1886 |  |  |
| D13S317 | 8 | 734 | 8, 9 | 9, 11 |
|  | 9 | 1068 |  |  |
|  | 11 | 299 |  |  |
| D7S820 | 10 | 614 | 11, 11 | 10, 10 |
|  | 11 | 1169 |  |  |

Example 4A

Application of LSD Analysis at a Three-Allele Locus to Predict the Profile of the Two Contributors As shown in Table 4, locus VWA has three alleles. The allele peak data at this locus are first normalized and represented with a vector 'b':

$$b = \begin{bmatrix} 616/425 \\ 2021/425 \\ 425/425 \end{bmatrix} = \begin{bmatrix} 1.45 \\ 4.76 \\ 1 \end{bmatrix}.$$

All six possible genotype combinations for this 3-allele locus and their corresponding matrix 'A' at this locus are listed in Table 5.

TABLE 5

| | Combination Genotype | | | Pseudoinverse of the |
|---|---|---|---|---|
| Case | Person 1 | Person 2 | Matrix (A) | Matrix ($A^+$) |
| 1 | 16, 16 | 17, 18 | $\begin{bmatrix} 2 & 0 \\ 0 & 1 \\ 0 & 1 \end{bmatrix}$ | $\frac{1}{2}\begin{bmatrix} 1 & 0 & 0 \\ 0 & 1 & 1 \end{bmatrix}$ |
| 2 | 17, 17 | 16, 18 | $\begin{bmatrix} 0 & 1 \\ 2 & 0 \\ 0 & 1 \end{bmatrix}$ | $\frac{1}{2}\begin{bmatrix} 0 & 1 & 0 \\ 1 & 0 & 1 \end{bmatrix}$ |
| 3 | 18, 18 | 16, 17 | $\begin{bmatrix} 0 & 1 \\ 0 & 0 \\ 2 & 1 \end{bmatrix}$ | $\frac{1}{2}\begin{bmatrix} 0 & 0 & 1 \\ 1 & 1 & 0 \end{bmatrix}$ |
| 4 | 16, 17 | 17, 18 | $\begin{bmatrix} 1 & 0 \\ 1 & 1 \\ 0 & 1 \end{bmatrix}$ | $\frac{1}{3}\begin{bmatrix} 2 & 1 & -1 \\ -1 & 1 & 2 \end{bmatrix}$ |
| 5 | 16, 17 | 16, 18 | $\begin{bmatrix} 1 & 1 \\ 1 & 0 \\ 0 & 1 \end{bmatrix}$ | $\frac{1}{3}\begin{bmatrix} 1 & 2 & -1 \\ 1 & -1 & 2 \end{bmatrix}$ |
| 6 | 16, 18 | 17, 18 | $\begin{bmatrix} 1 & 0 \\ 0 & 1 \\ 1 & 1 \end{bmatrix}$ | $\frac{1}{3}\begin{bmatrix} 2 & -1 & 1 \\ -1 & 2 & 1 \end{bmatrix}$ |

For each possible genotype combination, the least-square solution $\hat{x}$ for the equation Ax=b is solved by multiplying the corresponding pseudoinverse of A, (i.e. $A^+$) to the vector 'b'. The error residual was calculated. Case 1 is used as an example to show how the residual error is calculated. For Case 1, the corresponding A matrix is:

$$\begin{bmatrix} 2 & 0 \\ 0 & 1 \\ 0 & 1 \end{bmatrix}.$$

The linear equation for this case is:

$$Ax = b \Rightarrow \begin{bmatrix} 2 & 0 \\ 0 & 1 \\ 0 & 1 \end{bmatrix} x = \begin{bmatrix} 1.45 \\ 4.76 \\ 1 \end{bmatrix},$$

and the least-square solution $\hat{x}$ is decided as follows:

$$\hat{x} = A^+ b = \frac{1}{2}\begin{bmatrix} 1 & 0 & 0 \\ 0 & 1 & 1 \end{bmatrix} \cdot \begin{bmatrix} 1.45 \\ 4.76 \\ 1 \end{bmatrix} = \begin{bmatrix} 0.73 \\ 2.88 \end{bmatrix},$$

where $A^+$ is obtained from Table 2. The residual for the fit is calculated as:

$$E^2 = \|(b - A\hat{x})\|^2 = \left\| \begin{bmatrix} 1.45 \\ 4.76 \\ 1 \end{bmatrix} - \begin{bmatrix} 2 & 0 \\ 0 & 1 \\ 0 & 1 \end{bmatrix} \cdot \begin{bmatrix} 0.73 \\ 2.88 \end{bmatrix} \right\|^2 = \left\| \begin{bmatrix} -0.01 \\ 1.88 \\ -1.88 \end{bmatrix} \right\|^2$$

$$= (-0.01)^2 + 1.88^2 + (-1.88)^2 = 7.0689$$

The normalized mass ratio vector is:

$$\begin{bmatrix} 0.73/0.73 \\ 2.88/0.73 \end{bmatrix} = \begin{bmatrix} 1 \\ 3.95 \end{bmatrix},$$

which is the normalized least-square solution $\hat{x}$ reflecting the approximate mass ratio in the mixture sample for that locus. The least-square solution $\hat{x}$ and the associated error residual for other cases were also calculated in the same manner as that for Case 1, and results are shown in Table 6.

TABLE 6

| | Genotype Combinations | | | Ratio of | Mass Ratio |
|---|---|---|---|---|---|
| Cases | Person 1 | Person 2 | Matrix A | Errors | Calculated |
| 1 | 16, 16 | 17, 18 | $\begin{bmatrix} 2 & 0 \\ 0 & 1 \\ 0 & 1 \end{bmatrix}$ | 69.82 | 1:3.95 |
| 2 | 16, 18 | 17, 17 | $\begin{bmatrix} 0 & 1 \\ 2 & 0 \\ 0 & 1 \end{bmatrix}$ | 1 | 1:1.94 |
| 3 | 18, 18 | 16, 17 | $\begin{bmatrix} 0 & 1 \\ 0 & 0 \\ 2 & 1 \end{bmatrix}$ | 54.11 | 1:6.20 |
| 4 | 17, 18 | 16, 17 | $\begin{bmatrix} 1 & 0 \\ 1 & 1 \\ 0 & 1 \end{bmatrix}$ | 17.55 | 1:1.25 |
| 5 | 16, 18 | 16, 17 | $\begin{bmatrix} 1 & 1 \\ 1 & 0 \\ 0 & 1 \end{bmatrix}$ | 61.20 | 1:−7.63 |

TABLE 6-continued

| | Genotype Combinations | | | Ratio of | Mass Ratio |
|---|---|---|---|---|---|
| Cases | Person 1 | Person 2 | Matrix A | Errors | Calculated |
| 6 | 16, 18 | 17, 18 | $\begin{bmatrix} 1 & 0 \\ 0 & 1 \\ 1 & 1 \end{bmatrix}$ | 89.42 | 1:−10.58 |

The first column of the table is the case number for each genotype combination; all possible genotype combination cases are listed in the second and third columns; the fourth column of the table is the corresponding genotype matrix; the fifth column is the ratio of the calculated errors, with the smallest error normalized to one; the normalized mass ratios calculated from the fitted $\hat{x}$ are listed in the sixth column.

Figure 14:
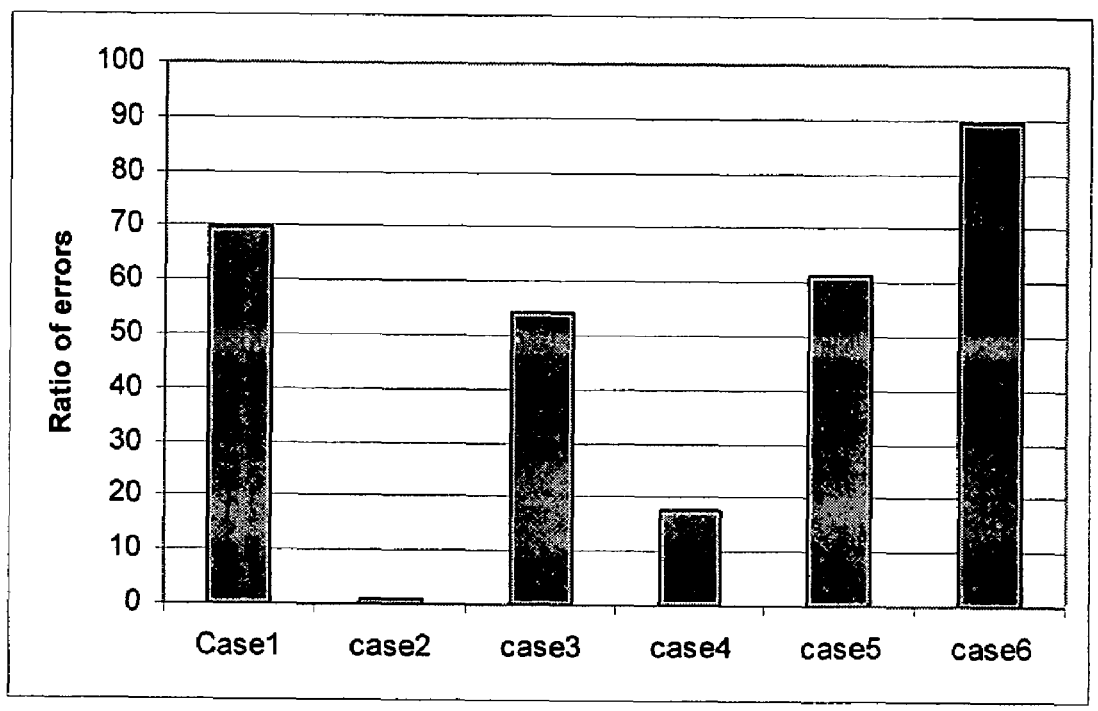
FIG. 14 shows the normalized fitting residuals of all possible genotype combinations at the locus VWA in the DNA mixture data.

FIG. 14 shows the error residual for each of the possible genotype combination cases. Therefore, all the genotype combinations for locus VWA can be ranked according to the magnitudes of the corresponding residual errors. Case 2 clearly has the smallest fitting error. The next smallest error, that of Case 4, has an error 17 times as large as that for Case 2, indicating genotype combination of Case 2 is clearly the best-fit one if the relative allele peak area proportion is credible. Table 7 is the ranking result for locus VWA with three alleles.

TABLE 7

| | Genotype Combinations | | | Ratio of | Mass Ratio |
|---|---|---|---|---|---|
| Rank | Person 1 | Person 2 | Matrix A | Errors | Calculated |
| 1 | 16, 18 | 17, 17 | $\begin{bmatrix} 0 & 1 \\ 2 & 0 \\ 0 & 1 \end{bmatrix}$ | 1 | 1:1.94 |
| 2 | 17, 18 | 16, 17 | $\begin{bmatrix} 1 & 0 \\ 1 & 1 \\ 0 & 1 \end{bmatrix}$ | 17.55 | 1:1.25 |
| 3 | 18, 18 | 16, 17 | $\begin{bmatrix} 0 & 1 \\ 0 & 0 \\ 2 & 1 \end{bmatrix}$ | 54.11 | 1:6.20 |
| 4 | 16, 18 | 16, 17 | $\begin{bmatrix} 1 & 1 \\ 1 & 0 \\ 0 & 1 \end{bmatrix}$ | 61.20 | 1:−7.63 |
| 5 | 16, 16 | 17, 18 | $\begin{bmatrix} 2 & 0 \\ 0 & 1 \\ 0 & 1 \end{bmatrix}$ | 69.82 | 1:3.95 |
| 6 | 16, 18 | 17, 18 | $\begin{bmatrix} 1 & 0 \\ 0 & 1 \\ 1 & 1 \end{bmatrix}$ | 89.42 | 1:−10.58 |

From the ranking result, one can see that the fitting error of the first ranked genotype combination is clearly much smaller than the next smallest one; therefore, the genotype combination of {[16, 18], [17, 17]} is identified as the best-fit for this locus, and the mix is at the approximate mass ratio of 1:1.94. The genotype combination with a negative number in the calculated mass coefficients can be excluded at once because the mass coefficients must be positive.

Example 4B

Application of LSD Analysis at a Four-Allele Locus to Predict the Profile of the Two Contributors The allele peak data at locus D21S11 shown in Table 4 is used to illustrate how a 4-allele pattern at a locus is resolved into its most likely components using LSD. First, all possible genotype assignments for this locus are listed in Table 8.

TABLE 8

| | Genotype Combination | | | |
|---|---|---|---|---|
| Case | Person 1 | Person 2 | Matrix (A) | Pseudoinverse of the Matrix ($A^+$) |
| 1 | 30, 30.2 | 31.2, 32.2 | $\begin{bmatrix} 1 & 0 \\ 1 & 0 \\ 0 & 1 \\ 0 & 1 \end{bmatrix}$ | $\frac{1}{2}\begin{bmatrix} 1 & 1 & 0 & 0 \\ 0 & 0 & 1 & 1 \end{bmatrix}$ |
| 2 | 30, 31.2 | 30.2, 32.2 | $\begin{bmatrix} 1 & 0 \\ 0 & 1 \\ 1 & 0 \\ 0 & 1 \end{bmatrix}$ | $\frac{1}{2}\begin{bmatrix} 1 & 0 & 1 & 0 \\ 0 & 1 & 0 & 1 \end{bmatrix}$ |
| 3 | 30, 32.2 | 30.2, 31.2 | $\begin{bmatrix} 1 & 0 \\ 0 & 1 \\ 0 & 1 \\ 1 & 0 \end{bmatrix}$ | $\frac{1}{2}\begin{bmatrix} 1 & 0 & 0 & 1 \\ 0 & 1 & 1 & 0 \end{bmatrix}$ |

Figure 15:
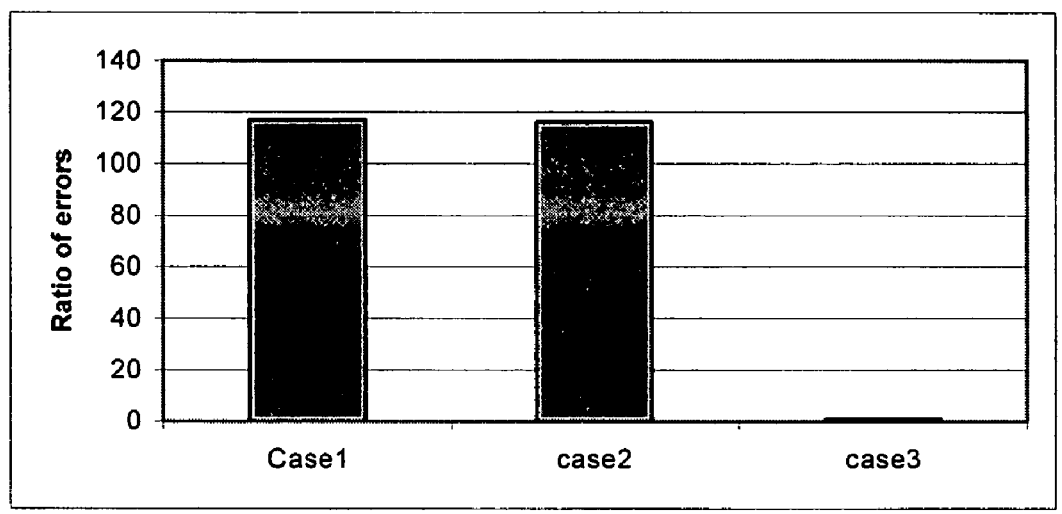
FIG. 15 shows the normalized fitting residuals of all possible genotype combinations at the locus D21S11 in the DNA mixture data.

For each possible genotype combination, the fitting error and the best-fit mass coefficients are calculated. FIG. 15 shows the relative error of each possible genotype combination when normalized to the smallest error (Case 3). The LSD ranking result for this locus is shown in Table 9.

TABLE 9

| | Genotype Combinations | | | Ratio of | Mass Ratio |
|---|---|---|---|---|---|
| Rank | Person 1 | Person 2 | Matrix A | Errors | Calculated |
| 1 | 30.2, 31.2 | 30, 32.2 | $\begin{bmatrix} 1 & 0 \\ 0 & 1 \\ 0 & 1 \\ 1 & 0 \end{bmatrix}$ | 1 | 1:1.65 |
| 2 | 30.2, 32.2 | 30, 31.2 | $\begin{bmatrix} 1 & 0 \\ 0 & 1 \\ 1 & 0 \\ 0 & 1 \end{bmatrix}$ | 116.06 | 1:1.04 |
| 3 | 31.2, 32.2 | 30, 30.2 | $\begin{bmatrix} 1 & 0 \\ 1 & 0 \\ 0 & 1 \\ 0 & 1 \end{bmatrix}$ | 116.86 | 1:1.01 |

The top ranked genotype combination of {[30.2, 31.2][30, 32.2]} is considered to be the most likely one with the approximate mass ratio of 1:1.65. Note that the best-fit mass ratio of 1:1.65 for this locus is consistent with the best-fit mass ratio of 1:1.94 for the 3-allele locus VWA, derived in the previous section.

Example 4C

Application of LSD Analysis at a Two-Allele Locus to Predict the Profile of the Two Contributors If only two alleles are present at a locus, then there are four possible genotype combinations for the two contributors, as shown in Table 10.

TABLE 10

| | Genotype Combination | | | |
|---|---|---|---|---|
| Case | Person 1 | Person 2 | Matrix (A) | Pseudoinverse of the Matrix ($A^+$) |
| 1 | A, A | B, B | $\begin{bmatrix} 2 & 0 \\ 0 & 2 \end{bmatrix}$ | $\frac{1}{2}\begin{bmatrix} 1 & 0 \\ 0 & 1 \end{bmatrix}$ |
| 2 | A, B | A, A | $\begin{bmatrix} 1 & 2 \\ 1 & 0 \end{bmatrix}$ | $\frac{1}{2}\begin{bmatrix} 0 & 2 \\ 1 & -1 \end{bmatrix}$ |
| 3 | A, B | B, B | $\begin{bmatrix} 1 & 0 \\ 1 & 2 \end{bmatrix}$ | $\frac{1}{2}\begin{bmatrix} 2 & 0 \\ -1 & 1 \end{bmatrix}$ |
| 4 | A, B | A, B | $\begin{bmatrix} 1 & 1 \\ 1 & 1 \end{bmatrix}$ | $\frac{1}{4}\begin{bmatrix} 1 & 1 \\ 1 & 1 \end{bmatrix}$ |

All possible genotype assignments for this locus are listed in Table 4.11 based on the allele contributions of the individuals at locus D7S820 using the data shown in Table 4.

TABLE 11

| | Genotype Combination | | | |
|---|---|---|---|---|
| Case | Person 1 | Person 2 | Matrix (A) | Pseudoinverse of the Matrix ($A^+$) |
| 1 | 10, 10 | 11, 11 | $\begin{bmatrix} 2 & 0 \\ 0 & 2 \end{bmatrix}$ | $\frac{1}{2}\begin{bmatrix} 1 & 0 \\ 0 & 1 \end{bmatrix}$ |
| 2 | 10, 11 | 10, 10 | $\begin{bmatrix} 1 & 2 \\ 1 & 0 \end{bmatrix}$ | $\frac{1}{2}\begin{bmatrix} 0 & 2 \\ 1 & -1 \end{bmatrix}$ |
| 3 | 10, 11 | 11, 11 | $\begin{bmatrix} 1 & 0 \\ 1 & 2 \end{bmatrix}$ | $\frac{1}{2}\begin{bmatrix} 2 & 0 \\ -1 & 1 \end{bmatrix}$ |
| 4 | 10, 11 | 10, 11 | $\begin{bmatrix} 1 & 1 \\ 1 & 1 \end{bmatrix}$ | $\frac{1}{4}\begin{bmatrix} 1 & 1 \\ 1 & 1 \end{bmatrix}$ |

At this locus, the errors of all possible genotype combinations are calculated. The calculated errors and the ranking result for this locus are shown in Table 12.

TABLE 12

| Cases | Rank | Genotype Combinations Person 1 | Person 2 | Matrix A | Errors | Mass Ratio Calculated |
|---|---|---|---|---|---|---|
| 1 | 1 | 10, 10 | 11, 11 | $\begin{bmatrix} 2 & 0 \\ 0 & 2 \end{bmatrix}$ | 0 | 1:1.90 |
| 2 | 1 | 10, 10 | 10, 11 | $\begin{bmatrix} 1 & 2 \\ 1 & 0 \end{bmatrix}$ | 0 | 1:-4.21 |
| 3 | 1 | 11, 11 | 10, 11 | $\begin{bmatrix} 1 & 0 \\ 1 & 2 \end{bmatrix}$ | 0 | 1:2.21 |
| 4 | 2 | 10, 11 | 10, 11 | $\begin{bmatrix} 1 & 1 \\ 1 & 1 \end{bmatrix}$ | 0.41 | Indeterminate |

Since the peak area ratio of the two alleles (614:1169) at locus D7S820 is not close to 1:1, one does not need to consider Case 4 with the genotype combination of {[10, 11][10, 11]} as a possibility. Recall the best-fit mass ratios from loci VWA and D21S11 are 1:1.94 and 1:1.65, respectively. Therefore, either Case 1 or Case 3 is a possibility with the fitted mass ratio of 1:1.9 and 1:2.21, respectively. These two genotype combinations are {[10, 10][11, 11]} and {[11, 11][10, 11]}. The genotype of the victim, if available, can definitely help the caseworkers to select the more appropriate genotype combination case from the two alternative choices. If more than one case yields a mass ratio consistent with those from other loci, then. DNA for this locus cannot be resolved unambiguously, which means LSD suggests more than one genotype combination, both of which are equally likely to be the true case. The only way to ascertain the choice is to pick out the genotype combination case, in which the known victim's genotype or the reference genotype is one of the genotype profiles in the combination. It turns out the combination of {[10, 10] [11, 11]} is the pick of the choice because the victim's (person 2) profile at this locus is [11, 11].

The other six loci of Table 4 were analyzed with the same LSD interpretation approach. Compared with the true genotypes of the two contributors, LSD give the correct genotype profiles at all 3-allele and 4-allele loci, for this example. For those 2-allele loci, LSD yielded two possible choices for each locus. When the genotype of the victim at this locus was brought in, the better choice was identified. Therefore, in this case, LSD results at all nine loci are consistent with the genotypes of the victim and the suspect.

Example 5

The LSD Approach Correctly Predicts the Genotype Profile of Two Contributors in a Simulated DNA Sample with Two Contributors Allele peak data of DNA mixture samples were simulated at six loci. The loci contained two, three, or four alleles and mass ratios of 1:1, 1:2, and 1:5. The sets of simulated data are shown in Table 13.

TABLE 13

| Locus | Alleles in the Mixture | Genotype Combination Person 1 | Person 2 | Simulated Allele Peak Data 1:5 | 1:2 | 1:1 |
|---|---|---|---|---|---|---|
| VWA | 15 | 15, 15 | 16, 19 | 1302 | 1506 | 1472 |
|  | 16 |  |  | 3369 | 1369 | 730 |
|  | 19 |  |  | 3446 | 1348 | 769 |
| TH01 | 6 | 6, 7 | 6, 9.3 | 5620 | 5008 | 5979 |
|  | 7 |  |  | 807 | 1875 | 3057 |
|  | 9.3 |  |  | 5095 | 3155 | 3122 |
| D8S1179 | 11 | 11, 13 | 11, 13 | 5519 | 5284 | 4339 |
|  | 13 |  |  | 4913 | 5733 | 4922 |
| FGA | 22 | 22, 22 | 22, 25 | 9019 | 4675 | 8596 |
|  | 25 |  |  | 6240 | 2232 | 2444 |
| D21S11 | 28 | 28, 28 | 30.2, 30.2 | 958 | 1098 | 1001 |
|  | 30.2 |  |  | 5234 | 1941 | 873 |
| D18S51 | 16 | 16, 20 | 17, 18 | 804 | 731 | 975 |
|  | 17 |  |  | 5202 | 1806 | 882 |
|  | 18 |  |  | 4212 | 1640 | 899 |
|  | 20 |  |  | 864 | 913 | 873 |

First, at each locus, the genotype combination of the two contributors is coded into a matrix 'A.' In accordance to the mass ratio assumed for each set of data, the corresponding theoretical allele peak data vector 'b' at this locus was then calculated from the equation $Ax=b$, where the 'x' vector contains the mass ratio coefficients for the two contributors. In real cases, some noise or peak area imbalances are always associated with the measurements of allele peak areas. Therefore, in the simulated data, a 10% Gaussian noise (random Gaussian noise with mean 0 and standard deviation of 10% of the nominal peak area) is added to the theoretical allele peak values.

Example 5A

A Simulated DNA Mixture with a Mass Ratio of 1:5

The simulated DNA mixture shown in Table 13 for the mass ratio of 1:5 was analyzed by the LSD method. FIGS. 16A and 16B show the detailed web-LSD output for this set of data. Table 14 is the LSD suggested genotype resolution result of analyzing the simulated data for a mass ratio of 5:1.

TABLE 14

| Locus | Alleles in the Mixture | Peak Area Ratio Measured | LSD Suggested Genotype Resolution Result Person 1 | Person 2 | Mass Ratio Calculated | Remarks |
|---|---|---|---|---|---|---|
| VWA | 15, 16, 19 | 1:2.59:2.65 | 15, 15 | 16, 19 | 1:5.23 | Correct |
| TH01 | 6, 7, 9.3 | 6.96:1:6.31 | 6, 7 | 6, 9.3 | 1:7.01 | Correct |

TABLE 14-continued

| Locus | Alleles in the Mixture | Peak Area Ratio Measured | LSD Suggested Genotype Resolution Result | | | |
|---|---|---|---|---|---|---|
| | | | Person 1 | Person 2 | Mass Ratio Calculated | Remarks |
| D8S1179 | 11, 13 | 1.12:1 | 11, 13 | 11, 13 | Indeterminate | See Table 15 for details |
| FGA | 22, 25 | 1.45:1 | 22, 22 | 22, 25 | 1:4.49 | Correct |
| D21S11 | 28, 30.2 | 1:5.46 | 28, 28 | 30.2, 30.2 | 1:5.46 | Correct |
| D18S51 | 16, 17, 18, 20 | 1:6.47:5.24:1.07 | 16, 20 | 17, 18 | 1:5.64 | Correct |

Note:
'correct' in the table means the top-ranked genotype combination selected by LSD corresponds to the true genotype profiles of the two contributors.

For loci VWA, TH01, FGA, D21S11, and D18S51, the top-ranked genotype combinations suggested by LSD correspond to the correct genotype profiles of the two contributors. At these five loci, the fitted mass ratios are reviewed to be more or less consistent with each other ranging from 1:4.49 to 1:7.01. The average of the five mass ratios is 1:5.57, which is close to the true mass ratio of 1:5 in this simulated DNA mixture sample.

The remaining locus of D8S1179 has only 2 alleles, and LSD suggested results for a 2-allele locus always needs special review and interpretation. The ranking result for all possible genotype combinations for this locus is presented in Table 15.

TABLE 15

| Case | Rank | Genotype Combinations | | Matrix A | Errors | Mass Ratio Calculated |
|---|---|---|---|---|---|---|
| | | Person 1 | Person 2 | | | |
| 1 | 1 | 13, 13 | 11, 11 | $\begin{bmatrix} 2 & 0 \\ 0 & 2 \end{bmatrix}$ | 0 | 1:1.12 |
| 2 | 1 | 13, 13 | 11, 13 | $\begin{bmatrix} 1 & 0 \\ 1 & 2 \end{bmatrix}$ | 0 | 1:−18.21 |
| 3 | 1 | 11, 11 | 11, 13 | $\begin{bmatrix} 1 & 2 \\ 1 & 0 \end{bmatrix}$ | 0 | 1:16.21 |
| 4 | 2 | 11, 13 | 11, 13 | $\begin{bmatrix} 1 & 1 \\ 1 & 1 \end{bmatrix}$ | 0.0076 | 1:1 |

Three genotype combinations all fit the given allele peak data exactly with zero errors. However, their corresponding best-fit mass ratios are 1:1, 1:−18.2, and 1:16.2; all are inconsistent with those for other loci. For the genotype combination of {[11, 13] [11, 13]}, if it were true, then regardless of the mass ratio in the DNA mixture, the ratio of the allele peak data would always be close to 1:1, and it is (1.12:1). As a result, the true mass ratio would be unknown at this locus. The best-fit mass ratio in this case, given by LSD usually is not the correct one, due to the 'A' matrix for this case being underdetermined (meaning not all rows or columns of 'A' are independent), and mathematically an infinite set of solutions exist and LSD would give the one with the smallest length, the normalized result would always be 1:1. Therefore, for the case of 2-allele loci, when the other three genotype combinations all give a best-fit mass ratio that is inconsistent with those for other loci, the fourth case is the preferred choice, especially when the ratio of the two allele peaks is close to 1:1. As a result, we choose this genotype combination to be the most likely one. It turns out that it is the correct one.

Example 5B

A Simulated DNA Mixture with a Ratio of 1:2

Table 13, above, also contains the data for the simulated DNA mixture with a mass ratio of 1:2. This data was also input into the LSD method for analysis. FIGS. 17A and B show the detailed web-LSD output for this data set. Table 16 is the resulting LSD suggested genotype resolution obtained for this simulated data set.

TABLE 16

| Locus | Alleles in the Mixture | Peak Area Ratio Measured | LSD suggested Genotype Resolution Result | | | |
|---|---|---|---|---|---|---|
| | | | Person 1 | Person 2 | Mass Ratio Calculated | Remarks |
| VWA | 15, 16, 19 | 1.12:1.02:1 | 15, 15 | 16, 19 | 1:1.80 | Correct |
| TH01 | 6, 7, 9.3 | 2.67:1:1.68 | 6, 7 | 6, 9.3 | 1:1.69 | Correct |
| D8S1179 | 11, 13 | 1:1.09 | 11, 13 | 11, 13 | Indeterminate | Correct |
| FGA | 22, 25 | 2.09:1 | 25, 25 | 22, 22 | 1:2.10 | With equal confidence |
| D21S11 | 28, 30.2 | 1:1.77 | 22, 22 | 22, 25 | 1:1.83 | With equal confidence |
| | | | 28, 28 | 30.2, 30.2 | 1:1.77 | With equal confidence |
| | | | 30.2, 30.2 | 28, 30.2 | 1:2.61 | With equal confidence |
| D18S51 | 16, 17, 18, 20 | 1:2.47:2.24:1.25 | 16, 20 | 17, 18 | 1:2.10 | Correct |

LSD guided genotype combination pair at each locus of VWA, TH01, and D18S51 can be picked out by first ranking the least-square fitting residuals for all genotype combinations and then selecting the top-ranked one with the smallest fitting errors.

At the two-allele locus D8S1179, the genotype combination of {[11, 13] [11, 13]} is selected as the most fitting one, because the ratio of the two allele peak areas is close to 1:1 (1:1.09) and the other patterns' fitted mass ratios are not consistent with those for other loci.

For locus FGA, the ranking result for all possible genotype combinations is presented in Table 17. For a 2-allele locus, when the mass ratio of the DNA is close to 1:2, and the ratio of the two allele peak areas is also close to 2:1 (or 1:2), two genotype combinations of {[B, B] [A, A]} and {[A, A] [A, B]} will both generate two allele peaks with the ratio of the peak A to peak B area being close to 2:1. Therefore, LSD guided results generate two best-fit genotype combinations for each of the two loci. This is a limitation of LSD imposed by the underlying mathematics. In this case, one can make the decision as to which one is the best choice, after the genotype of the victim is brought in for reference. The analysis for locus D21S11 is similar. In Table 16, the true genotypes of the two contributors are indicated as shaded cells.

TABLE 17

| Case | Rank | Genotype Combinations Person 1 | Person 2 | Matrix A | Errors | Mass Ratio Calculated |
|---|---|---|---|---|---|---|
| 1 | 1 | 25, 25 | 22, 22 | $\begin{bmatrix} 2 & 0 \\ 0 & 2 \end{bmatrix}$ | 0 | 1:2.1 |
| 2 | 1 | 22, 22 | 22, 25 | $\begin{bmatrix} 1 & 0 \\ 1 & 2 \end{bmatrix}$ | 0 | 1:1.8 |
| 3 | 1 | 25, 25 | 22, 25 | $\begin{bmatrix} 1 & 2 \\ 1 & 0 \end{bmatrix}$ | 0 | 1:-3.8 |
| 4 | 2 | 22, 25 | 22, 25 | $\begin{bmatrix} 1 & 1 \\ 1 & 1 \end{bmatrix}$ | 0.60 | 1:1 |

Example 5C

A Simulated DNA Mixture with a Ratio of 1:1

Table 13, above, also contains the data for the simulated DNA mixture with a mass ratio of 1:1. This data was input into the LSD method for analysis. FIGS. 18A and B show the detailed web-LSD output for this data set. Table 18 shows the suggested genotype resolution using the output results of the LSD method.

TABLE 18

| Locus | Alleles in the Mixture | Peak Area Ratio Measured | LSD suggested Genotype Resolution Result | | | |
|---|---|---|---|---|---|---|
| | | | Person 1 | Person 2 | Mass Ratio Calculated | Remarks |
| VWA | 15, 16, 19 | 2.02:1:1.05 | 15, 16 | 15, 19 | 1:1.05 | With equal confidence |
| | | | 15, 19 | 15, 16 | 1.05:1 | With equal confidence |
| | | | 15, 15 | 16, 19 | 1:1.02 | With equal confidence |
| | | | 16, 19 | 15, 15 | 1.02:1 | With equal confidence |
| TH01 | 6, 7, 9.3 | 1.96:1:1.02 | 6, 6 | 7, 9.3 | 1:1.03 | With equal confidence |
| | | | 7, 9.3 | 6, 6 | 1.03:1 | With equal confidence |
| | | | 6, 7 | 6, 9.3 | 1:1.02 | With equal confidence |
| | | | 6, 9.3 | 6, 7 | 1.02:1 | With equal confidence |
| D8S1179 | 11, 13 | 1:1.13 | 11, 11 | 13, 13 | 1:1.13 | With equal confidence |
| | | | 13, 13 | 11, 11 | 1.13:1 | With equal confidence |
| | | | 11, 13 | 11, 13 | Indeterminate | With equal confidence |
| FGA | 22, 25 | 3.52:1 | 22, 25 | 22, 22 | 1:1.26 | With equal confidence |
| | | | 22, 22 | 22, 25 | 1.26:1 | With equal confidence |
| D21S11 | 28, 30.2 | 1.15:1 | 30.2, 30.2 | 28, 28 | 1:1.15 | With equal confidence |
| | | | 28, 28 | 30.2, 30.2 | 1.15:1 | With equal confidence |
| | | | 28, 30.2 | 28, 30.2 | Indeterminate | With equal confidence |

TABLE 18-continued

| Locus | Alleles in the Mixture | Peak Area Ratio Measured | LSD suggested Genotype Resolution Result ||||
|---|---|---|---|---|---|---|
| | | | Person 1 | Person 2 | Mass Ratio Calculated | Remarks |
| D18S51 | 16, 17, 18, 20 | 1.12:1.01:1.03:1 | 17, 20 | 16, 18 | 1:1.07 | With equal confidence |
| | | | 16, 18 | 17, 20 | 1.07:1 | With equal confidence |
| | | | 18, 20 | 16, 17 | 1:1.05 | With equal confidence |
| | | | 16, 17 | 18, 20 | 1.05:1 | With equal confidence |
| | | | 17, 18 | 16, 20 | 1:1.04 | With equal confidence |
| | | | 16, 20 | 17, 18 | 1.04:1 | With equal confidence |

Mixtures with mass ratios close to 1:1 are difficult to resolve, because many genotype combinations would fit equally well to the given peak data, and the slightest peak imbalance would change the best-fit genotype combination pair. For DNA mixture data with the mass ratio close to 1:1, one cannot differentiate the major and minor contributors clearly even at a 4-allele locus. As a result, the LSD method would yield multiple genotype combinations, all with comparable fit. Therefore, the LSD suggested genotype resolution result is not as clear compared with those of other sets of DNA mixture data with mass ratios other than 1:1. From Table 18, it can be seen that LSD generated at least two possible choices for each of the six loci; the true cases are indicated with shaded cells. However, when a reference profile (such as the victim's) is brought in, the right combination pair can usually be selected from the set of possible pairs. It is crucial to have a reference profile available when the underlying mass ratio is close to 1:1.

For loci VWA and TH01, each locus has three detected alleles with the ratio of the allele peak areas being close to 2:1:1. Two genotype combinations of {[A, A] [B, C]} and {[A, B] [A, C]} are possible: both would fit equally well to the peak areas ratio if the mass ratio of the DNA mixture is close to 1:1. Since there is no differentiation between the major and minor contributor, LSD suggests four possible allele assignment patterns for each of the two loci of VWA and TH01, as shown in Table 18, not being able to consistently distinguish between person 1 and person 2's profiles.

For loci D8S1179 and D21S11, each locus has two alleles with the ratio of the allele peak data close to 1:1. Since the mass ratio in the mixed DNA sample is also close to 1:1, there are three possible genotype combinations, {[A, B] [A, B]}, {[A, A] [B, B]}, and {[B, B] [A, A]}, which all give comparable allele peak signals. As a result, all three possibilities need to be considered. If the victim's profile is known, then the correct choice can usually be identified.

Since the peak area of the two alleles present at locus FGA are not comparable, the genotype combination of {[22, 25] [22, 25]} can be excluded directly. By comparing the mass ratios calculated from all possible genotype combinations at this locus with those estimated from other loci, the allele assignment pattern of {[22, 25] [22, 22]} was selected as the best-fit one.

For locus D18S51 with four alleles all with comparable peak areas, all six possible genotype combinations are ranked equally because the mass ratio in this DNA mixture sample is around 1:1. The true one is shown in the shaded cells. Since there is always some noise or imbalance associated with the allele peak quantitation, in this case, an LSD-guided analysis would be very sensitive to the relative amount of noise present in the respective allele signals. Therefore, a reference genotype becomes indispensable in assigning a decisive genotype combination pair to the two contributors.

Example 6

Using Data Reported in the Scientific Literature LSD Correctly Predicts the Genotype Profile of Each Individual that Contributed to a Mixed DNA Sample LSD was used to analyze raw data obtained from processed DNA mixtures in the scientific literature. Since both contributors' genotypes in the mixture of these reports were known, they were used to evaluate the ability of LSD to successfully predict genotypes by comparing the LSD-suggested genotype resolution with the true genotypes of both contributors.

Example 6A

DNA Mixture Data Obtained from the Report "Taking Account of Peak Areas when Interpreting Mixed DNA Profiles," by Clayton et al. (3). Table 19 Summarizes the Data Provided by Clayton et al. for Six Loci of a Mixed DNA Sample

TABLE 19

| Locus | Alleles in the Mixture | Genotype Combination ||  Allele Peak Areas |
|---|---|---|---|---|
| | | Person 1 | Person 2 | |
| VWA | 15 | 17, 19 | 15, 16 | 1247 |
| | 16 | | | 1193 |
| | 17 | | | 2279 |
| | 19 | | | 2000 |
| TH01 | 5 | 5, 7 | 7, 7 | 5735 |
| | 7 | | | 10769 |
| D8S1179 | 13 | 13, 13 | 14, 15 | 3234 |
| | 14 | | | 752 |
| | 15 | | | 894 |
| FGA | 22 | 23, 23 | 22, 23 | 534 |
| | 23 | | | 2792 |
| D21S11 | 61 | 65, 70 | 61, 77 | 373 |
| | 65 | | | 590 |
| | 70 | | | 615 |
| | 77 | | | 356 |
| D18S51 | 14 | 16, 18 | 14, 15 | 1339 |
| | 15 | | | 1465 |
| | 16 | | | 2895 |
| | 18 | | | 2288 |

Figure 19A:
FIGS. 19A and B show the output of web LSD for the DNA mixture data presented in Clayton et al. (3). All possible genotype combinations are ranked at each locus according to the magnitudes of the fitting errors.

These data were input into and analyzed by the LSD method. The results of the LSD analysis are shown in FIGS. 19A and B. The results of the data analysis are shown in Table 20.

TABLE 20

| Locus | Alleles in the Mixture | Peak Area Ratio Measured | LSD Suggested Genotype Resolution Result | | | |
|---|---|---|---|---|---|---|
| | | | Person 1 | Person 2 | Mass Ratio Calculated | Remarks |
| VWA | 15<br>16<br>17<br>19 | 1.05:1:1.91:1.68 | 15, 16 | 17, 19 | 1:1.75 | Correct |
| TH01 | 5 | 1:1.88 | 7, 7 | 5, 7 | 1:2.28 | With equal confidence |
| | 7 | | 5, 5 | 7, 7 | 1:1.88 | With equal confidence |
| D8S1179 | 13<br>14<br>15 | 4.30:1:1.19 | 14, 15 | 13, 13 | 1:1.96 | Correct |
| FGA | 22<br>23 | 1:5.23 | 22, 23 | 23, 23 | 1:2.11 | Correct |
| D21S11 | 61<br>65<br>70<br>77 | 1.05:1.66:1.73:1 | 61, 77 | 65, 70 | 1:1.65 | Correct |
| D18S51 | 14<br>15<br>16<br>18 | 1:1.09:2.16:1.71 | 14, 15 | 16, 18 | 1:1.85 | Correct |

By comparing the LSD suggested result with the true genotypes of both contributors, one can see that among the six loci, the top-ranked genotype combinations selected are consistent with that of the correct one at five loci (all but TH01). From the result at these five loci, one can see that the approximate mass ratio of the DNA mixture is around 1:2. Locus TH01 has only two alleles and post-LSD review is always required. The LSD analysis yields two possible allele assignment patterns (both of which have zero fitting residuals) with the calculated mass ratios consistent with those estimated from the other five loci. If the DNA analyst does not know the genotype of either contributor, then she cannot make the decision as to which one to choose.

Example 6B

DNA Mixture Data Obtained from the Report "Taking Account of Peak Areas When Interpreting Mixed DNA Profiles," by I. Evett et al. (21). All Available Information about this Set of DNA Mixture Data is Presented in Table 21

TABLE 21

| Locus | Alleles in the Mixture | Genotype Combination | | Allele Peak Areas |
|---|---|---|---|---|
| | | Suspect | Victim | |
| TH01 | 8<br>9.3 | 8, 9.3 | 9.3, 9.3 | 17441<br>22368 |

TABLE 21-continued

| Locus | Alleles in the Mixture | Genotype Combination | | Allele Peak Areas |
|---|---|---|---|---|
| | | Suspect | Victim | |
| D21S11 | 59<br>65<br>67<br>70 | 67, 70 | 59, 65 | 1226<br>1434<br>8816<br>8894 |
| D18S51 | 13<br>16<br>17 | 13, 13 | 16, 17 | 38985<br>1914<br>1991 |
| D8S1179 | 10<br>11<br>14 | 10, 14 | 10, 11 | 6416<br>383<br>5659 |
| VWA | 16<br>17<br>18<br>19 | 16, 18 | 17, 19 | 4669<br>931<br>4724<br>188 |
| FGA | 21<br>22<br>23 | 21, 22 | 21, 23 | 16099<br>10538<br>1014 |

Figure 20A:
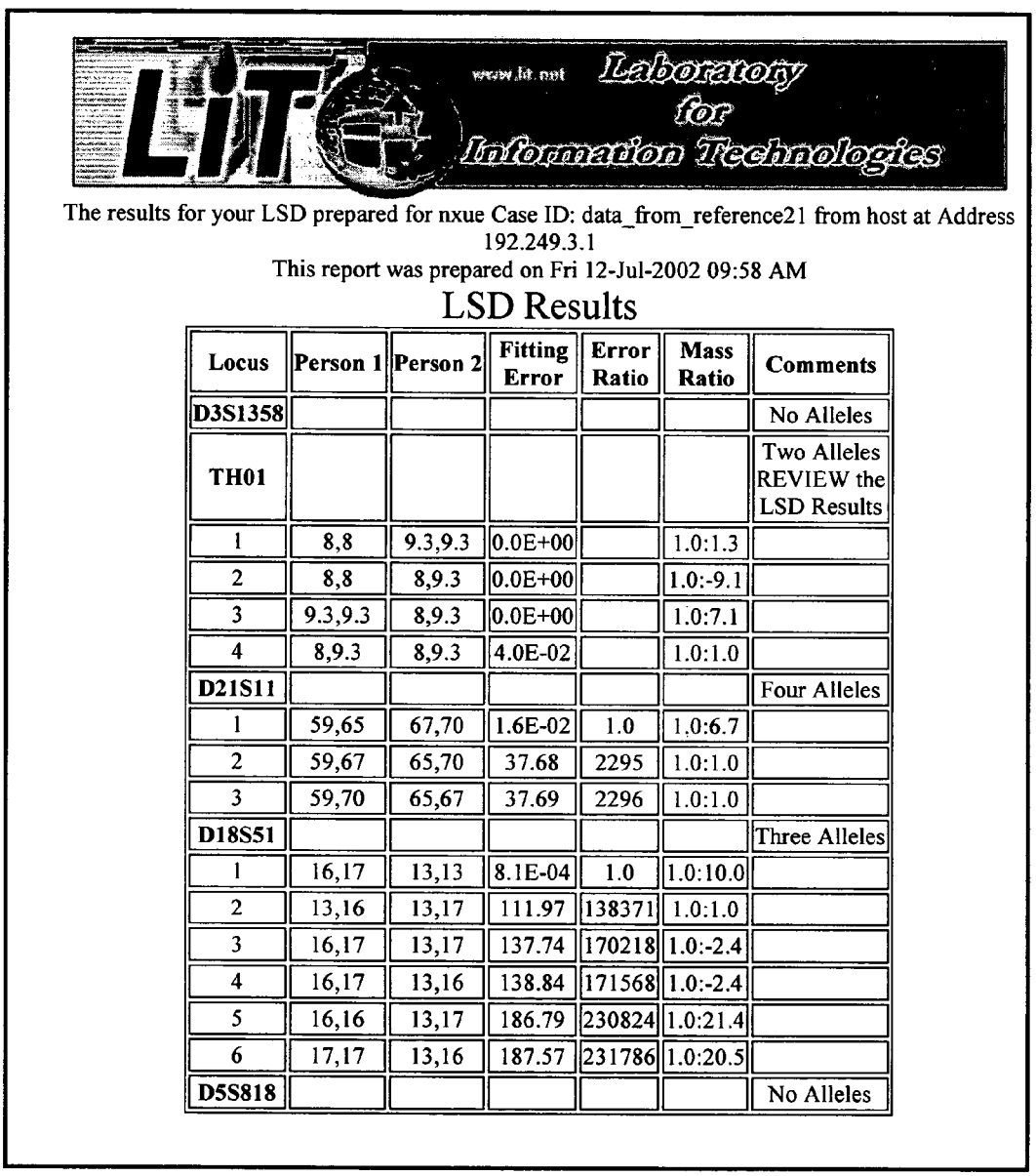
FIGS. 20A and B show the output of web LSD for the DNA mixture data presented in Evett et al. (21). All possible genotype combinations are ranked at each locus according to the magnitudes of the fitting errors.
Figure 21A:
FIGS. 21A, B, C, and D show the output of web LSD for Acadiana DNA mixture number 5. All possible genotype combinations are ranked at each locus according to the magnitudes of the fitting errors.
Figure 22A:
FIGS. 22A, B, C, and D show the output of web LSD for Acadiana DNA mixture number 1. All possible genotype combinations are ranked at each locus according to the magnitudes of the fitting errors.

The data were analyzed by the LSD method. FIGS. 20A and B show the output of the web-LSD analysis of the data. The top-ranked genotype profiles obtained using the LSD analysis are shown in Table 22.

TABLE 22

| Locus | Alleles in the Mixture | Peak Area Ratio Measured | LSD Suggested Genotype Resolution Result | | | |
|---|---|---|---|---|---|---|
| | | | Person 1 | Person 2 | Mass Ratio Calculated | Remarks |
| TH01 | 8<br>9.3 | 1:1.28 | 9.3, 9.3 | 8, 9.3 | 1:7.08 | With confidence |

TABLE 22-continued

| Locus | Alleles in the Mixture | Peak Area Ratio Measured | LSD Suggested Genotype Resolution Result | | | Remarks |
|---|---|---|---|---|---|---|
| | | | Person 1 | Person 2 | Mass Ratio Calculated | |
| D21S11 | 59<br>65<br>67<br>70 | 1:1.17:7.19:7.25 | 59, 65 | 67, 70 | 1:6.66 | With confidence |
| D18S51 | 13<br>16<br>17 | 20.37:1:1.04 | 16, 17 | 13, 13 | 1:9.98 | With confidence |
| D8S1179 | 10<br>11<br>14 | 16.75:1:1.476 | 10, 11 | 10, 14 | 1:11.39 | With confidence |
| VWA | 16<br>17<br>18<br>19 | 24.84:4.95:25.13:1 | 17, 19 | 16, 18 | 1:8.39 | With confidence |
| FGA | 21<br>22<br>23 | 15.88:10.39:1 | 21, 23 | 21, 22 | 1:4.76 | With confidence |

Although the six best-fit mass ratios calculated from the six loci are not exactly consistent, ranging from 1:4.8 (FGA) to 1:11.4 (D8S1179), this mixed DNA sample can still be resolved confidently. At each of the six loci, the genotypes of Person 1 and Person 2 correspond to the true genotypes of victim and the suspect, respectively. As a result of the noise and inconsistent PCR amplification among the six loci, there is some difference between the calculated average mass ratio of 1:8.04 and the known one prior to amplification in this DNA mixture of 1:10. However, such a difference does not affect the resolution result of the genotype profiles for the two contributors.

From the above interpretation, one can see that both of these two sets of DNA mixture data from literature reports were correctly resolved using LSD by selecting the top-ranked genotype combination with consistent mass ratio at each locus. No information about the genotype of any contributor and the mass ratio in the mixture data is necessary for LSD to resolve them. Such information was only used to verify the LSD suggested genotype resolution results.

Example 7

LSD Correctly Identifies the Genotype Profile of Contributors to DNA Mixture Samples Obtained from the Acadiana Crime Lab To further test the effectiveness of LSD, DNA mixture samples from real forensic cases were obtained and analyzed. In each instance, the mixed DNA profiles were successfully resolved using LSD.

For each mixed DNA sample the allele peaks were scanned and measured by an ABI Prism 310 Capillary Electrophoresis Gene Sequencer using Genescan and Genotyper software. The allele peak areas were measured at all 13 CODIS core loci. After applying LSD to each of the sets of data, a composite profile for each data sample was obtained by identifying the top-ranked genotype combination for each locus and choosing those with consistent mass ratios.

DNA analysts knew the genotypes of both contributors in each case. The LSD-predicted genotype profile for each contributor in the mixture was verified as correct using the known genotype profiles. The results of using LSD to resolve three of these DNA mixtures is described in Examples 7A, B, and C.

Example 7A

LSD Accurately Predicts the Genotype Profiles of Each Contributor in Acadiana DNA Mixture Number 5

Table 23 provides the allele peak data measured from thirteen loci in DNA mixture number 5. The known genotype profile of each contributor is also provided in this table.

TABLE 23

| Locus | Alleles in the Mixture | Allele Peak Heights Measured | Contributors' Genotypes | |
|---|---|---|---|---|
| | | | Suspect | Victim |
| D3S1358 | 14 | 616 | 14, 16 | 17, 19 |
| | 16 | 688 | | |
| | 17 | 3592 | | |
| | 19 | 3479 | | |
| VWA | 14 | 3483 | 14, 16 | 14, 16 |
| | 16 | 3534 | | |
| FGA | 22 | 5503 | 22, 22 | 22, 22 |
| D8S1179 | 13 | 3111 | 13, 14 | 13, 14 |
| | 14 | 3175 | | |
| D21S11 | 28 | 3166 | 29, 29 | 28, 30 |
| | 29 | 489 | | |
| | 30 | 2964 | | |
| D18S51 | 13 | 2383 | 14, 18 | 13, 15 |
| | 14 | 380 | | |
| | 15 | 2041 | | |
| | 18 | 271 | | |
| D5S818 | 11 | 538 | 11, 11 | 12, 13 |
| | 12 | 2448 | | |
| | 13 | 2240 | | |
| D13S317 | 11 | 309 | 11, 13 | 12, 14 |
| | 12 | 1892 | | |
| | 13 | 366 | | |
| | 14 | 1734 | | |
| D7S820 | 8 | 1685 | 8, 12 | 8, 10 |
| | 10 | 1409 | | |
| | 12 | 144 | | |
| D16S539 | 11 | 3047 | 12, 13 | 11, 14 |
| | 12 | 460 | | |
| | 13 | 562 | | |
| | 14 | 2329 | | |
| TH01 | 9 | 2276 | 9, 9.3 | 9, 9.3 |
| | 9.3 | 2666 | | |

TABLE 23-continued

| Locus | Alleles in the Mixture | Allele Peak Heights Measured | Contributors' Genotypes Suspect | Victim |
|---|---|---|---|---|
| TPOX | 8 | 2556 | 8, 11 | 8, 11 |
| | 11 | 2447 | | |
| CSF1PO | 10 | 1693 | 11, 12 | 10, 12 |
| | 11 | 339 | | |
| | 12 | 2164 | | |

These data were analyzed by the LSD method. The output of the web LSD application is shown in FIG. 21A-D.

The LSD predicted genotype profile of each contributor suggested by the LSD output is shown in Table 24.

TABLE 24

| Locus | Measured Alleles | Peak Area Ratio | LSD Suggested Genotype Resolution Result | | | |
|---|---|---|---|---|---|---|
| | | | Person 1 (Suspect) | Person 2 (Victim) | Mass Ratio Calculated | Remarks |
| D3S1385 | 14 | 1:1.12:5.83:5.64 | 14, 16 | 17, 19 | 1:5.42 | Correct |
| | 16 | | | | | |
| | 17 | | | | | |
| | 19 | | | | | |
| VWA | 14 | 1:1.01 | 14, 16 | 14, 16 | Indeterminate | Limitation of LSD |
| | 16 | | | | | |
| FGA | 22 | — | 22, 22 | 22, 22 | Indeterminate | One-allele case |
| D8S1179 | 13 | 1:1.02 | 13, 14 | 13, 14 | Indeterminate | Limitation of LSD |
| | 14 | | | | | |
| D21S11 | 28 | 6.47:1:6.06 | 29, 29 | 28, 30 | 1:12.54 | Correct |
| | 29 | | 28, 29 | 28, 30 | 1:7.29 | |
| | 30 | | | | | |
| D18S51 | 13 | 8.79:1.40:7.53:1 | 14, 18 | 13, 15 | 1:6.80 | Correct |
| | 141 | | | | | |
| | 5 | | | | | |
| | 18 | | | | | |
| D5S818 | 11 | 1:4.55:4.16 | 11, 11 | 12, 13 | 1:8.71 | Correct |
| | 12 | | | | | |
| | 13 | | | | | |
| D13S317 | 11 | 1:6.12:1.18:5.61 | 11, 13 | 12, 14 | 1:5.37 | Correct |
| | 12 | | | | | |
| | 13 | | | | | |
| | 14 | | | | | |
| D7S820 | 8 | 11.70:9.78:1 | 8, 12 | 8, 10 | 1:7.73 | Correct |
| | 10 | | | | | |
| | 12 | | | | | |
| D16S539 | 11 | 6.61:1:1.22:5.06 | 12, 13 | 11, 14 | 1:5.26 | Correct |
| | 12 | | | | | |
| | 13 | | | | | |
| | 14 | | | | | |
| TH01 | 9 | 1:1.17 | 9, 9.3 | 9, 9.3 | Indeterminate | Limitation of LSD |
| | 9.3 | | | | | |
| TPOX | 8 | 1.04:1 | 8, 11 | 8, 11 | Indeterminate | Limitation of LSD |
| | 11 | | | | | |
| CSF1PO | 10 | 4.99:1:6.38 | 11, 12 | 10, 12 | 1:4.54 | Correct |
| | 11 | | | | | |
| | 12 | | | | | |

Twelve of thirteen total loci are correctly resolved into composite genotype profiles for each contributor LSD. At each of the twelve loci, the genotype profile suggested by LSD corresponds to the true genotype profile of the victim and the suspect.

At loci D3S1358, D21S11, D18S51, D5S818, D13S317, D7S820, D16S539, and CSF1PO, the genotype profile is easily determined because the top-ranked genotype combination in each case has a small fitting error compared to the second ranked genotype combination, and an associated mass ratio that is consistent with the mass ratio of the other loci, approximately 1:6.26.

At locus FGA, only one allele is observed. Thus it both the victim and the perpetrator have the genotype of [22, 22] at this locus.

At each locus of loci VWA, D8S1179, TH01, and TPOX, two alleles are observed with ratios of peak areas close to 1:1. The genotype profile of each contributor is indeterminate by least squares analysis alone. However, the mass ratios of the DNA mixture sample estimated from other loci are not close to 1:1. Because none of the mass ratios for the first three genotype cases at each of these four loci is close to the majority of the best-fit mass ratios of the loci having three or four alleles, the first three cases of allele combinations may be eliminated from consideration, and the only possible genotype combination is the fourth case. At these four loci, the LSD method leads to the conclusion that both individuals have the same allele combinations of {A,B}. This is an example of the need for review of the information provided by the least squares analysis in order to obtain correct results.

At locus D21S11, the LSD method alludes to two possible choices, because the associated fitting errors are comparable. Detailed LSD ranking result for this locus is shown in Table 25.

TABLE 25

| Rank | Genotype Combinations | | Ratio of the Errors | Mass Ratio Calculated |
|---|---|---|---|---|
| | Person 1 (Suspect) | Person 2 (Victim) | | |
| 1 | 29, 29 | 28, 30 | 1 | 1:12.54 |
| 2 | 28, 29 | 28, 30 | 1.35 | 1:7.29 |
| 3 | 29, 30 | 28, 30 | 7.80 | 1:11.35 |
| 4 | 28, 28 | 29, 30 | 150.12 | 1:1.09 |
| 5 | 30, 30 | 28, 29 | 175.63 | 1:1.23 |
| 6 | 29, 30 | 28, 29 | 519.90 | 1:1.19 |

From the ranking result, one can see that both of the top two ranked genotype combinations can fit the measured allele peak data well, and the mass ratio calculated from the second ranked allele assignment (1:7.29) is more consistent with the average (1:6.26) than that calculated from the top ranked one (1:12.54). Therefore, both genotype combinations have to be considered to be the possible one. After this point, the victim's profile is brought in to compare to that of the LSD suggested result. It turned out that the perpetrator has also been identified and typed, and the first choice with person 1 being [29, 29] is the correct one. The victim is found to be LSD's Person 2. Even with the known victim's genotype of [28, 30] at this locus, one still cannot make the correct choice, because both top-ranked genotype combinations have [28, 30] as the genotype for Person 2. In actual application, we suggest that this locus be deleted from the final composite profile for the perpetrator for any follow-up consideration. The cause that the mass ratio associated with the top-ranked genotype combination is much larger than those from other loci. This imbalance in the peak areas is probably the result of imbalanced PCR amplification.

Example 7B

LSD Accurately Predicts Some Genotype Profiles of Contributors in Acadiana DNA Mixture Number 1 Despite Peak Area Saturation in the Data Readout Table 26 provides the allele peak data measured from thirteen loci in DNA mixture number 1 and the known genotype profile of each contributor.

TABLE 26

| Locus | Alleles in the Mixture | Allele Peak Heights Measured | Contributors' Genotypes | |
|---|---|---|---|---|
| | | | Person 1 (Victim) | Person 1 (Victim) |
| D3S1358 | 14 | 5786 | 15, 17 | 14, 17 |
| | 15 | 1426 | | |
| | 17 | 5578 | | |
| VWA | 15 | 5899 | 16, 19 | 15, 16 |
| | 16 | 5890 | | |
| | 19 | 1169 | | |
| FGA | 22 | 4636 | 25, 25 | 22, 24 |
| | 24 | 4765 | | |
| | 25 | 866 | | |
| D8S1179 | 11 | 6069 | 13, 15 | 11, 14 |
| | 13 | 1959 | | |
| | 14 | 4769 | | |
| | 15 | 1425 | | |
| D21S11 | 28 | 6479 | 28, 30.2 | 28, 32.2 |
| | 30.2 | 1239 | | |
| | 32.2 | 5717 | | |
| D18S51 | 16 | 1323 | 16, 16 | 17, 20 |
| | 17 | 3076 | | |
| | 20 | 2748 | | |
| D5S818 | 11 | 5354 | 11, 12 | 11, 11 |
| | 12 | 1153 | | |
| D13S317 | 8 | 5227 | 11, 12 | 8, 12 |
| | 11 | 1136 | | |
| | 12 | 5208 | | |
| D7S820 | 10 | 5913 | 10, 12 | 10, 10 |
| | 12 | 385 | | |
| D16S539 | 8 | 7082 | 10, 11 | 8, 10 |
| | 10 | 6995 | | |
| | 11 | 1300 | | |
| TH01 | 6 | 6388 | 7, 9.3 | 6, 7 |
| | 7 | 6370 | | |
| | 9.3 | 1287 | | |
| TPOX | 8 | 1393 | 8, 12 | 9, 9 |
| | 9 | 7149 | | |
| | 12 | 1219 | | |
| CSF1PO | 8 | 729 | 8, 11 | 10, 11 |
| | 10 | 4251 | | |
| | 11 | 4599 | | |

The data provided in Table 26 was analyzed by the LSD method. The output of the web LSD application is shown in FIG. 22A-D. The LSD predicted genotype profile of each contributor suggested by the LSD method is shown in Table 27.

TABLE 27

| Locus | Alleles in the Mixture | Peak Area Ratio Measured | LSD Suggested Genotype Resolution Result | | | |
|---|---|---|---|---|---|---|
| | | | Person 1 (Victim) | Person 2 (Suspect) | Mass Ratio Calculated | Remarks |
| D3S1385 | 14 | 4.06:1:3.91 | 15, 15 | 14, 17 | 1:7.97 | Wrong |
| | 15 | | | | | |
| | 17 | | | | | |
| VWA | 15 | 5.05:5.04:1 | 19, 19 | 15, 16 | 1:10.09 | Wrong |
| | 16 | | | | | |
| | 19 | | | | | |
| FGA | 22 | 5.35:5.50:1 | 25, 25 | 22, 24 | 1:10.86 | Correct |
| | 24 | | | | | |
| | 25 | | | | | |
| D8S1179 | 11 | 4.26:1.37:3.35:1 | 13, 15 | 11, 14 | 1:3.20 | Correct |
| | 13 | | | | | |
| | 14 | | | | | |
| | 15 | | | | | |
| D21S11 | 28 | 5.23:1:4.61 | 28, 30.2 | 28, 32.2 | 1:5.15 | Correct |
| | 30.2 | | | | | |
| | 32.2 | | | | | |

TABLE 27-continued

| Locus | Alleles in the Mixture | Peak Area Ratio Measured | LSD Suggested Genotype Resolution Result | | | |
|---|---|---|---|---|---|---|
| | | | Person 1 (Victim) | Person 2 (Suspect) | Mass Ratio Calculated | Remarks |
| D18S51 | 16 17 20 | 1:2.33:2.08 | 16, 16 | 17, 20 | 1:4.40 | Correct |
| D5S818 | 11 12 | 4.64:1 | 12, 12 | 11, 11 | 1:4.64 | Wrong |
| D13S317 | 8 11 12 | 4.60:1:4.58 | 11, 11 | 8, 12 | 1:9.19 | Wrong |
| D7S820 | 10 12 | 15.36:1 | 10, 12 | 10, 10 | 1:7.18 | Correct |
| D16S539 | 8 10 11 | 5.45:5.38:1 | 11, 11 | 8, 10 | 1:10.83 | Wrong |
| TH01 | 6 7 9.3 | 4.96:4.95:1 | 9.3, 9.3 | 6, 7 | 1:9.91 | Wrong |
| TPOX | 8 9 12 | 1.14:5.86:1 | 8, 12 | 9, 9 | 1:2.74 | Correct |
| CSF1PO | 8 10 11 | 1:5.83:6.31 | 8, 11 | 10, 11 | 1:6.85 | Correct |

Peak areas over 4,000 units compromise the linear relationship with DNA quantity, due to peak area saturation. Because many allele peak areas measured for this set of data are larger than 4,000 units, they cannot represent the relative mass of such alleles accurately. As a result, only profiles of seven out of a total of thirteen loci correspond to the top-ranked genotype combinations in the result.

At the other six loci, LSD analysis failed to yield the correct genotype profiles. For example: at locus VWA, the true genotypes for the two contributors are [16, 19] and [15, 16], where allele 16 is shared by both contributors and should have a larger peak area than either of the other two alleles. However, the peak areas measured at alleles 15, 16, and 19 are 5899, 5890, and 1169 respectively, where the peak area of allele 16 (5890) is not bigger than that of allele 15 (5899) at this locus. This peak area inversion is the reason that LSD's top choice does not give the correct result. For the same reason, LSD failed to yield the correct allele assignments at the other five loci: D3S1358, D5S818, D13S317, D16S539, and TH01. As for the other seven loci, in spite of allele peak-area saturation, leading to inconsistent best-fit mass ratios, the correct genotype combinations can still be obtained from the top-ranked profiles from the LSD ranking result.

Example 7C

LSD Predicted Genotype Profiles for Each Contributor in Acadiana DNA Mixture Number 2

Table 28 provides the allele peak data measured from thirteen loci in DNA mixture number 2. The known genotype profile of each contributor is also provided in this table.

TABLE 28

| Locus | Alleles in the Mixture | Allele Peak Heights Measured | Contributors' True Genotypes | |
|---|---|---|---|---|
| | | | Person 1 (Victim) | Person 2 (Suspect) |
| D3S1358 | 15 16 18 | 754 1253 551 | 16, 18 | 15, 16 |
| VWA | 14 17 | 489 1178 | 14, 17 | 17, 17 |
| FGA | 22 23 | 757 626 | 22, 23 | 22, 23 |
| D8S1179 | 11 12 15 | 513 1013 612 | 11, 12 | 12, 15 |
| D21S11 | 30 31.2 | 1108 332 | 30, 30 | 30, 31.2 |
| D18S51 | 12 17 18 | 150 415 190 | 17, 18 | 12, 17 |
| D5S818 | 10 11 | 1164 948 | 10, 11 | 10, 11 |
| D13S317 | 9 12 | 339 957 | 9, 12 | 12, 12 |
| D7S820 | 8 11 | 279 463 | 8, 11 | 11, 11 |
| D16S539 | 11 12 13 | 506 765 304 | 11, 12 | 12, 13 |
| TH01 | 7 9.3 | 1143 374 | 7, 7 | 7, 9.3 |
| TPOX | 9 10 | 809 645 | 9, 10 | 9, 10 |
| CSF1PO | 10 11 | 267 527 | 10, 11 | 11, 11 |

Figure 23A:
FIGS. 23A, B, and C show the output of web LSD for Acadiana DNA mixture number 2. All possible genotype combinations are ranked at each locus according to the magnitudes of the fitting errors.

The data provided in Table 28 was analyzed by the LSD method. The output of the web LSD application is shown in FIG. 23A-C.

The LSD predicted genotype profile of each contributor suggested by the LSD method is shown in Table 29.

TABLE 29

| Locus | Alleles in the Mixture | Peak Area Ratio Calculated | Person 1 (Victim) | Person 2 (Suspect) | Mass Ratio | Remarks |
|---|---|---|---|---|---|---|
| D3S1385 | 15 | 1.37:2.27:1 | 16, 18 | 15, 16 | 1:1.38 | True one |
|  | 16 |  |  |  |  |  |
|  | 18 |  | 15, 16 | 16, 18 | 1.38:1 |  |
| VWA | 14 | 1:2.41 | 17, 17 | 14, 17 | 1:1.42 |  |
|  | 17 |  | 14, 17 | 17, 17 | 1.42:1 | True one |
| FGA | 22 | 1.21:1 | 23, 23 | 22, 22 | 1:1.21 |  |
|  | 23 |  | 22, 22 | 23, 23 | 1.21:1 |  |
|  |  |  | 22, 23 | 22, 23 | Indeterminate | True one |
| D8S1179 | 11 | 1:1.97:1.19 | 11, 12 | 12, 15 | 1:1.21 | True one |
|  | 12 |  |  |  |  |  |
|  | 15 |  | 12, 15 | 11, 12 | 1.21:1 |  |
|  |  |  | 12, 12 | 11, 15 | 1:1.11 |  |
|  |  |  | 11, 15 | 12, 12 | 1.11:1 |  |
| D21S11 | 30 | 3.34:1 | 30, 31.2 | 30, 30 | 1:1.17 |  |
|  | 31.2 |  | 30, 30 | 30, 31.2 | 1.17:1 | True one |
| D18S51 | 12 | 1:2.77:1.27 | 12, 18 | 17, 17 | 1:1.22 |  |
|  | 17 |  | 17, 17 | 12, 18 | 1.22:1 |  |
|  | 18 |  | 12, 17 | 17, 18 | 1:1.23 |  |
|  |  |  | 17, 18 | 12, 17 | 1.23:1 | True one |
| D5S818 | 10 | 1.23:1 | 11, 11 | 10, 10 | 1:1.23 |  |
|  | 11 |  | 10, 10 | 11, 11 | 1.23:1 |  |
|  |  |  | 10, 11 | 10, 11 | Indeterminate | True one |
| D13S317 | 9 | 1:2.82 | 12, 12 | 9, 12 | 1:1.09 |  |
|  | 12 |  | 9, 12 | 12, 12 | 1.09:1 | True one |
| D7S820 | 8 | 1:1.66 | 8, 8 | 11, 11 | 1:1.66 | Wrong |
|  | 11 |  | 11, 11 | 8, 8 | 1.66:1 |  |
| D16S539 | 11 | 1.66:2.52:1 | 12, 13 | 11, 12 | 1:1.70 |  |
|  | 12 |  | 11, 12 | 12, 13 | 1.70:1 | True one |
|  | 13 |  |  |  |  |  |
| TH01 | 7 | 3.06:1 | 7, 9.3 | 7, 7 | 1:1.03 |  |
|  | 9.3 |  | 7, 7 | 7, 9.3 | 1.03:1 | True one |
| TPOX | 9 | 1.25:1 | 10, 10 | 9, 9 | 1:1.25 |  |
|  | 10 |  | 9, 9 | 10, 10 | 1.25:1 |  |
|  |  |  | 9, 10 | 9, 10 | Indeterminate | True one |
| CSF1PO | 10 | 1:1.97 | 10, 10 | 11, 11 | 1:1.97 |  |
|  | 11 |  | 11, 11 | 10, 10 | 1.97:1 |  |
|  |  |  | 11, 11 | 10, 11 | 1:2.05 |  |
|  |  |  | 10, 11 | 11, 11 | 2.05:1 | True one |

LSD guided results for this DNA mixture data suggest at least two genotype combinations for each of the thirteen loci. The calculated mass ratios at several loci are very close to 1:1. Therefore, there is no major and minor contributor, and it becomes difficult to assign which genotype to which person at each locus.

At six loci, D3S1358, VWA, D21S11, D13S317, D16S539, and TH01, the best-fit genotype combination at each locus can be selected by comparing the fitting errors and selecting combinations with consistent mass ratios.

For locus D7S820, the true genotypes of the contributors {[8, 11] [11, 11]} gave a best fitted mass ratio of 1:3, far from the best-fit mass ratio obtained at the other loci which are all less than or around 1:2. Therefore, this combination was not selected as a plausible choice. Table 30 shows the detailed LSD fitting for this locus.

TABLE 30

| Rank | Genotype Combinations | Errors | Mass Ratio Calculated |
|---|---|---|---|
| 1 | [11, 11] [8, 8] | 0 | 1:1.66 |
| 2 | [11, 11] [8, 11] | 0 | 1:3.03 |
| 3 | [8, 8] [8, 11] | 0 | 1:−5.03 |
| 4 | [8, 11] [8, 11] | 0.22 | 1:1 |

Theoretically, when the mass ratio is close to 1:1, for the genotype combination of {[8, 11] [11, 11]}, the ratio of the allele peak data should be more or less equal to 1:3. But the ratio of the allele peak data measured at this locus is 1:1.66, so the genotype combination pair of {[8, 8][11,11]} is selected with the mass ratio of 1:1.66, which is more consistent with the estimated mass ratio of 1:1.

At loci D8S1179 and D18S51, LSD fitting produced four (out of a total six) possible allele assignment patterns for each locus. The reason is that the ratio of the allele peak data measured at each locus is close to 1:2:1, and the mass ratio in the DNA mixture estimated from several loci is close to 1:1. Two possible genotype combinations can fit equally well to the allele peak data and each genotype combination can have two allele assignment patterns with person 1 and person 2 permuted. Therefore, each locus has four genotype combination patterns that need to be taken into consideration. The detailed ranking result at locus D8S1179 is shown in Table 31.

TABLE 31

| Rank | Genotype Combinations | Ratio of the Errors | Mass Ratio Calculated |
|---|---|---|---|
| 1 | [11, 12] [12, 15] | 1 | 1:1.21 |
| 2 | [12, 12] [11, 15] | 1.17 | 1:1.11 |
| 3 | [11, 11] [12, 15] | 19.23 | 1:3.17 |
| 4 | [15, 15] [11, 12] | 29.89 | 1:2.49 |
| 5 | [11, 15] [12, 15] | 66.60 | 1:3.40 |
| 6 | [11, 15] [11, 12] | 98.58 | 1:2.66 |

The errors as well as the mass ratios of the top two ranked genotype combinations are very close to each other. Therefore, it is impossible for one to make a clear decision as to which is overwhelmingly the correct choice, unless the genotype of one contributor is known.

For loci FGA, D5S818, and TPOX, each locus has only two alleles, and the ratio of the two allele peak data happens to be close to 1:1. Three allele assignment patterns can fit equally well to the allele peak data, and all of them were selected as possible choices for this locus (two of which are permuted arrangement of each other). The caseworkers would not be able to decide which one to choose, unless the genotype of one contributor is available.

For the 2-allele locus CSF1PO, since the ratio of the two allele peak areas is very close to 1:2, there are two possible allele assignment patterns at this locus: {[A, A][B, B]} and {[B, B][A, B]}, both of which would fit equally well to the measured allele peak data with comparable mass ratios. The approximate mass ratio estimated from other loci in the DNA mixture is around 1:1, which makes it difficult to differentiate the major and minor contributors. Therefore, the permuted allele assignment patterns for person 1 and person 2 of these two cases should also be taken into consideration. As a result, LSD suggests a total of four genotype combination pairs for this locus.

For this set of DNA mixture data, LSD does not suggest a very clear-cut resolution due to the close mass ratio of 1:1 However, as long as the genotype of one contributor is known, LSD is still useful in yielding the most fitting genotype profile for the other contributor. This is because it is the special combination of the genotypes of the two contributors, as stipulated by the LSD genotype combination pair that minimizes the fitting error, that is formed when fitting to the allele peak data. A genotype profile that includes only those loci that can be determined can be used in this instance.

Example 8

LSD Correctly Identifies the Genotype Profile of Contributors in DNA Mixture Samples from the Texas Department of Public Safety in Corpus Cristi To further test the functionality and effectiveness of the LSD method, five additional sets of allele peak data from forensic mixed DNA samples were run using LSD. The DNA mixture data were obtained from swabs in rape cases. The genotype of the female victim is known in each case. Sperm fraction in the mixture sample was separated from the mixture evidence by differential extraction. Therefore, genotype profiles of the male perpetrators are also obtained for all five samples. LSD was applied to the mixture data and the LSD suggested results were compared to the known genotype profiles of the two contributors. Among the five sets of data, four have peak area information at nine loci, and the fifth has information at twelve loci. Two of the five sets of DNA mixture data from Corpus Christi and the corresponding LSD suggested genotype resolution results are discussed in Examples 8A-B.

Example 8A

LSD Predicts the Genotype Profiles of Each Contributor in Texas DNA Mixture Data Number 3

Figure 24:
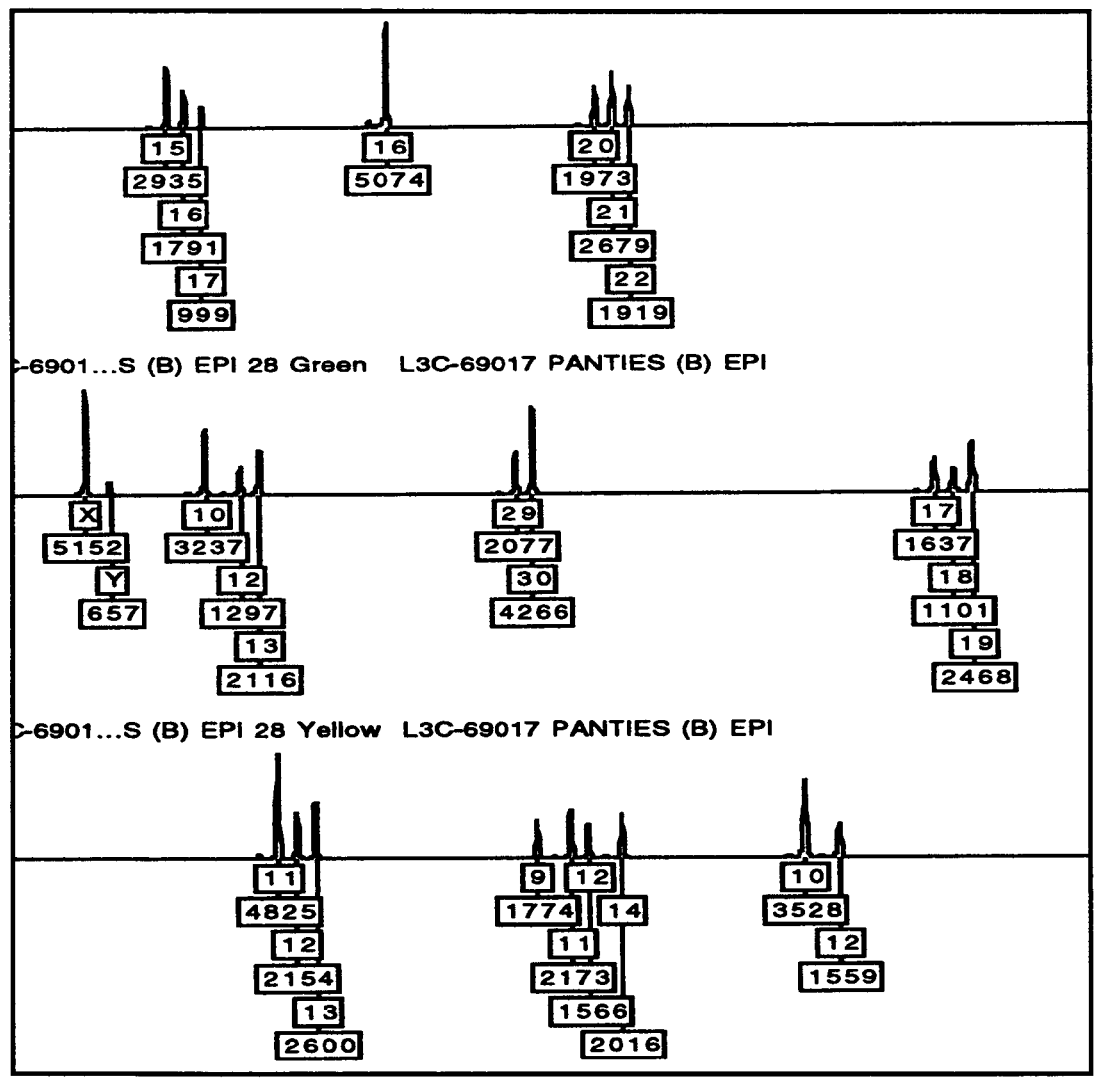
FIG. 24 shows the allele peaks at nine loci of the Texas DNA mixture data number 3; both the allele names and the corresponding peak areas are indicated.

The electropherogram showing the allele peak data at nine loci for Texas DNA mixture number 3 is shown in FIG. 24. The peak area data extracted from the electropherogram and the known genotype profiles of the female victim and male suspect are shown in Table 32.

TABLE 32

| Locus | Alleles in the Mixture | Allele Peak Areas Measured | Contributors' Genotypes | |
|---|---|---|---|---|
| | | | Female Victim | Male Suspect |
| D3S1358 | 15 | 2935 | 15, 16 | 15, 17 |
| | 16 | 1791 | | |
| | 17 | 999 | | |
| VWA | 16 | 5074 | 16, 16 | 16, 16 |
| FGA | 20 | 1973 | 20, 22 | 21, 21 |
| | 21 | 2679 | | |
| | 22 | 1919 | | |
| D8S1179 | 10 | 3237 | 10, 13 | 10, 12 |
| | 12 | 1297 | | |
| | 13 | 2116 | | |
| D21S11 | 29 | 2077 | 29, 30 | 30, 30 |
| | 30 | 4266 | | |
| D18S51 | 17 | 1637 | 17, 19 | 18, 19 |
| | 18 | 1101 | | |
| | 19 | 2468 | | |
| D5S818 | 11 | 4825 | 11, 13 | 11, 12 |
| | 12 | 2154 | | |
| | 13 | 2600 | | |
| D13S317 | 9 | 1774 | 11, 14 | 9, 12 |
| | 11 | 2173 | | |
| | 12 | 1566 | | |
| | 14 | 2016 | | |
| D7S820 | 10 | 3528 | 10, 12 | 10, 10 |
| | 12 | 1559 | | |

Figure 25A:
FIGS. 25A, B, and C show the output of web LSD for Texas DNA mixture number 3. All possible genotype combinations are ranked at each locus according to the magnitudes of the fitting errors.

The data provided in Table 32 were analyzed by the LSD method. The output of the web LSD application is shown in FIG. 25A-C.

The LSD predicted genotype profile of each contributor suggested by the LSD method is shown in Table 33.

TABLE 33

| Locus | Alleles in the Mixture | Peak Area Ratio Measured | LSD Suggested Genotype Resolution Result ||||
|---|---|---|---|---|---|---|
| | | | Person 1 (Suspect) | Person 2 (Victim) | Mass Ratio Calculated | Remarks |
| D3S1385 | 15 | 2.94: | 15, 17 | 15, 16 | 1:1.76 | True one |
| | 16 | 1.79: | | | | |
| | 17 | 1 | | | | |
| VWA | 16 | — | 16, 16 | 16, 16 | Indeterminate | True one |
| FGA | 20 | 1.02: | 21, 21 | 20, 22 | 1:1.45 | True one |
| | 21 | 1.40: | | | | |
| | 22 | 1 | | | | |
| D8S1179 | 10 | 2.50: | 10, 12 | 10, 13 | 1:1.66 | True one |
| | 12 | 1: | | | | |
| | 13 | 1.63 | | | | |
| D21S11 | 29 | 1; | 30, 30 | 29, 30 | 1:1.89 | True one |
| | 30 | 2.05 | 29, 29 | 30, 30 | 1:2.05 | |
| D18S51 | 17 | 1.49: | 18, 19 | 17, 19 | 1:1.53 | True one |
| | 18 | 1: | | | | |
| | 19 | 2.24 | | | | |
| D5S818 | 11 | 2.24: | 11, 12 | 11, 13 | 1:1.20 | True one |
| | 12 | 1: | | | | |
| | 13 | 1.21 | | | | |
| D13S317 | 9 | 1.13: | 9, 12 | 11, 14 | 1:1.25 | True one |
| | 11 | 1.39: | | | | |
| | 12 | 1 | | | | |
| | 14 | 1.29 | | | | |
| D7S820 | 10 | 2.263: | 10, 10 | 10, 12 | 1:1.58 | True one |
| | 12 | 1 | 12, 12 | 10, 10 | 1:2.26 | |

Among the nine loci, seven have 3 or 4 alleles per locus and the top-ranked genotype profiles for the two contributors correspond to the true genotypes.

At each of the remaining 2-allele loci, D21S11 and D7S820, two possible choices are selected because both choices in each locus give a mass ratio consistent with those for other loci. The ratio of the allele peak areas measured at each locus is close to 1:2 and the approximate mass ratio in this mixed DNA sample can also be close to 1:2 as predicted from the other loci. Thus two genotype combinations are possible with consistent mass ratios across both loci, and both fit equally well to the allele peak data measured, as shown in Table 33. Only one of these two is consistent with the true genotypes of the female victim and the male perpetrator. Therefore, when the victim's genotype's is brought in to resolve the choices, one would choose the one where person 2's profile agrees with that of the known victim's profile. Those are given as the shaded cells in Table 33.

The best-fit mass ratios across the nine loci are consistent with each other, ranging from 1:1.20 (d5S818) to 1:1.76 (D3S1358).

This set of mixture sample was successfully resolved at all loci. The victim's profile was used at two 2-allele loci to help select between two alternative genotype combination choices.

Example 8B

LSD Predicts the Genotype Profiles of Each Contributor in Texas DNA Mixture Data Number 4

Figure 26:
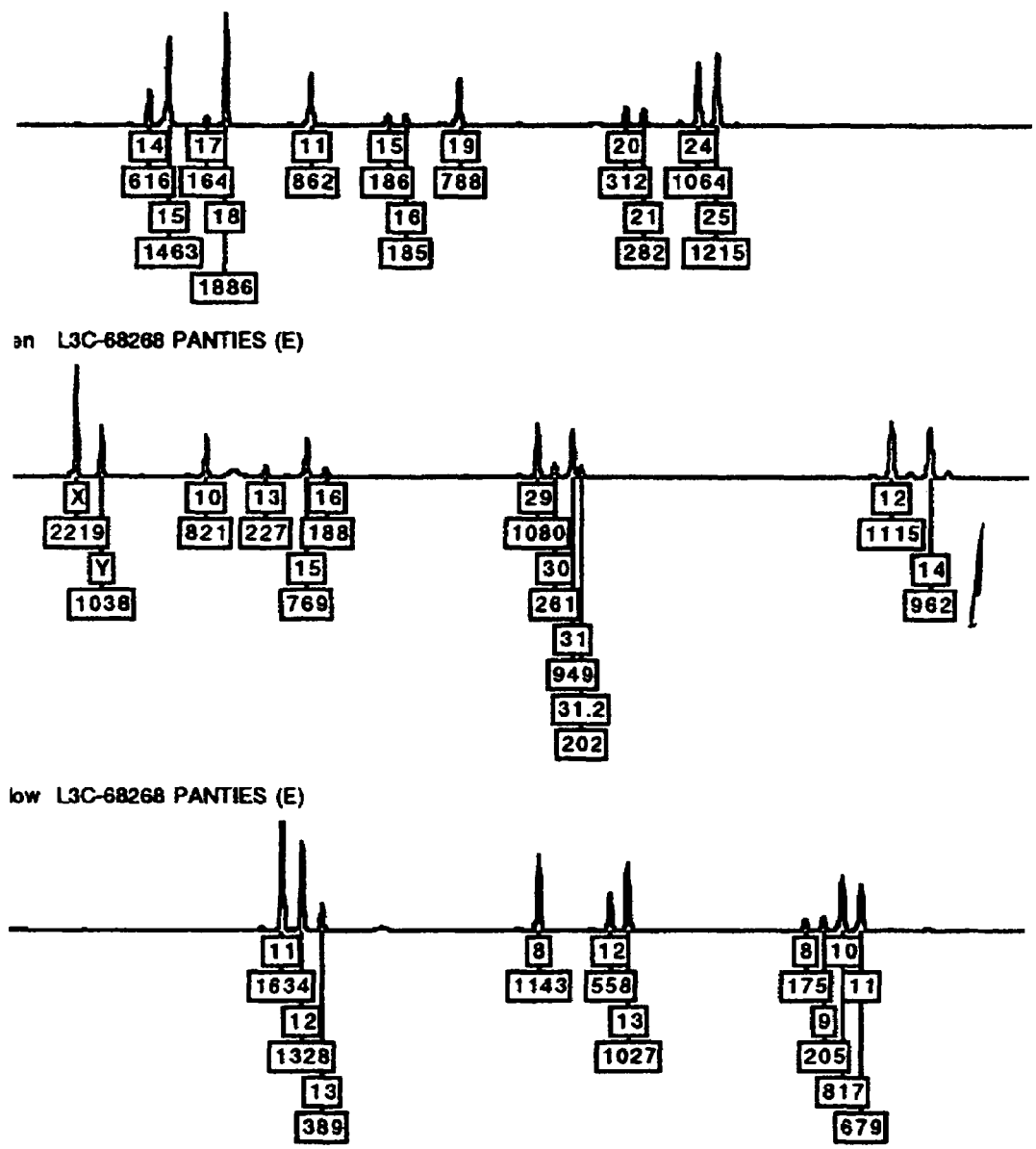
FIG. 26 shows the allele peaks at nine loci of the Texas DNA mixture data number 4; both the allele names and the corresponding peak area are indicated.

The electropherogram showing the allele peak data at nine loci for Texas DNA mixture number 4 is shown in FIG. 26. The peak area data extracted from the electropherogram and the known genotype profiles of the female victim and male suspect are shown in Table 34.

TABLE 34

| Locus | Alleles in the Mixture | Allele Peak Areas Measured | Contributors' Genotypes ||
|---|---|---|---|---|
| | | | Female Victim | Male suspect |
| D3S1358 | 14 | 616 | 14, 18 | D3S1358 |
| | 15 | 1463 | | |
| | 18 | 1886 | | |
| VWA | 11 | 862 | 15, 16 | VWA |
| | 15 | 186 | | |
| | 16 | 185 | | |
| | 19 | 788 | | |
| FGA | 20 | 312 | 20, 21 | FGA |
| | 21 | 282 | | |
| | 24 | 1064 | | |
| | 25 | 1215 | | |
| D8S1179 | 10 | 821 | 13, 16 | D8S1179 |
| | 13 | 227 | | |
| | 15 | 769 | | |
| | 16 | 188 | | |
| D21S11 | 29 | 1080 | 30, 31.2 | D21S11 |
| | 30 | 261 | | |
| | 31 | 949 | | |
| | 31.2 | 202 | | |
| D18S51 | 12 | 1115 | 12, 14 | D18S51 |
| | 14 | 962 | | |

TABLE 34-continued

| Locus | Alleles in the Mixture | Allele Peak Areas Measured | Contributors' Genotypes Female Victim | Male suspect |
|---|---|---|---|---|
| D5S818 | 11 | 634 | 11, 13 | D5S818 |
|  | 12 | 328 |  |  |
|  | 13 | 389 |  |  |
| D13S317 | 8 | 1143 | 12, 12 | D13S317 |
|  | 12 | 558 |  |  |
|  | 13 | 1027 |  |  |
| D7S820 | 8 | 175 | 8, 9 | D7S820 |
|  | 9 | 205 |  |  |
|  | 10 | 817 |  |  |
|  | 11 | 679 |  |  |

Figure 27A:
FIGS. 27A, B, and C show the output of web LSD for Texas DNA mixture number 4. All possible genotype combinations are ranked at each locus according to the magnitudes of the fitting errors.

The data were analyzed by the LSD method. The web-output of the data after LSD analysis is shown in FIG. 27A-C. The LSD predicted genotype profile of each contributor suggested by the LSD method is shown in Table 35.

possible genotype combination profiles have zero fitting errors. The best fitting mass ratios calculated from these three possible combinations are 1:1.2, 1:−14.6, and 1:12.6, none of which are consistent with those calculated from the other eight loci. Therefore, none is selected as a possible choice for this locus. Since the ratio of the allele peak areas measured at this locus is 1.16:1, which is very close to 1:1, the genotype combination of {[12, 14][12, 14]} is considered as the possible choice. This combination was chosen in this instance, and it is the correct choice.

LSD is able to resolve DNA mixtures from the Acadiana Crime Lab and the Texas Department of Public Safety in Corpus Christi into the genotype profile of the two contributors. From these data it is apparent that as long as the allele peak data in a sample reflect the relative mass proportion of the alleles in the mixture, LSD will yield the true genotype profiles for the two contributors as its top-ranked profiles.

TABLE 35

| Locus | Alleles in the Mixture | Peak Area Ratio Measured | LSD Suggested Genotype Resolution Result Person 1 (Victim) | Person 2 (Suspect) | Mass Ratio Calculated | Remarks |
|---|---|---|---|---|---|---|
| D3S1385 | 14 | 1:2.38:3.06 | 14, 18 | 15, 18 | 1:2.54 | True one |
|  | 15 |  |  |  |  |  |
|  | 18 |  |  |  |  |  |
| VWA | 11 | 4.66:1.01:1:4.26 | 15, 16 | 11, 19 | 1:4.45 | True one |
|  | 15 |  |  |  |  |  |
|  | 16 |  |  |  |  |  |
|  | 19 |  |  |  |  |  |
| FGA | 20 | 1.11:1:3.77:4.31 | 20, 21 | 24, 25 | 1:3.84 | True one |
|  | 21 |  |  |  |  |  |
|  | 24 |  |  |  |  |  |
|  | 25 |  |  |  |  |  |
| D8S1179 | 10 | 4.37:1.21 | 13, 16 | 10, 15 | 1:3.83 | True one |
|  | 13 |  |  |  |  |  |
|  | 15 |  |  |  |  |  |
|  | 16 |  |  |  |  |  |
| D21S11 | 29 | 5.35:1.29:4.70:1 | 30, 31.2 | 29, 31 | 1:4.38 | True one |
|  | 30 |  |  |  |  |  |
|  | 31 |  |  |  |  |  |
|  | 31.2 |  |  |  |  |  |
| D18S51 | 12 | 1.16:1 | 12, 14 | 12, 14 | Indeterminate | True one |
|  | 14 |  |  |  |  |  |
| D5S818 | 11 | 4.20:3.41:1 | 11, 13 | 11, 12 | 1:3.60 | True one |
|  | 12 |  |  |  |  |  |
|  | 13 |  |  |  |  |  |
| D13S317 | 8 | 2.05:1:1.84 | 12, 12 | 8, 13 | 1:3.89 | True one |
|  | 12 |  |  |  |  |  |
|  | 13 |  |  |  |  |  |
| D7S820 | 8 | 1:1.17:4.67:3.88 | 8, 9 | 10, 11 | 1:3.94 | True one |
|  | 9 |  |  |  |  |  |
|  | 10 |  |  |  |  |  |
|  | 11 |  |  |  |  |  |

From the summary of the LSD-suggested genotype resolution result shown in Table 35, it is clear that all nine loci are resolved correctly and unambiguously, where the top-ranked genotype combinations selected by LSD are consistent with the true genotype profiles of the two contributors at all nine loci. The mass ratios calculated from the nine loci are also consistent, ranging from 1:2.54 (D3S1358) to 1:4.45 (VWA).

Deconvolution at locus D18S51 warrants further discussion. D18S51 has two alleles and, as always, three of the four Therefore, the LSD method is a feasible, powerful, and highly useful tool in resolving DNA mixture samples of two people.

Example 9

LSD is a More Accurate Method to Resolve a DNA Mixture into Genotype Profiles of Contributors than Linear Mixture Analysis (LMA)

Linear Mixture Analysis (LMA) is a recently published algorithm that attempts to resolve DNA mixtures. LMA, like LSD, uses quantitative allele peak data and linear algebra principals to solve the DNA mixture problem. LSD is a more flexible method for solving for the most fitting genotype profile for individual contributors in the mixture. LSD operates locus by locus to fit each locus separately, followed by pulling together only those loci at which resolution is clear and consistent to form a composite profile for each of the two contributors. In LMA, all available loci are processed as one entity, and a single mass ratio is sought to fit the given allele peak data simultaneously at all loci.

When LMA is used to resolve a two-people DNA mixture, the genotype of one of the two contributors also has to be known, and entered into the LMA algorithm to derive the other contributor's genotype. When using LSD to resolve such mixed DNA profiles, no a priori genotype information is necessary. The best-fit genotype combination pair for both contributors is obtained simultaneously in one step.

To verify that the LSD method is more accurate than the LMA method, data from a DNA mixture was resolved into genotype profiles using both methods. The results of each method were then compared to the known genotype profile of each contributor.

The data for the mixture of DNA used to test the accuracy of the LSD and LMA methods is shown in Table 36.

TABLE 36

| Locus | Alleles in the Mixture | Genotype Combination Suspect | Genotype Combination Victim | Allele Peak Areas |
|---|---|---|---|---|
| TH01 | 8 | 8, 9.3 | 9.3, 9.3 | 17441 |
|  | 9.3 |  |  | 22368 |
| D21S11 | 59 | 67, 70 | 59, 65 | 1226 |
|  | 65 |  |  | 1434 |
|  | 67 |  |  | 8816 |
|  | 70 |  |  | 8894 |
| D18S51 | 13 | 13, 13 | 16, 17 | 38985 |
|  | 16 |  |  | 1914 |
|  | 17 |  |  | 1991 |
| D8S1179 | 10 | 10, 14 | 10, 11 | 6416 |
|  | 11 |  |  | 383 |
|  | 14 |  |  | 5659 |
| VWA | 16 | 16, 18 | 17, 19 | 4669 |
|  | 17 |  |  | 931 |
|  | 18 |  |  | 4724 |
|  | 19 |  |  | 188 |
| FGA | 21 | 21, 22 | 21, 23 | 16099 |
|  | 22 |  |  | 10538 |
|  | 23 |  |  | 1014 |

Both the LMA and LSD methods were used to resolve the DNA mixtures into the genotype profile of each contributor. Table 37 shows the genotype profiles of the contributors resolved using the LSD method.

TABLE 37

| Locus | Alleles in the Mixture | Peak Area Ratio Measured | LSD Suggested Genotype Resolution Result Person 1 | Person 2 | Mass Ratio Calculated | Remarks |
|---|---|---|---|---|---|---|
| TH01 | 8 | 1:1.28 | 9.3, 9.3 | 8, 9.3 | 1:7.08 | With confidence |
|  | 9.3 |  |  |  |  |  |
| D21S11 | 59 | 1:1.17:7.19:7.25 | 59, 65 | 67, 70 | 1:6.66 | With confidence |
|  | 65 |  |  |  |  |  |
|  | 67 |  |  |  |  |  |
|  | 70 |  |  |  |  |  |
| D18S51 | 13 | 20.37:1:1.04 | 16, 17 | 13, 13 | 1:9.98 | With confidence |
|  | 16 |  |  |  |  |  |
|  | 17 |  |  |  |  |  |
| D8S1179 | 10 | 16.75:1:1.476 | 10, 11 | 10, 14 | 1:11.39 | With confidence |
|  | 11 |  |  |  |  |  |
|  | 14 |  |  |  |  |  |
| VWA | 16 | 24.84:4.95:25.13:1 | 17, 19 | 16, 18 | 1:8.39 | With confidence |
|  | 17 |  |  |  |  |  |
|  | 18 |  |  |  |  |  |
|  | 19 |  |  |  |  |  |
| FGA | 21 | 15.88:10.39:1 | 21, 23 | 21, 22 | 1:4.76 | With confidence |
|  | 22 |  |  |  |  |  |
|  | 23 |  |  |  |  |  |

The LSD result shown in Table 37 correctly predicts the genotype profile for each contributor at all six loci. It is worth noting that the best-fit mass ratio calculated for the six loci varies from 1:4.76 (FGA) to 1:11.39 (D8S1179). This variation does not affect the ability of the LSD method to correctly predict the genotype profiles of the contributors.

Table 38 provides the genotype profiles predicted using the LMA method of analysis.

TABLE 38

| Locus | Alleles in the Mixture | Normalized Allele Peak Areas | Genotype of Person A Assumed Known | | LSD Suggested Result for Person B | | |
|---|---|---|---|---|---|---|---|
| | | | Alleles | Vector $g_A$ | Vector $g_B$ | | Alleles |
| TH01 | 8 | 0.88 | 8 | $\begin{bmatrix} 1 \end{bmatrix}$ | $\begin{bmatrix} 0.14 \end{bmatrix}$ | $\begin{bmatrix} 0 \end{bmatrix}$ | 9.3 |
| | 9.3 | 1.12 | 9.3 | 1 | 1.86 | 2 | |
| D21S11 | 59 | 0.12 | 67 | 0 | 0.86 | 1 | 59 |
| | 65 | 0.14 | 70 | 0 | 1.00 | 1 | 65 |
| | 67 | 0.87 | | 1 | 0.07 | 0 | |
| | 70 | 0.87 | | 1 | 0.07 | 0 | |
| D18S51 | 13 | 1.82 | 13 | 2 | 0.71 | 1 | 13 |
| | 16 | 0.09 | | 0 | 0.64 | 1 | 16 |
| | 17 | 0.09 | | 0 | 0.64 | 1 | 17 |
| D8S1179 | 10 | 1.03 | 10 | 1 | 1.21 | 1 | 10 |
| | 11 | 0.06 | 14 | 0 | 0.43 | 0 | |
| | | | | 1 | 0.36 | 0 | |
| VWA | 14 | 0.91 | | 1 | 0.21 | 0 | |
| | 16 | 0.89 | 16 | 0 | 1.29 | 1 | 17 |
| | 17 | 0.18 | 18 | 1 | 0.29 | 0 | |
| | 18 | 0.90 | | 0 | 0.21 | 0 | |
| FGA | 19 | 0.03 | | 1 | 2.14 | 2 | |
| | 21 | 1.16 | 21 | 1 | -0.71 | -1 | 21 |
| | 22 | 0.76 | 22 | 0 | 0.05 | 1 | 21 |
| | 23 | 0.07 | | | | | 23 |

The LMA method only resolves two of the six loci correctly. The shaded boxes in the table indicate the incorrectly resolved loci.

A second set of DNA mixture sample data was used to compare the effectiveness of LMA and LSD in resolving 2-people mixtures. The data used to perform these analysis are shown in Table 39. The data were provided by the Promega Corporation and have a known mass ratio of 9:1 prior to PCR. The known genotype of both contributors are also shown and were used to verify the resolution results.

TABLE 39

| | Alleles in the | Ratio of Allele Peak | True Genotypes | |
|---|---|---|---|---|
| Locus | Mixture | Data | Person 1 | Person 2 |
| TH01 | 6, 9, 9.3 | 19.79:1:1.19 | 6, 6 | 9, 9.3 |
| D18S51 | 12, 13, 15, 17 | 14.23:1.40:11.34:1 | 12, 15 | 13, 17 |
| D5S818 | 10, 11, 12 | 3.08:1:2.97 | 10, 12 | 11, 11 |
| D13S17 | 9, 10, 11 | 1:5.65:5.10 | 10, 11 | 9, 10 |
| D7S820 | 9, 11, 12 | 54.10:1.94:1 | 9, 9 | 11, 12 |
| CSF1PO | 10, 11, 12 | 1:11.74:12.42 | 11, 12 | 10, 12 |
| VWA | 15, 17, 18 | 3.89:1:4.28 | 15, 18 | 17, 17 |
| D8S1179 | 12, 13, 15 | 4.40:1:3.99 | 12, 15 | 13, 13 |
| FGA | 21, 24, 25 | 10.58:12.76:1 | 21, 24 | 24, 25 |

The LSD suggested genotype resolution results are presented in Table 40.

TABLE 40

| | | LSD Suggested Genotype Resolution Result | | |
|---|---|---|---|---|
| Locus | Alleles in the Mixture | Person 1 | Person 2 | Mass Ratio Calculated |
| TH01 | 6, 9, 9.3 | 6, 6 | 9, 9.3 | 9.0:1 |
| D18S51 | 12, 13, 15, 17 | 12, 15 | 13, 17 | 10.7:1 |
| D5S818 | 10, 11, 12 | 10, 12 | 11, 11 | 6.0:1 |
| D13S17 | 9, 10, 11 | 10, 11 | 9, 10 | 5.8:1 |
| D7S820 | 9, 11, 12 | 9, 9 | 11, 12 | 18.4:1 |
| CSF1PO | 10, 11, 12 | 11, 12 | 10, 12 | 13.0:1 |
| VWA | 15, 17, 18 | 15, 18 | 17, 17 | 8.1:1 |
| D8S1179 | 12, 13, 15 | 12, 15 | 13, 13 | 8.4:1 |
| FGA | 21, 24, 25 | 21, 24 | 24, 25 | 7.9:1 |

Table 40 shows that all nine loci are correctly resolved by pulling out the top-ranked genotype combination pair at each locus. Note that the optimal mass ratio calculated for each locus varies somewhat from locus to locus, ranging from 5.8:1 to 18:4:1, and the average being 9.7:1, which is very close to the known mass ratio prior to amplification.

In contrast, results from using the LMA algorithm, shown in Table 41, indicate that only seven out of nine loci were correctly resolved.

TABLE 41

| Locus | Alleles in the Mixture | Normalized Allele Peak Areas | Genotype of Person A Assumed Known | | LMA Suggested Result for Person B | | True Genotype of Person B |
|---|---|---|---|---|---|---|---|
| | | | Alleles | Vector $g_A$ | Vector $g_B$ | Alleles | |
| TH01 | 6 | 1.800: | 6 | ⎡ 2 ⎤ | ⎡ 0.33 ⎤ | 9 | 9 |
| | 9 | 0.091: | | 0 | 0.76 | 9.3 | 9.3 |
| | 9.3 | 0.108 | | - | 0.90 | | |
| D18S51 | 12 | 1.017: | 12 | 1 | 1.14 | 12 | 13 |
| | 13 | 0.100: | | 0 | 0.83 | 13 | 17 |
| | 15 | 0.811: | 15 | 1 | -0.58 | 17 | |
| | 17 | 0.072 | | 0 | 0.60 | | |
| | | | | - | -0.03 | 11 | 11 |
| D5S818 | 10 | 0.876: | 10 | 0 | | | |
| | 11 | 0.284: | | 1 | 2.37 | 11 | 11 |
| D13S17 | 12 | 0.840 | 12 | - | -0.33 | | |
| | 9 | 0.170: | | 0 | 1.42 | 9 | 9 |
| | 10 | 0.962: | 10 | 1 | 0.68 | 10 | 10 |
| | 11 | 0.868 | 11 | 1 | -0.10 | | |
| D7S820 | 9 | 1.897: | 9 | - | 1.14 | | |
| | 11 | 0.068: | | 2 | 0.57 | 9 | 11 |
| | 12 | 0.035 | | 0 | 0.29 | 11 | 12 |
| CSF1PO | 10 | 0.080 | | 0 | 0.66 | | |
| | 11 | 0.933: | 11 | - | 0.44 | 10 | 10 |
| | 12 | 0.987 | 12 | 0 | 0.89 | 12 | 12 |
| VWA | 15 | 0.858: | 15 | 1 | -0.18 | | |
| | 17 | 0.220: | | 1 | 1.83 | 17 | 17 |
| D8S1179 | 18 | 0.922 | 18 | - | 0.35 | 17 | 17 |
| | 12 | 0.937: | 12 | 1 | 0.48 | | |
| | 13 | 0.213: | | 0 | 1.78 | | |
| FGA | 15 | 0.850 | 15 | 1 | -0.25 | 13 | 13 |
| | 21 | 0.869: | 21 | - | -0.09 | 13 | 13 |
| | 24 | 1.048: | 24 | 1 | 1.40 | | |
| | 25 | 0.082 | | ⎣ 0 ⎦ | ⎣ 0.68 ⎦ | 24 | 24 |
| | | | | | | 25 | 25 |

The LMA genotype resolution results at loci D18S51 and D7S820 are not correct. Note that these two loci correspond to those loci, from LSD, to have the best-fit mass ratio the most removed from the average ratio of 9.7:1, indicating the imposed fit used by the LMA approach for these loci is a poor fit, although it appear to be a good fit for other loci.

From these two examples, it appears that LMA is not as accurate as LSD in resolving mixed DNA samples.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

REFERENCES

1 J. Samuels and C. Asplen, *The Future of Forensic DNA Testing: Predictions of the Research and Development Working Group*, The National Institute of Justice, November, 2000.

2 National Research Council, *The Evaluation of Forensic DNA Evidence*, National Academy Press, 1996.

3 T. Clayton, J. Whitaker, R. Sparkes, and P. Gill, "Analysis and Interpretation of Mixed Forensic Stains Using DNA STR Profiling," *Forensic Science International*, 91 (1998): 55-70.

4 J M. Curran, C M. Triggs, J. Buckleton, and B S. Weir, "Interpreting DNA Mixtures in Structured Populations," *Journal of Forensic Science*, 44-5 (1999): 987-995.

5 P. Gill, R. Sparkes, R. Pinchin, T. Clayton, J. Whitaker, and J. Buckleton, "Interpreting Simple STR Mixtures Using Allele Peak Areas," *Forensic Science International*, 91 (1998): 41-53.

6 T. Wang, N. Xue, M. Radar, and J. D. Birdwell, "Least Square Deconvolution (LSD) of Mixture STR/DNA Using Peak Area/Height Data," The 7$^{th}$ CODIS User's Conference, Arlington, Va., October, 2001.

7 M. Farley and J. Harrington, *Forensic DNA Technology*, Lewis Publishers, INC., 1991.

8 K. Inman and N. Rudin, *An Introduction to Forensic DNA Analysis*, CRC Press, 1997.

9 P. Gill, J. Whitaker, C. Flaxman, N. Brown, and J. Buckleton, "An Investigation of the Rigor of Interpretation Rules for STRs Derived from Less Than 100 pg of DNA," *Forensic Science International*, 112 (2000): 17-40.

10 J. Butler, Forensic *DNA Typing*, Academic Press, 2001.

11 B. Budowle, "Probabilities of Alleles' Distribution at 13 Loci", Personal Communication in October 1997.

12 P. Gill, R. sparkes, and C. Kimpton, "Development of Guidelines to Designate Alleles Using an STR Multiplex System," *Forensic Science International*, 89 (1997): 185-197.

13 B. Brown, Director of FBI National CODIS Project, Personal Communication in January, 2002.

14 P. Billings, *DNA on Trial, Genetic Identification and Criminal Justice*, Cold Spring Harbor Laboratory Press, 1992.

15 I. Evett, and B. Weir, *Interpreting DNA Evidence, Statistical Genetics for Forensic Scientists*, Sinauer Associates Inc., 1998.

16 G. Strang, *Linear Algebra and Its Applications* (*Third edition*), Harcourt Brace Jovanovich College Publisher, 1986.
17 J. Birdwell, "Analysis of Forensic Mixtures," *LIT/FBI Weekly Seminar Series to Project Team Members*, Apr. 27, 2001.
18 M. Perlin and B. Szabady, "Linear Mixture Analysis: A Mathematical Approach to Resolving Mixed DNA Samples," *Journal of Forensic Science*, 46-6 (2001): 1372-1378.
19 P. Graham, "Allele Peak Data of DNA Mixture from Real Cases," Texas Department of Public Safety, Corpus Christi, October, 2001.
20 "Web-LSD Software: Restricted database, Developed by Laboratory for Information Technologies, the University of Tennessee, Knoxville, May, 2002.
21 I. Evett, P, Gill, and J. Lambert, "Taking Account of Peak Areas When Interpreting Mixed DNA Profiles," *Journal of Forensic Science*, 43-6 (1998): 62-69.
22 R. Wickenheiser, "Allele Peak Data of DNA Mixture from Real Cases," Acadiana Crime Laboratory, Louisiana, September, 2001.
23 P. Newman, "Allele Peak Data of DNA Mixture", Promega Corporation, September, 2001.
24 Personal Communication with DNA analysts around the country and through our work in resolving mixed DNA samples.
25. T. Wang, "Guidelines and Rules for Interpreting Least Square Deconvolution (LSD) Output Results", University of Tennessee, Sep. 15, 2002.

What is claimed is:

1. A computer implemented method of accessing a DNA database from a software application installed and operated on a computer server, the computer server for resolving a mixture of DNA of at least two contributors comprising:
   hosting said software application on said computer server, said computer server programmed to perform said software application for resolving a DNA mixture of at least two contributors comprising a computer implemented resolution methods, said software application computer server programmed to perform:
   solving a peak fit ratio for each possible allele combination at a first locus;
   calculating a fitting residual for each possible allele combination; and
   selecting an allele combination of the possible allele combinations, having a small fitting residual, for a source of DNA mixture at the first locus;
   said software application computer server permitting access by said software application to said DNA database;
   receiving DNA mixture data at the software application computer server; and
   computing analysis results on the software application computer server for resolving the mixture of the at least two contributors to select said allele combination having said small fitting residual.

2. The method of claim 1 wherein the software application computer server is a secure server.

3. The method of claim 1 wherein the software application computer server is protected by a firewall.

4. The method of claim 1 that further comprises displaying the analysis results at a client computer connected to said software application computer server.

5. The method of claim 1 further comprising determining at said software application computer server potential match contributor data from a DNA database, the DNA database maintaining data for possible contributors for said DNA mixture data.

6. The method of claim 1 further comprising matching said analysis results at said software application computer server to DNA data in another DNA database to find a profile corresponding to a possible contributor matching at least a portion of said analysis results.

7. The method of claim 6 wherein determining if there is a match of a portion of said DNA mixture data comprises matching allele data at said software application computer server.

8. The method of claim 1 further comprising receiving DNA profile data of at least one contributor at a client computer connected to said software application computer server.

9. The method of claim 6 further comprising storing a portion of DNA data at a client computer of the other DNA database.

10. The method of claim 1 further comprising inputting allele peak data for alleles present at the first locus of a plurality of loci in the DNA mixture.

11. The method of claim 10 wherein the allele peak data comprise measurements of peak heights.

12. The method of claim 1 wherein the fitting residual for a possible allele combination comprises a sum of squared differences between components of a quantitative allele peak data vector and components of a predicted allele peak data vector.

13. The method of claim 1 wherein the first locus is selected from the group consisting of CSF1PO, FGA, TH01, TPOX, VWA, D3S1358, D5S818, D7S820, D8S1179, D13S317, D16S539, D18S51 and D21S11.

14. The method of claim 1 wherein one contributor of said mixture of DNA is known and another contributor of said mixture is unknown.

15. The method of claim 1 wherein said DNA database and said software application computer server are connected via a network.

16. The method of claim 1 wherein said DNA comprises short tandem repeats.

17. The method of claim 16 wherein said short tandem repeats are present in at least one locus comprising three alleles.

18. The method of claim 12 further comprising separately repeating the resolution method at said software application computer server for a third locus different from a second locus different from said first locus.

19. The method of claim 1 wherein said DNA database comprises a first DNA database and a second DNA database.

20. The method of claim 1 further comprising separately computing said peak fit ratio and said fitting residual for each of a plurality of loci, locus by locus at said software application computer server.

21. The method of claim 4 further comprising said client computer maintaining a second instance of a portion of said DNA database, said client computer running said software application independently of said software application computer server.

* * * * *

UNITED STATES PATENT AND TRADEMARK OFFICE
CERTIFICATE OF CORRECTION

| | |
|---|---|
| PATENT NO. | : 7,672,789 B2 |
| APPLICATION NO. | : 11/413183 |
| DATED | : March 2, 2010 |
| INVENTOR(S) | : Tse-Wei Wang et al. |

Page 1 of 1

It is certified that error appears in the above-identified patent and that said Letters Patent is hereby corrected as shown below:

Column 59, Claim 1, lines 39 - 40, "a computer implemented resolution methods," should read as follows:

-- a computer implemented resolution method, --.

Signed and Sealed this

Twentieth Day of April, 2010

David J. Kappos
*Director of the United States Patent and Trademark Office*